(12) United States Patent
Hossain et al.

(10) Patent No.: US 7,700,824 B2
(45) Date of Patent: Apr. 20, 2010

(54) METHODS

(75) Inventors: M. Zakir Hossain, Singapore (SG); Walter Hunziker, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 607 days.

(21) Appl. No.: 11/196,710

(22) Filed: Aug. 3, 2005

(65) Prior Publication Data

US 2006/0056948 A1    Mar. 16, 2006

(30) Foreign Application Priority Data

Aug. 4, 2004    (SG)  ............... 200404520-9

(51) Int. Cl.
*A01K 67/00* (2006.01)

(52) U.S. Cl. ................ 800/18; 800/9; 800/13

(58) Field of Classification Search ............ None
See application file for complete search history.

(56) References Cited

OTHER PUBLICATIONS

Capecchi, Scientific American, 1994, 270:52-9.*
Kanai et al, The EMBO J 2000;19:6778-91.*
Dey et al, J Virol 2002;76:9526-32.*
Tian et al, J Virol 2004;78:12657-64.*
Stein et al, Seminar in Oncol 2005;32:563-72.*
Levanon et al, EMBO Reports 2003;4:560-4.*
Polejaeva et al, Nature 2000;407:86.*
Wilmut, Cloning Stem Cell 2003;5:99-100.*
Yanagimachi, Mol Cell Endocrinol 2002;187:241-8.*
Denning, Nat Biotech 2001;19:559-562.*
Mullins et al, Journal of Clinical Investigation, 1996;97:1557-60.*
Wall et al, J Dairy Sci 1997;80:2213-24.*
Houdebine, J. Biotech. 1994;34:269-87.*
Moreadith et al., J. Mol. Med. 1997;75(3):208-16.*
Hossain et al. PNAS 2007;104:1631-6.*

* cited by examiner

*Primary Examiner*—Q. Janice Li
(74) *Attorney, Agent, or Firm*—Leydig, Voit & Mayer, Ltd.

(57) ABSTRACT

A non-human animal which has a reduced amount of functional TAZ polypeptide and/or TAZ-like polypeptide, or a reduced amount of nucleic acid encoding said polypeptide. A method for generating a non-human animal which develops PKD comprising reducing the amount of functional TAZ polypeptide and/or TAZ-like polypeptide, or nucleic acid encoding said polypeptide. A method of screening for compounds of use in preventing or treating PKD wherein a non-human animal is administered with a test compound and the effect of the test compound on the amount or function of TAZ polypeptide and/or a TAZ-like polypeptide and/or a polypeptide regulated by TAZ or a TAZ-like polypeptide function, or the amount of nucleic acid encoding said polypeptide, is assessed.

3 Claims, 10 Drawing Sheets

Figure 1:
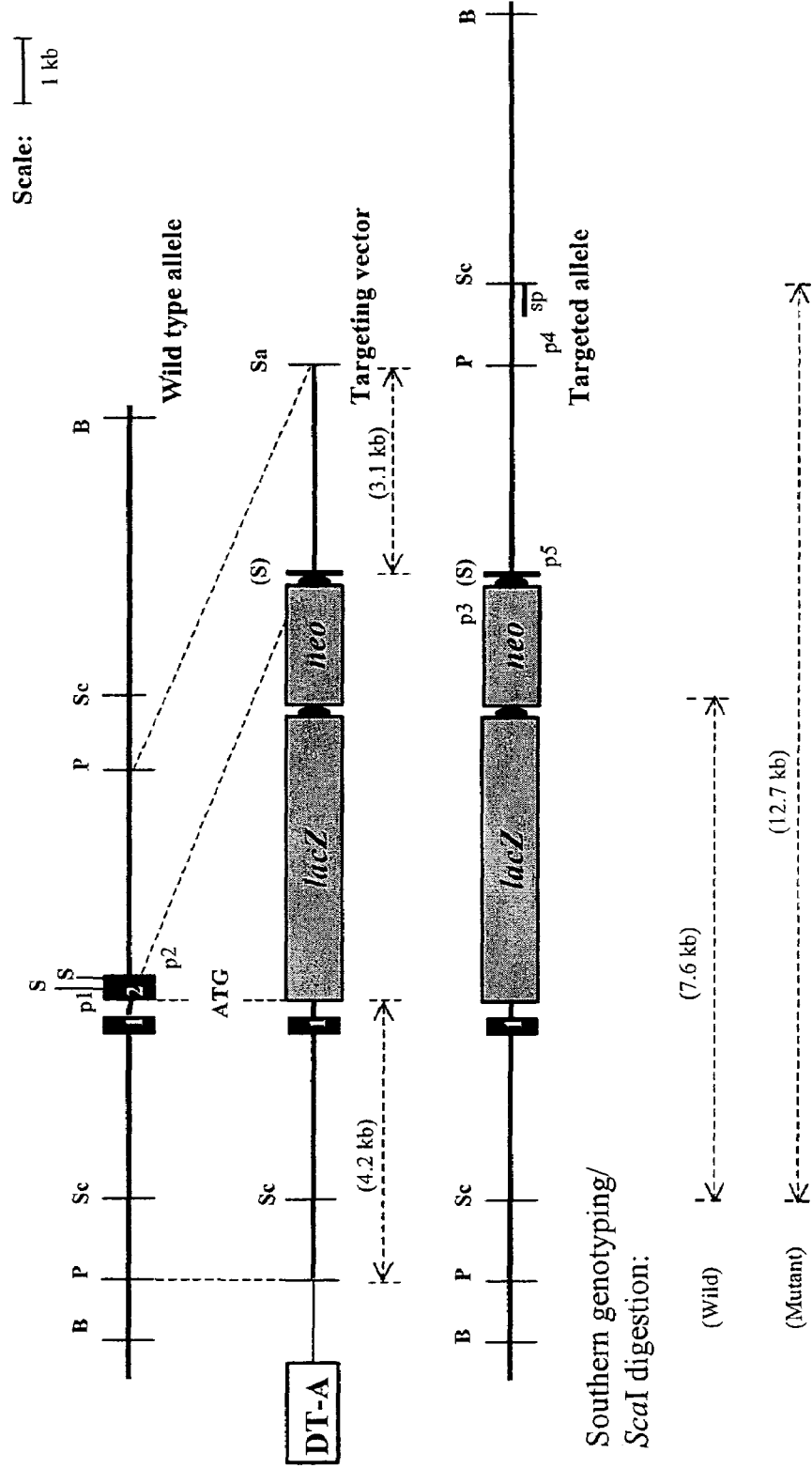

Figure 2
+/- 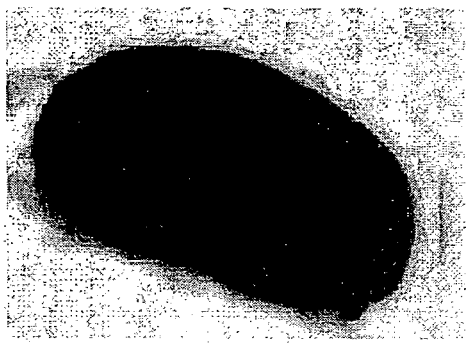  -/-
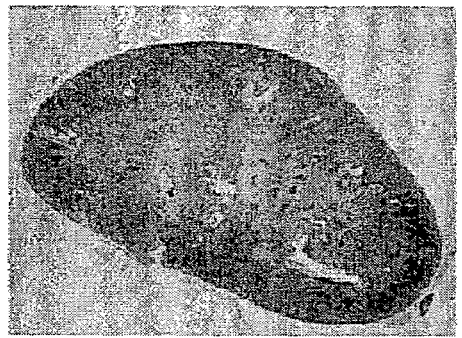 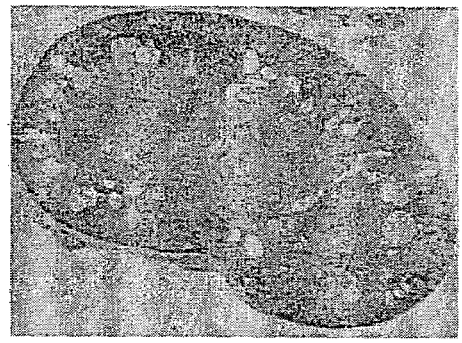
 

Figure 3: page 1

(A)

```
mnpasapppl pppgqqvihv tqdldtdlea lfnsvmnpkp sswrkkilpe sffkepdsgs
hsrqsstdss gghpgprlag gaqhvrshss paslqlgtga gaagspaqqh ahlrqqsydv
tdelplppgw emtftatgqr yflnhiekit twqdprkamn qplnhmnlhp avsstpvpqr
smavsqpnlv mnhqhqqqma pstlsqqnhp tqnppaglms mpnalttqqq qqqklrlqri
qmererirmr qeelmrqeaa lcrqlpmeae tlapvqaavn pptmtpdmrs itnnssdpfl
nggpyhsreq stdsglglgc ysvpttpedf lsnvdemdtg enagqtpmni npqqtrfpdf
ldclpgtnvd lgtlesedli plfndvesal nksepfltwl
```

(Sequence ID No. 1)

(B)

```
atgaatccgg cctcggcgcc ccctccgctc ccgccgcctg ggcagcaagt gatccacgtc
acgcaggacc tagacacaga cctcgaagcc ctcttcaact ctgtcatgaa tccgaagcct
agctcgtggc ggaagaagat cctgccggag tctttcttta aggagcctga ttcgggctcg
cactcgcgcc agtccagcac cgactcgtcg ggcggccacc cggggcctcg actggctggg
ggtgcccagc atgtccgctc gcactcgtcg cccgcgtccc tgcagctggg caccggcgcg
ggtgctgcgg gtagccccgc gcagcagcac gcgcacctcc gccagcagtc ctacgacgtg
accgacgagc tgccactgcc cccgggctgg gagatgacct tcacggccac tggccagagg
tacttcctca atcacataga aaaaatcacc acatggcaag accctaggaa ggcgatgaat
cagcctctga atcatatgaa cctccaccct gccgtcagtt ccacaccagt gcctcagagg
tccatggcag tatcccagcc aaatctcgtg atgaatcacc aacaccagca gcagatggcc
cccagtaccc tgagccagca gaaccacccc actcagaacc cacccgcagg gctcatgagt
atgcccaatg cgctgaccac tcagcagcag cagcagcaga actgcggct cagagaatc
cagatggaga gagaaaggat tcgaatgcgc caagaggagc tcatgaggca ggaagctgcc
ctctgtcgac agctccccat ggaagctgag actcttgccc cagttcaggc tgctgtcaac
ccacccacga tgacccccaga catgagatcc atcactaata atagctcaga tccttttcctc
aatggagggc catatcattc gagggagcag agcactgaca gtggcctggg gttagggtgc
tacagtgtcc ccacaactcc ggaggacttc ctcagcaatg tggatgagat ggatacagga
gaaaacgcag gacaaacacc catgaacatc aatccccaac agacccgttt ccctgatttc
cttgactgtc ttccaggaac aaacgttgac ttaggaactt tggaatctga agacctgatc
cccctcttca atgatgtaga gtctgctctg aacaaaagtg agcccttcct aacctggctg
taa
```

(Sequence ID No. 2)

(C)

```
mnpssvphpl pppgqqvihv tqdldtdlea lfnsvmnpkp sswrkkilpe sffkepdsgs
hsrqsstdss gghpgprlag gaqhvrshss paslqlgtga gaaggpaqqh ahlrqqsydv
tdelplppgw emtftatgqr yflnhiekit twqdprkvmn qplnhvnlhp sitstsvpqr
smavsqpnla mnhqhqqvva tslspqnhpt qnqptglmsv pnalttqqqq qqklrlqriq
mererirmrq eelmrqeaal crqlpmetet mapvntpams tdmrsvtnss sdpflnggpy
hsreqstdsg lglgcysvpt tpedflsnmd emdtgensgq tpmtvnpqqt rfpdfldclp
gtnvdlgtle sedlipfnd vesvlnksep fltwl
```

(Sequence ID No. 3)

Figure 3: page 2

(D)

```
atgaatccgt cctcggtgcc ccatccgctc ccgccgccag ggcagcaagt catccacgtc
acgcaggacc tggacaccga cctcgaagcc ctcttcaact ctgtcatgaa ccccaagccc
agctcatggc ggaaaaagat cctcccggag tccttcttta aggagcccga ttccggctcg
cactcgcgcc aatccagcac agactcatca ggcggccacc cggggcctcg actagctggc
ggcgcgcagc acgtccgctc gcactcgtcg cccgcatccc tgcagctggg caccggtgcg
ggagccgctg gaggccctgc acagcagcat gcacatctcc gccagcagtc ctatgacgtg
accgacgagc tgccgttgcc ccccggggtgg gagatgacct tcacggccac tggccagaga
tacttcctta atcacataga gaaaatcacc acatggcaag accccaggaa ggtgatgaat
cagcctctga atcatgtgaa cctccacccg tccatcactt ccacctcggt gccacagagg
tccatggcag tgtcccagcc gaatctcgca atgaatcacc aacaccagca agtcgtggcc
actagcctga gtccacagaa ccacccgact cagaaccaac ccacagggct catgagtgtg
cccaatgcac tgaccactca gcagcagcag cagcagaaac tgcggcttca gaggatccag
atggagagag agaggattag gatgcgtcaa gaggagctca tgaggcagga agctgccctc
tgccgacagc tccccatgga aaccgagacc atggcccctg tcaacacgcc tgccatgagc
acagatatga gatctgtcac caacagtagc tcagatcctt tcctcaatgg agggccctat
cattcacggg agcagagcac agacagtggc ctggggttag ggtgctacag tgtccccaca
actccagaag acttcctcag caacatggac gagatggata caggtgaaaa ttccggtcag
acacccatga ccgtcaatcc ccagcagacc cgcttccctg atttcctgga ctgccttcca
ggaacaaatg ttgacctcgg gactttggag tctgaagatc tgatccctct cttcaatgat
gtagagtctg ttctgaacaa aagcgagccc tttctaacct ggctgtaa
```

(Sequence ID No. 4)

Figure 4: page 1

(A)

```
mdpgqqpppq papqgqgqpp sqppqgqgpp sgpgqpapaa tqaapqappa ghqivhvrgd
setdlealfn avmnpktanv pqtvpmrlrk lpdsffkppe pkshsrqast dagtagaltp
qhvrahsspa slqlgavspg tltptgvvsg paatptaqhl rqssfeipdd vplpagwema
ktssgqryfl nhidqtttwq dprkamlsqm nvtaptsppv qqnmmnsasa mnqrisqsap
vkqppplapq spqggvmggs nsnqqqqmrl qqlqmekerl rlkqqellrq vrpqelalrs
qlptleqdgg tqnpvsspgm sqelrtmttn ssdpflnsgt yhsrdestds glsmssysvp
rtpddflnsv demdtgdtin qstlpsqqnr fpdyleaipg tnvdlgtleg dgmniegeel
mpslqealss dilndmesvl aatkldkesf ltwl
```

(Sequence ID No. 5)

(B)

```
atggatcccg ggcagcagcc gccgcctcaa ccggccccc agggccaagg gcagccgcct
tcgcagcccc cgcaggggca gggcccgccg tccggacccg ggcaaccggc acccgcggcg
acccaggcgg cgccgcaggc accccccgcc gggcatcaga tcgtgcacgt ccgcggggac
tcggagaccg acctggaggc gctcttcaac gccgtcatga accccaagac ggccaacgtg
ccccagaccg tgcccatgag gctccggaag ctgccgact ccttcttcaa gccgccggag
cccaaatccc actcccgaca ggccagtact gatgcaggca ctgcaggagc cctgactcca
cagcatgttc gagctcattc ctctccagct tctctgcagt gggagctgt ttctcctggg
acactgaccc ccactggagt agtctctggc ccagcagcta cacccacagc tcagcatctt
cgacagtctt cttttgagat acctgatgat gtacctctgc agcaggttg ggagatggca
aagacatctt ctggtcagag atacttctta aatcacatcg atcagacaac aacatggcag
gaccccagga aggccatgct gtcccagatg aacgtcacag cccccaccag tccaccagtg
cagcagaata tgatgaactc ggcttcagcc atgaaccaga gaatcagtca gagtgctcca
gtgaaacagc caccaccct ggctcccag agcccacagg gaggcgtcat gggtggcagc
aactccaacc agcagcaaca gatgcgactg cagcaactgc agatggagaa ggagaggctg
cggctgaaac agcaagaact gcttcggcag gtgaggccac aggagttagc cctgcgtagc
cagttaccaa cactggagca ggatggtggg actcaaaatc cagtgtcttc tcccgggatg
tctcaggaat tgagaacaat gacgaccaat agctcagatc ctttccttaa cagtggcacc
tatcactctc gagatgagag tacagacagt ggactaagca tgagcagcta cagtgtccct
cgaaccccag atgacttcct gaacagtgtg gatgagatgg atacaggtga tactatcaac
caaagcaccc tgccctcaca gcagaaccgt ttcccagact accttgaagc cattcctggg
acaaatgtgg accttggaac actggaagga gatggaatga acatagaagg agaggagctg
atgccaagtc tgcaggaagc tttgagttct gacatcctta tgacatgga gtctgttttg
gctgccacca agctagataa agaaagcttt cttacatggt tatag
```

(Sequence ID No. 6)

(C)

```
mepaqqpppq papqgpapps vspagtpaap pappaghqvv hvrgdsetdl ealfnavmnp
ktanvpqtvp mrlrklpdsf fkppepkshs rqastdagta galtpqhvra hsspaslqlg
avspgtltas gvvsgpaaap aaqhlrqssf eipddvplpa gwemaktssg qryflnhndq
tttwqdprka mlsqlnvpap aspavpqtlm nsasgplpdg weqamtqdge vyyinhknkt
tswldprldp rfamnqritq sapvkqpppl apqspqggvl gggssnqqqq iqlqqlqmek
erlrlkqqel frqelalrsq lptleqdggt pnavsspgms qelrtmttns sdpflnsgty
hsrdestdsg lsmssysipr tpddflnsvd emdtgdtisq stlpsqqsrf pdylealpgt
nvdlgtlegd amniegeelm pslqealsse ildvesvlaa tkldkesflt wl
```

(Sequence ID No. 7)

Figure 4: page 2

(D)

```
atggagcccg cgcaacagcc gccgccccag ccggccccgc aaggccccgc gccgccgtcc
gtgtctccgg ccgggacccc cgcggccccg cccgcacccc cggccggcca ccaggtcgtg
cacgtccgcg gggactcgga gaccgacttg gaggcgctct tcaatgccgt catgaacccc
aagacggcca acgtgcctca gaccgtgccc atgcggcttc gcaagctgcc cgactccttc
ttcaagccgc ctgagcccaa gtcccactcg cgacaggcca gtactgatgc aggtactgcg
ggagctctga ctccacagca tgttcgagct cactcctctc cagcctccct gcagctgggt
gccgtttctc ctgggacact cacagccagt ggcgttgtct ctggccctgc cgctgcccct
gcagctcagc atctccggca gtcctccttt gagatccctg atgatgtacc actgccagca
ggctgggaga tggccaagac atcttctggt caaagatact tcttaaatca caacgatcag
acaacaacat ggcaggaccc ccggaaggcc atgctttcgc aactgaacgt tcctgcgcct
gccagcccag cggtgcccca gacgctgatg aattctgcct caggacctct tcctgatgga
tgggagcaag ccatgactca ggatgagaa gtttactaca taaaccataa gaacaagacc
acatcctggc tggacccaag gctggaccct cgttttgcca tgaaccagag gatcactcag
agtgctccag tgaagcagcc cccacccttg gctcccaga gcccacaggg aggcgtcctg
ggtggaggca gttccaacca gcagcagcaa atacagctgc agcagttaca gatggagaag
gagagactgc ggttgaaaca acaggaatta tttcggcagg aattagctct gcgcagccag
ttgcctacac tggagcagga tggagggact ccgaatgcag tgtcttctcc tgggatgtct
caggaattga gaacaatgac aaccaatagt tccgatccct ttcttaacag tggcacctat
cactctcgag atgagagcac agacagcggc ctcagcatga gcagctacag catccctcgg
accccagacg acttcctcaa cagtgtggat gaaatggata caggagacac catcagccaa
agcacccctgc cgtcacagca gagccgcttc cccgactacc tggaagccct ccctgggaca
aatgtggacc ttggcacact ggaaggagat gcaatgaaca tagaagggga ggagctgatg
cccagtctgc aggaagcgct gagttccgaa atcttggacg tggagtctgt gttggctgcc
accaagctag ataaagaaag ctttctcacg tggttatag
```

(Sequence ID No. 8)

(E)

```
mdpgqpqpqq ppqaaqppap qqaapqppga gsgapggaaq ppgagpppag hqivhvrgds
etdlealfna vmnpkganvp htlpmrlrkl pdsffkppep kahsrqastd agtagaltpq
hvrahsspas lqlgavspgt ltpsgvvtgp gapssqhlrq ssfeipddvp lppgwemakt
psgqryflnh idqtttwqdp rkamlsqmnv taptsppvqq nlmnsasamn qrisqsapvk
qppplapqsp qggvmggsss nqqqqmrlqq lqmekerlrl khqellrqel alrsqlptme
qdggsqnpvs spgmsqelrt mttnssdpfl nsgtyhsrde stdsglsmss ysvprtpddf
lnsvdemdtg dsisqsnips hqnrfpdyle aipgtnvdlg tlegdgmnie geelmpslqe
alssdilndm esvlaatkpd kesfltwl
```

(Sequence ID No. 9)

Figure 4: page 3

(F)

```
atggatcccg ggcagcctca gccgcagcag ccgccgcagg cggcgcagcc cccggccccg
cagcaggcgg ccccgcagcc cccgggcgcg gggtcgggag ctccgggagg cgccgcgcag
ccgccgggcg cggggccccc tccggcgggg caccagatcg tccatgtgcg gggcgactcc
gagaccgacc tggaggctct cttcaacgcc gtgatgaacc ccaagggcgc caacgtgccg
cacacgctgc ccatgcggct ccgcaagctg ccggactcct tcttcaagcc gcccgagccc
aaagctcact cccgccaggc cagcactgac gcagggacag caggagccct gaccccctcag
catgttcgtg ctcattcctc tccagcatca ctgcagctgg gggccgtctc ccctgggacg
ctcacaccct ccggagtagt gaccggaccc ggagctccgt cttctcagca tctccgccag
tcttcatttg agatccctga tgatgtacct ctgccaccgg gctgggagat ggccaaaaca
ccatctggac agagatactt ccttaatcat attgatcaaa caacaacatg gcaagatccc
aggaaggcca tgctttccca gatgaacgtt acagctccca ccagtcctcc cgtgcaacag
aacttaatga actcagcatc agccatgaat cagcgcatca gccaaagtgc tccagtgaaa
cagccacccc ctctggctcc tcagagtccc caaggtggtg tcatgggtgg gagtagctcc
aatcagcaac aacagatgag acttcagcag ctacagatgg agaaggaaag gctgagactg
aagcatcaag aactgcttcg gcaggaattg gctctccgta gccagcttcc aacgatggaa
caagatggtg gatctcaaaa tcccgtatca tctcctggaa tgtctcagga actgaggact
atgactacaa atagttctga tccctttctt aacagtggaa catatcactc cagagatgaa
agcacagata gcggacttag catgagcagt tacagcgtac ccagaacccc cgatgacttc
ctgaacagtg ttgatgagat ggatacaggt gacagtatca gccaaagtaa cataccgtcc
catcagaacc gattcccaga ctaccttgaa gccattccag ggacaaatgt ggaccttggg
acactggaag gagatgggat gaatatagaa ggagaagaac tgatgccaag tctgcaagag
gctttgagct ctgacatcct aaatgacatg gaatctgtct tggcagccac caagccagat
aaagagagtt ttcttacttg gttatag
```

(Sequence ID No. 10)

SEQUENCE LISTING

```
<160> NUMBER OF SEQ ID NOS: 10

<210> SEQ ID NO 1
<211> LENGTH: 400
<212> TYPE: PRT
<213> ORGANISM: Homo sapiens
<300> PUBLICATION INFORMATION:
<308> DATABASE ACCESSION NUMBER: GENBANK NP_056287.1
<309> DATABASE ENTRY DATE: 2005-05-20
<313> RELEVANT RESIDUES: (1)..(400)

<400> SEQUENCE: 1

Met Asn Pro Ala Ser Ala Pro Pro Pro Leu Pro Pro Pro Gly Gln Gln
1               5                   10                  15

Val Ile His Val Thr Gln Asp Leu Asp Thr Asp Leu Glu Ala Leu Phe
            20                  25                  30

Asn Ser Val Met Asn Pro Lys Pro Ser Ser Trp Arg Lys Lys Ile Leu
        35                  40                  45

Pro Glu Ser Phe Phe Lys Glu Pro Asp Ser Gly Ser His Ser Arg Gln
    50                  55                  60

Ser Ser Thr Asp Ser Ser Gly Gly His Pro Gly Pro Arg Leu Ala Gly
65                  70                  75                  80

Gly Ala Gln His Val Arg Ser His Ser Ser Pro Ala Ser Leu Gln Leu
                85                  90                  95

Gly Thr Gly Ala Gly Ala Ala Gly Ser Pro Ala Gln Gln His Ala His
            100                 105                 110

Leu Arg Gln Gln Ser Tyr Asp Val Thr Asp Glu Leu Pro Leu Pro Pro
        115                 120                 125

Gly Trp Glu Met Thr Phe Thr Ala Thr Gly Gln Arg Tyr Phe Leu Asn
    130                 135                 140

His Ile Glu Lys Ile Thr Thr Trp Gln Asp Pro Arg Lys Ala Met Asn
145                 150                 155                 160

Gln Pro Leu Asn His Met Asn Leu His Pro Ala Val Ser Ser Thr Pro
                165                 170                 175

Val Pro Gln Arg Ser Met Ala Val Ser Gln Pro Asn Leu Val Met Asn
            180                 185                 190

His Gln His Gln Gln Gln Met Ala Pro Ser Thr Leu Ser Gln Gln Asn
        195                 200                 205

His Pro Thr Gln Asn Pro Pro Ala Gly Leu Met Ser Met Pro Asn Ala
    210                 215                 220

Leu Thr Thr Gln Gln Gln Gln Gln Gln Lys Leu Arg Leu Gln Arg Ile
```

```
                225                 230                 235                 240

Gln Met Glu Arg Glu Arg Ile Arg Met Arg Gln Glu Glu Leu Met Arg
                    245                 250                 255

Gln Glu Ala Ala Leu Cys Arg Gln Leu Pro Met Glu Ala Glu Thr Leu
                260                 265                 270

Ala Pro Val Gln Ala Ala Val Asn Pro Pro Thr Met Thr Pro Asp Met
            275                 280                 285

Arg Ser Ile Thr Asn Asn Ser Ser Asp Pro Phe Leu Asn Gly Gly Pro
        290                 295                 300

Tyr His Ser Arg Glu Gln Ser Thr Asp Ser Gly Leu Gly Leu Gly Cys
305                 310                 315                 320

Tyr Ser Val Pro Thr Thr Pro Glu Asp Phe Leu Ser Asn Val Asp Glu
                325                 330                 335

Met Asp Thr Gly Glu Asn Ala Gly Gln Thr Pro Met Asn Ile Asn Pro
                340                 345                 350

Gln Gln Thr Arg Phe Pro Asp Phe Leu Asp Cys Leu Pro Gly Thr Asn
            355                 360                 365

Val Asp Leu Gly Thr Leu Glu Ser Glu Asp Leu Ile Pro Leu Phe Asn
        370                 375                 380

Asp Val Glu Ser Ala Leu Asn Lys Ser Glu Pro Phe Leu Thr Trp Leu
385                 390                 395                 400

<210> SEQ ID NO 2
<211> LENGTH: 1203
<212> TYPE: DNA
<213> ORGANISM: Homo sapiens
<220> FEATURE:
<221> NAME/KEY: misc_feature
<222> LOCATION: (1)..(1203)
<223> OTHER INFORMATION: Encodes the protein of SEQ ID NO:1

<400> SEQUENCE: 2
atgaatccgg cctcggcgcc ccctccgctc ccgccgcctg ggcagcaagt gatccacgtc      60
acgcaggacc tagacacaga cctcgaagcc ctcttcaact ctgtcatgaa tccgaagcct     120
agctcgtggc ggaagaagat cctgccggag tctttcttta aggagcctga ttcgggctcg     180
cactcgcgcc agtccagcac cgactcgtcg ggcggccacc cggggcctcg actggctggg     240
ggtgcccagc atgtccgctc gcactcgtcg cccgcgtccc tgcagctggg caccggcgcg     300
ggtgctgcgg gtagccccgc gcagcagcac gcgcacctcc gccagcagtc ctacgacgtg     360
accgacgagc tgccactgcc cccgggctgg agatgacct tcacggccac tggccagagg     420
tacttcctca tcacataga aaaatcacc acatggcaag accctaggaa ggcgatgaat     480
cagcctctga tcatatgaa cctccaccct gccgtcagtt ccacaccagt gcctcagagg     540
tccatggcag tatcccagcc aaatctcgtg atgaatcacc aacaccagca gcagatggcc     600
cccagtaccc tgagccagca gaaccacccc actcagaacc cacccgcagg gctcatgagt     660
atgcccaatg cgctgaccac tcagcagcag cagcagcaga actgcggct cagagaatc     720 cagatggaga gagaaaggat tcgaatgcgc aagaggagc tcatgaggca ggaagctgcc     780
ctctgtcgac agctccccat ggaagctgag actcttgccc cagttcaggc tgctgtcaac     840
ccacccacga tgaccccaga catgagatcc atcactaata tagctcaga tcctttcctc     900 aatggagggc catatcattc gagggagcag agcactgaca gtggcctggg gttagggtgc     960
tacagtgtcc ccacaactcc ggaggacttc ctcagcaatg tggatgagat ggatacagga    1020
gaaaacgcag gacaaacacc catgaacatc aatccccaac agaccgtt ccctgatttc    1080
```

```
cttgactgtc ttccaggaac aaacgttgac ttaggaactt tggaatctga agacctgatc    1140
cccctcttca atgatgtaga gtctgctctg aacaaaagtg agcccttttct aacctggctg   1200 taa                                                                  1203
```

<210> SEQ ID NO 3
<211> LENGTH: 395
<212> TYPE: PRT
<213> ORGANISM: Mus musculus
<300> PUBLICATION INFORMATION:
<308> DATABASE ACCESSION NUMBER: GENBANK CAC17733
<309> DATABASE ENTRY DATE: 2005-04-15
<313> RELEVANT RESIDUES: (1)..(395)

<400> SEQUENCE: 3

```
Met Asn Pro Ser Ser Val Pro His Pro Leu Pro Pro Gly Gln Gln
1               5                   10                  15

Val Ile His Val Thr Gln Asp Leu Asp Thr Asp Leu Glu Ala Leu Phe
            20                  25                  30

Asn Ser Val Met Asn Pro Lys Pro Ser Ser Trp Arg Lys Lys Ile Leu
        35                  40                  45

Pro Glu Ser Phe Phe Lys Glu Pro Asp Ser Gly Ser His Ser Arg Gln
    50                  55                  60

Ser Ser Thr Asp Ser Ser Gly Gly His Pro Gly Pro Arg Leu Ala Gly
65                  70                  75                  80

Gly Ala Gln His Val Arg Ser His Ser Ser Pro Ala Ser Leu Gln Leu
                85                  90                  95

Gly Thr Gly Ala Gly Ala Ala Gly Gly Pro Ala Gln Gln His Ala His
            100                 105                 110

Leu Arg Gln Gln Ser Tyr Asp Val Thr Asp Glu Leu Pro Leu Pro Pro
        115                 120                 125

Gly Trp Glu Met Thr Phe Thr Ala Thr Gly Gln Arg Tyr Phe Leu Asn
    130                 135                 140

His Ile Glu Lys Ile Thr Thr Trp Gln Asp Pro Arg Lys Val Met Asn
145                 150                 155                 160

Gln Pro Leu Asn His Val Asn Leu His Pro Ser Ile Thr Ser Thr Ser
                165                 170                 175

Val Pro Gln Arg Ser Met Ala Val Ser Gln Pro Asn Leu Ala Met Asn
            180                 185                 190

His Gln His Gln Gln Val Val Ala Thr Ser Leu Ser Pro Gln Asn His
        195                 200                 205

Pro Thr Gln Asn Gln Pro Thr Gly Leu Met Ser Val Pro Asn Ala Leu
    210                 215                 220

Thr Thr Gln Gln Gln Gln Gln Lys Leu Arg Leu Arg Ile Gln
225                 230                 235                 240

Met Glu Arg Glu Arg Ile Arg Met Arg Gln Glu Glu Leu Met Arg Gln
                245                 250                 255

Glu Ala Ala Leu Cys Arg Gln Leu Pro Met Glu Thr Glu Thr Met Ala
            260                 265                 270

Pro Val Asn Thr Pro Ala Met Ser Thr Asp Met Arg Ser Val Thr Asn
        275                 280                 285

Ser Ser Ser Asp Pro Phe Leu Asn Gly Gly Pro Tyr His Ser Arg Glu
    290                 295                 300

Gln Ser Thr Asp Ser Gly Leu Gly Leu Gly Cys Tyr Ser Val Pro Thr
305                 310                 315                 320
```

-continued

```
Thr Pro Glu Asp Phe Leu Ser Asn Met Asp Glu Met Asp Thr Gly Glu
            325                 330                 335

Asn Ser Gly Gln Thr Pro Met Thr Val Asn Pro Gln Gln Thr Arg Phe
        340                 345                 350

Pro Asp Phe Leu Asp Cys Leu Pro Gly Thr Asn Val Asp Leu Gly Thr
    355                 360                 365

Leu Glu Ser Glu Asp Leu Ile Pro Leu Phe Asn Asp Val Glu Ser Val
370                 375                 380

Leu Asn Lys Ser Glu Pro Phe Leu Thr Trp Leu
385                 390                 395

<210> SEQ ID NO 4
<211> LENGTH: 1188
<212> TYPE: DNA
<213> ORGANISM: Mus musculus
<220> FEATURE:
<221> NAME/KEY: misc_feature
<222> LOCATION: (1)..(1188)
<223> OTHER INFORMATION: Encodes the protein of SEQ ID NO:3

<400> SEQUENCE: 4
atgaatccgt cctcggtgcc ccatccgctc ccgccgccag ggcagcaagt catccacgtc     60
acgcaggacc tggacaccga cctcgaagcc ctcttcaact ctgtcatgaa ccccaagccc    120
agctcatggc ggaaaaagat cctcccggag tccttcttta aggagcccga ttccggctcg    180
cactcgcgcc aatccagcac agactcatca ggcggccacc cggggcctcg actagctggc    240
ggcgcgcagc acgtccgctc gcactcgtcg cccgcatccc tgcagctggg caccggtgcg    300
ggagccgctg gaggccctgc acagcagcat gcacatctcc gccagcagtc ctatgacgtg    360
accgacgagc tgccgttgcc ccccggggtgg gagatgacct tcacggccac tggccagaga    420
tacttcctta atcacataga gaaaatcacc acatggcaag accccaggaa ggtgatgaat    480
cagcctctga atcatgtgaa cctccacccg tccatcactt ccacctcggt gcccagagag    540
tccatggcag tgtcccagcc gaatctcgca atgaatcacc aacaccagca agtcgtggcc    600
actagcctga gtccacagaa ccacccgact cagaaccaac ccacagggct catgagtgtg    660
cccaatgcac tgaccactca gcagcagcag cagcagaaac tgcggcttca gaggatccag    720
atggagagag agaggattag gatgcgtcaa gaggagctca tgaggcagga agctgccctc    780
tgccgacagc tccccatgga aaccgagacc atggcccctg tcaacacgcc tgccatgagc    840
acagatatga gatctgtcac caacagtagc tcagatcctt tcctcaatgg agggccctat    900
cattcacggg agcagagcac agacagtggc ctggggttag ggtgctacag tgtccccaca    960
actccagaag acttcctcag caacatggac gagatggata caggtgaaaa ttccggtcag   1020
acacccatga ccgtcaatcc ccagcagacc cgcttccctg atttcctgga ctgccttcca   1080
ggaacaaatg ttgacctcgg gactttggag tctgaagatc tgatccctct cttcaatgat   1140
gtagagtctg ttctgaacaa aagcgagccc tttctaacct ggctgtaa              1188

<210> SEQ ID NO 5
<211> LENGTH: 454
<212> TYPE: PRT
<213> ORGANISM: Homo sapiens
<300> PUBLICATION INFORMATION:
<308> DATABASE ACCESSION NUMBER: GENBANK NP_006097
<309> DATABASE ENTRY DATE: 2005-07-04
<313> RELEVANT RESIDUES: (1)..(454)

<400> SEQUENCE: 5
```

```
Met Asp Pro Gly Gln Gln Pro Pro Gln Pro Ala Pro Gly Gln
1               5                  10                 15

Gly Gln Pro Pro Ser Gln Pro Pro Gln Gly Gln Gly Pro Pro Ser Gly
            20                  25                  30

Pro Gly Gln Pro Ala Pro Ala Ala Thr Gln Ala Ala Pro Gln Ala Pro
            35                  40                  45

Pro Ala Gly His Gln Ile Val His Val Arg Gly Asp Ser Glu Thr Asp
        50                  55                  60

Leu Glu Ala Leu Phe Asn Ala Val Met Asn Pro Lys Thr Ala Asn Val
65                  70                  75                  80

Pro Gln Thr Val Pro Met Arg Leu Arg Lys Leu Pro Asp Ser Phe Phe
                85                  90                  95

Lys Pro Pro Glu Pro Lys Ser His Ser Arg Gln Ala Ser Thr Asp Ala
            100                 105                 110

Gly Thr Ala Gly Ala Leu Thr Pro Gln His Val Arg Ala His Ser Ser
            115                 120                 125

Pro Ala Ser Leu Gln Leu Gly Ala Val Ser Pro Gly Thr Leu Thr Pro
        130                 135                 140

Thr Gly Val Val Ser Gly Pro Ala Ala Thr Pro Thr Ala Gln His Leu
145                 150                 155                 160

Arg Gln Ser Ser Phe Glu Ile Pro Asp Asp Val Pro Leu Pro Ala Gly
                165                 170                 175

Trp Glu Met Ala Lys Thr Ser Ser Gly Gln Arg Tyr Phe Leu Asn His
            180                 185                 190

Ile Asp Gln Thr Thr Thr Trp Gln Asp Pro Arg Lys Ala Met Leu Ser
        195                 200                 205

Gln Met Asn Val Thr Ala Pro Thr Ser Pro Pro Val Gln Gln Asn Met
210                 215                 220

Met Asn Ser Ala Ser Ala Met Asn Gln Arg Ile Ser Gln Ser Ala Pro
225                 230                 235                 240

Val Lys Gln Pro Pro Pro Leu Ala Pro Gln Ser Pro Gln Gly Gly Val
                245                 250                 255

Met Gly Gly Ser Asn Ser Asn Gln Gln Gln Gln Met Arg Leu Gln Gln
            260                 265                 270

Leu Gln Met Glu Lys Glu Arg Leu Arg Leu Lys Gln Gln Glu Leu Leu
        275                 280                 285

Arg Gln Val Arg Pro Gln Glu Leu Ala Leu Arg Ser Gln Leu Pro Thr
290                 295                 300

Leu Glu Gln Asp Gly Gly Thr Gln Asn Pro Val Ser Ser Pro Gly Met
305                 310                 315                 320

Ser Gln Glu Leu Arg Thr Met Thr Thr Asn Ser Ser Asp Pro Phe Leu
                325                 330                 335

Asn Ser Gly Thr Tyr His Ser Arg Asp Glu Ser Thr Asp Ser Gly Leu
            340                 345                 350

Ser Met Ser Ser Tyr Ser Val Pro Arg Thr Pro Asp Asp Phe Leu Asn
        355                 360                 365

Ser Val Asp Glu Met Asp Thr Gly Asp Thr Ile Asn Gln Ser Thr Leu
370                 375                 380

Pro Ser Gln Gln Asn Arg Phe Pro Asp Tyr Leu Glu Ala Ile Pro Gly
385                 390                 395                 400

Thr Asn Val Asp Leu Gly Thr Leu Glu Gly Asp Gly Met Asn Ile Glu
                405                 410                 415

Gly Glu Glu Leu Met Pro Ser Leu Gln Glu Ala Leu Ser Ser Asp Ile
```

Leu Asn Asp Met Glu Ser Val Leu Ala Ala Thr Lys Leu Asp Lys Glu
          420                 425                 430

Ser Phe Leu Thr Trp Leu
    450

<210> SEQ ID NO 6
<211> LENGTH: 1365
<212> TYPE: DNA
<213> ORGANISM: Homo sapiens
<220> FEATURE:
<221> NAME/KEY: misc_feature
<222> LOCATION: (1)..(1365)
<223> OTHER INFORMATION: Encodes the protein of SEQ ID NO:5

<400> SEQUENCE: 6

| | | |
|---|---|---|
| atggatcccg ggcagcagcc gccgcctcaa ccggcccccc agggccaagg gcagccgcct | 60 |
| tcgcagcccc cgcaggggca gggcccgccg tccggacccg gcaaccggc acccgcggcg | 120 |
| acccaggcgg cgccgcaggc accccccgcc gggcatcaga tcgtgcacgt ccgcggggac | 180 |
| tcggagaccg acctggaggc gctcttcaac gccgtcatga cccccaagac ggccaacgtg | 240 |
| ccccagaccg tgcccatgag gctccggaag ctgcccgact ccttcttcaa gccgccggag | 300 |
| cccaaatccc actcccgaca ggccagtact gatgcaggca ctgcaggagc cctgactcca | 360 |
| cagcatgttc gagctcattc ctctccagct tctctgcagt tgggagctgt ttctcctggg | 420 |
| acactgaccc ccactggagt agtctctggc ccagcagcta cacccacagc tcagcatctt | 480 |
| cgacagtctt cttttgagat acctgatgat gtacctctgc cagcaggttg ggagatggca | 540 |
| aagcacatctt ctggtcagag atacttctta aatcacatcg atcagacaac aacatggcag | 600 |
| gaccccagga aggccatgct gtcccagatg aacgtcacag ccccccaccag tccaccagtg | 660 |
| cagcagaata tgatgaactc ggcttcagcc atgaaccaga gaatcagtca gagtgctcca | 720 |
| gtgaaacagc caccacccct ggctccccag agcccacagg gaggcgtcat gggtggcagc | 780 |
| aactccaacc agcagcaaca gatgcgactg cagcaactgc agatggagaa ggagaggctg | 840 |
| cggctgaaaa cagcaagaac tgcttcggcag gtgaggccac aggagttagc cctgcgtagc | 900 |
| cagttaccaa cactggagca ggatggtggg actcaaaatc cagtgtcttc tcccgggatg | 960 |
| tctcaggaat tgagaacaat gacgaccaat agctcagatc ctttccttaa cagtggcacc | 1020 |
| tatcactctc gagatgagag tacagacagt ggactaagca tgagcagcta cagtgtccct | 1080 |
| cgaaccccag atgacttcct gaacagtgtg gatgagatgg atacaggtga ctatcaac | 1140 |
| caaagcaccc tgccctcaca gcagaaccgt ttcccagact accttgaagc cattcctggg | 1200 |
| acaaatgtgg accttggaac actggaagga gatggaatga catagaagg agaggagctg | 1260 |
| atgccaagtc tgcaggaagc tttgagttct gacatcctta atgacatgga gtctgtttg | 1320 |
| gctgccacca agctagataa agaaagcttt cttacatggt tatag | 1365 |

<210> SEQ ID NO 7
<211> LENGTH: 472
<212> TYPE: PRT
<213> ORGANISM: Mus musculus
<300> PUBLICATION INFORMATION:
<308> DATABASE ACCESSION NUMBER: GENBANK AAH39125
<309> DATABASE ENTRY DATE: 2005-07-06
<313> RELEVANT RESIDUES: (1)..(472)

<400> SEQUENCE: 7

Met Glu Pro Ala Gln Gln Pro Pro Pro Gln Pro Ala Pro Gln Gly Pro

```
1               5                   10                  15
Ala Pro Pro Ser Val Ser Pro Ala Gly Thr Pro Ala Ala Pro Pro Ala
                20                  25                  30

Pro Pro Ala Gly His Gln Val Val His Val Arg Gly Asp Ser Glu Thr
                35                  40              45

Asp Leu Glu Ala Leu Phe Asn Ala Val Met Asn Pro Lys Thr Ala Asn
                50                  55              60

Val Pro Gln Thr Val Pro Met Arg Leu Arg Lys Leu Pro Asp Ser Phe
65                      70                  75                  80

Phe Lys Pro Pro Glu Pro Lys Ser His Ser Arg Gln Ala Ser Thr Asp
                85                  90              95

Ala Gly Thr Ala Gly Ala Leu Thr Pro Gln His Val Arg Ala His Ser
                100                 105                 110

Ser Pro Ala Ser Leu Gln Leu Gly Ala Val Ser Pro Gly Thr Leu Thr
                115                 120             125

Ala Ser Gly Val Val Ser Gly Pro Ala Ala Pro Ala Ala Gln His
                130                 135                 140

Leu Arg Gln Ser Ser Phe Glu Ile Pro Asp Asp Val Pro Leu Pro Ala
145                 150                 155                 160

Gly Trp Glu Met Ala Lys Thr Ser Ser Gly Gln Arg Tyr Phe Leu Asn
                165                 170             175

His Asn Asp Gln Thr Thr Thr Trp Gln Asp Pro Arg Lys Ala Met Leu
                180                 185             190

Ser Gln Leu Asn Val Pro Ala Pro Ala Ser Pro Ala Val Pro Gln Thr
                195                 200             205

Leu Met Asn Ser Ala Ser Gly Pro Leu Pro Asp Gly Trp Glu Gln Ala
                210                 215             220

Met Thr Gln Asp Gly Glu Val Tyr Tyr Ile Asn His Lys Asn Lys Thr
225                 230                 235                 240

Thr Ser Trp Leu Asp Pro Arg Leu Asp Pro Arg Phe Ala Met Asn Gln
                245                 250             255

Arg Ile Thr Gln Ser Ala Pro Val Lys Gln Pro Pro Pro Leu Ala Pro
                260                 265             270

Gln Ser Pro Gln Gly Gly Val Leu Gly Gly Ser Ser Asn Gln Gln
                275                 280             285

Gln Gln Ile Gln Leu Gln Gln Leu Gln Met Glu Lys Glu Arg Leu Arg
                290                 295             300

Leu Lys Gln Gln Glu Leu Phe Arg Gln Glu Leu Ala Leu Arg Ser Gln
305                 310                 315                 320

Leu Pro Thr Leu Glu Gln Asp Gly Gly Thr Pro Asn Ala Val Ser Ser
                325                 330             335

Pro Gly Met Ser Gln Glu Leu Arg Thr Met Thr Thr Asn Ser Ser Asp
                340                 345             350

Pro Phe Leu Asn Ser Gly Thr Tyr His Ser Arg Asp Glu Ser Thr Asp
                355                 360             365

Ser Gly Leu Ser Met Ser Ser Tyr Ser Ile Pro Arg Thr Pro Asp Asp
                370                 375             380

Phe Leu Asn Ser Val Asp Glu Met Asp Thr Gly Asp Thr Ile Ser Gln
385                 390                 395                 400

Ser Thr Leu Pro Ser Gln Gln Ser Arg Phe Pro Asp Tyr Leu Glu Ala
                405                 410             415

Leu Pro Gly Thr Asn Val Asp Leu Gly Thr Leu Glu Gly Asp Ala Met
                420                 425             430
```

Asn Ile Glu Gly Glu Glu Leu Met Pro Ser Leu Gln Glu Ala Leu Ser
        435                 440                 445

Ser Glu Ile Leu Asp Val Glu Ser Val Leu Ala Ala Thr Lys Leu Asp
    450                 455                 460

Lys Glu Ser Phe Leu Thr Trp Leu
465                 470

<210> SEQ ID NO 8
<211> LENGTH: 1419
<212> TYPE: DNA
<213> ORGANISM: Mus musculus
<220> FEATURE:
<221> NAME/KEY: misc_feature
<222> LOCATION: (1)..(1419)
<223> OTHER INFORMATION: Encodes the protein of SEQ ID NO:7

<400> SEQUENCE: 8

| | | | | |
|---|---|---|---|---|
| atggagcccg | cgcaacagcc | gccgcccag | ccggccccgc | aaggccccgc | gccgccgtcc | 60 |
| gtgtctccgg | ccgggacccc | cgcggccccg | cccgcacccc | cggccggcca | ccaggtcgtg | 120 |
| cacgtccgcg | gggactcgga | gaccgacttg | gaggcgctct | tcaatgccgt | catgaacccc | 180 |
| aagacggcca | acgtgcctca | gaccgtgccc | atgcggcttc | gcaagctgcc | cgactccttc | 240 |
| ttcaagccgc | ctgagcccaa | gtcccactcg | cgacaggcca | gtactgatgc | aggtactgcg | 300 |
| ggagctctga | ctccacagca | tgttcgagct | cactcctctc | cagcctccct | gcagctgggt | 360 |
| gccgtttctc | ctgggacact | cacagccagt | ggcgttgtct | ctggccctgc | cgctgccct | 420 |
| gcagctcagc | atctccggca | gtcctccttt | gagatccctg | atgatgtacc | actgccagca | 480 |
| ggctgggaga | tggccaagac | atcttctggt | caaagatact | tcttaaatca | aacgatcag | 540 |
| acaacaacat | ggcaggaccc | ccggaaggcc | atgctttcgc | aactgaacgt | tcctgcgcct | 600 |
| gccagcccag | cggtgcccca | gacgctgatg | aattctgcct | caggacctct | tcctgatgga | 660 |
| tgggagcaag | ccatgactca | ggatggagaa | gtttactaca | taaaccataa | gaacaagacc | 720 |
| acatcctggc | tggacccaag | gctggaccct | cgttttgcca | tgaaccagag | gatcactcag | 780 |
| agtgctccag | tgaagcagcc | cccaccttg | gctccccaga | gcccacaggg | aggcgtcctg | 840 |
| ggtggaggca | gttccaacca | gcagcagcaa | atacagctgc | agcagttaca | gatggagaag | 900 |
| gagagactgc | ggttgaaaca | acaggaatta | tttcggcagg | aattagctct | gcgcagccag | 960 |
| ttgcctacac | tggagcagga | tggagggact | ccgaatgcag | tgtcttctcc | tgggatgtct | 1020 |
| caggaattga | gaacaatgac | aaccaatagt | tccgatccct | tcttaacag | tggcacctat | 1080 |
| cactctcgag | atgagagcac | agacagcggc | ctcagcatga | gcagctacag | catccctcgg | 1140 |
| accccagacg | acttcctcaa | cagtgtggat | gaaatggata | caggagacac | catcagccaa | 1200 |
| agcaccctgc | cgtcacagca | gagccgcttc | cccgactacc | tggaagccct | ccctgggaca | 1260 |
| aatgtggacc | ttggcacact | ggaaggagat | gcaatgaaca | tagaagggga | ggagctgatg | 1320 |
| cccagtctgc | aggaagcgct | gagttccgaa | atcttggacg | tggagtctgt | gttggctgcc | 1380 |
| accaagctag | ataagaaag | ctttctcacg | tggttatag | | | 1419 |

<210> SEQ ID NO 9
<211> LENGTH: 448
<212> TYPE: PRT
<213> ORGANISM: Gallus gallus
<300> PUBLICATION INFORMATION:
<308> DATABASE ACCESSION NUMBER: GENBANK NP_990574
<309> DATABASE ENTRY DATE: 2005-07-08
<313> RELEVANT RESIDUES: (1)..(448)

<400> SEQUENCE: 9

```
Met Asp Pro Gly Gln Pro Gln Pro Gln Gln Pro Gln Ala Ala Gln
1               5                   10                  15

Pro Pro Ala Pro Gln Gln Ala Ala Pro Gln Pro Gly Ala Gly Ser
            20                  25                  30

Gly Ala Pro Gly Gly Ala Ala Gln Pro Pro Gly Ala Gly Pro Pro
            35                  40                  45

Ala Gly His Gln Ile Val His Val Arg Gly Asp Ser Glu Thr Asp Leu
            50                  55                  60

Glu Ala Leu Phe Asn Ala Val Met Asn Pro Lys Gly Ala Asn Val Pro
65                  70                  75                  80

His Thr Leu Pro Met Arg Leu Arg Lys Leu Pro Asp Ser Phe Phe Lys
                85                  90                  95

Pro Pro Glu Pro Lys Ala His Ser Arg Gln Ala Ser Thr Asp Ala Gly
            100                 105                 110

Thr Ala Gly Ala Leu Thr Pro Gln His Val Arg Ala His Ser Ser Pro
            115                 120                 125

Ala Ser Leu Gln Leu Gly Ala Val Ser Pro Gly Thr Leu Thr Pro Ser
130                 135                 140

Gly Val Val Thr Gly Pro Gly Ala Pro Ser Ser Gln His Leu Arg Gln
145                 150                 155                 160

Ser Ser Phe Glu Ile Pro Asp Asp Val Pro Leu Pro Pro Gly Trp Glu
                165                 170                 175

Met Ala Lys Thr Pro Ser Gly Gln Arg Tyr Phe Leu Asn His Ile Asp
            180                 185                 190

Gln Thr Thr Thr Trp Gln Asp Pro Arg Lys Ala Met Leu Ser Gln Met
            195                 200                 205

Asn Val Thr Ala Pro Thr Ser Pro Pro Val Gln Gln Asn Leu Met Asn
210                 215                 220

Ser Ala Ser Ala Met Asn Gln Arg Ile Ser Gln Ser Ala Pro Val Lys
225                 230                 235                 240

Gln Pro Pro Pro Leu Ala Pro Gln Ser Pro Gln Gly Gly Val Met Gly
                245                 250                 255

Gly Ser Ser Ser Asn Gln Gln Gln Gln Met Arg Leu Gln Gln Leu Gln
            260                 265                 270

Met Glu Lys Glu Arg Leu Arg Leu Lys His Gln Glu Leu Leu Arg Gln
            275                 280                 285

Glu Leu Ala Leu Arg Ser Gln Leu Pro Thr Met Glu Gln Asp Gly Gly
            290                 295                 300

Ser Gln Asn Pro Val Ser Ser Pro Gly Met Ser Gln Glu Leu Arg Thr
305                 310                 315                 320

Met Thr Thr Asn Ser Ser Asp Pro Phe Leu Asn Ser Gly Thr Tyr His
                325                 330                 335

Ser Arg Asp Glu Ser Thr Asp Ser Gly Leu Ser Met Ser Ser Tyr Ser
            340                 345                 350

Val Pro Arg Thr Pro Asp Asp Phe Leu Asn Ser Val Asp Glu Met Asp
            355                 360                 365

Thr Gly Asp Ser Ile Ser Gln Ser Asn Ile Pro Ser His Gln Asn Arg
            370                 375                 380

Phe Pro Asp Tyr Leu Glu Ala Ile Pro Gly Thr Asn Val Asp Leu Gly
385                 390                 395                 400

Thr Leu Glu Gly Asp Gly Met Asn Ile Glu Gly Glu Glu Leu Met Pro
```

|  |  | 405 |  |  | 410 |  |  |  | 415 |  |  |
|---|---|---|---|---|---|---|---|---|---|---|---|
| Ser | Leu | Gln | Glu | Ala | Leu | Ser | Ser | Asp | Ile | Leu | Asn | Asp | Met | Glu | Ser |
|  |  |  | 420 |  |  |  |  | 425 |  |  |  |  | 430 |  |  |

| Val | Leu | Ala | Ala | Thr | Lys | Pro | Asp | Lys | Glu | Ser | Phe | Leu | Thr | Trp | Leu |
|---|---|---|---|---|---|---|---|---|---|---|---|---|---|---|---|
|  |  |  |  | 435 |  |  |  | 440 |  |  |  | 445 |  |  |  |

<210> SEQ ID NO 10
<211> LENGTH: 1347
<212> TYPE: DNA
<213> ORGANISM: Gallus gallus
<220> FEATURE:
<221> NAME/KEY: misc_feature
<222> LOCATION: (1)..(1347)
<223> OTHER INFORMATION: Encodes the protein of SEQ ID NO:9

<400> SEQUENCE: 10

```
atggatcccg ggcagcctca gccgcagcag ccgccgcagg cggcgcagcc cccggccccg      60
cagcaggcgg ccccgcagcc cccgggcgcg gggtcgggag ctccgggagg cgccgcgcag     120
ccgccgggcg cggggccccc tccggcgggg caccagatcg tccatgtgcg gggcgactcc     180
gagaccgacc tggaggctct cttcaacgcc gtgatgaacc caagggcgc caacgtgccg      240
cacacgctgc ccatgcggct ccgcaagctg ccggactcct tcttcaagcc gcccgagccc     300
aaagctcact cccgccaggc cagcactgac gcagggacag caggagccct gacccctcag     360
catgttcgtg ctcattcctc tccagcatca ctgcagctgg gggccgtctc ccctgggacg     420
ctcacaccct ccggagtagt gaccggaccc ggagctccgt cttctcagca tctccgccag     480
tcttcatttg agatccctga tgatgtacct ctgccaccgg gctgggagat ggccaaaaca     540
ccatctggac agagatactt ccttaatcat attgatcaaa caacaacatg gcaagatccc     600
aggaaggcca tgctttccca gatgaacgtt acagctccca ccagtcctcc cgtgcaacag     660
aacttaatga actcagcatc agccatgaat cagcgcatca gccaaagtgc tccagtgaaa     720
cagccaccc ctctggctcc tcagagtccc caaggtggtg tcatgggtgg gagtagctcc     780
aatcagcaac aacagatgag acttcagcag ctacagatgg agaaggaaag gctgagactg     840
aagcatcaag aactgcttcg gcaggaattg gctctccgta gccagcttcc aacgatggaa     900
caagatggtg gatctcaaaa tcccgtatca tctcctggaa tgtctcagga actgaggact     960
atgactacaa atagttctga tccctttctt aacagtggaa catatcactc cagagatgaa    1020
agcacagata gcggacttag catgagcagt tacagcgtac ccagaacccc cgatgacttc    1080
ctgaacagtg ttgatgagat ggatacaggt gacagtatca gccaaagtaa cataccgtcc    1140
catcagaacc gattcccaga ctaccttgaa gccattccag ggacaaatgt ggaccttggg    1200
acactggaag gagatgggat gaatatagaa ggagaagaac tgatgccaag tctgcaagag    1260
gctttgagct ctgacatcct aaatgacatg gaatctgtct tggcagccac aagccagat    1320
aaagagagtt ttcttacttg gttatag                                       1347
```

METHODS

The present invention relates to treatment and diagnosis of patients with polycystic kidney disease (PKD).

PKD is reviewed in detail in Guay-Woodford (2003) Am J Physiol Renal Physiol 285, F1034-F1049. Renal tubular cysts develop in several inherited human disorders. Among these, the polycystic kidney diseases (PKD) are one of the leading causes of endstage renal disease in children and adults (Gabow, (1993) N Engl J Med 329, 332-342). Autosomal dominant polycystic kidney disease (ADPKD) occurs in 1:1,000 individuals, primarily as the result of mutations in one of two genes, PKD1 or PKD2 (Mochizuki et al (1996) Science 272, 1339-1342; The American PKD1 Consortium (1995) Hum Mol Genet 4, 575-582; The European Polycystic Kidney Disease Consortium (1994) Cell 77, 881-894; The International Polycystic Kidney Disease Consortium (1995) Cell 81, 289-298). Rarer forms include autosomal recessive PKD (ARPKD), resulting primarily from mutations in a single gene, PKHD1, glomerulo-cystic kidney disease (GCKD) and nephronophthisis with high mortality and morbidity in children.

The principal pathological manifestations in PKD involve 1) the formation of epithelial-lined cysts throughout the nephron in ADPKD and predominantly in the collecting duct in ARPKD; 2) alterations in cell polarity; and 3) changes in extracellular matrix composition. In addition to the renal cystic disease, ADPKD is associated with cyst formation in other epithelial organs, most notably the liver and pancreas, as well as connective tissue defects, such as intracranial aneurysms, aortic dissection, cardiac valve abnormalities, and abdominal wall hernias (Perrone et al (1997) Kidney Int 51, 2022-2036). In comparison, the ARPKD phenotype is expressed almost exclusively in the kidney and liver, with the latter lesion involving biliary dysgenesis and portal tract fibrosis (D'Agata et al (1994) Semin Liver Dis 14, 265-272).

Efforts to elucidate the mechanisms that underlie PKD pathogenesis have been greatly enhanced by studies in experimental systems, most notably murine (mouse and rat) models of PKD. Numerous mouse and rat PKD models have been described in which the mutant phenotypes closely resemble human PKD with respect to cyst morphology, cyst localization, and disease progression (reviewed in Gretz et al (1996) Nephrol Dial Transplant 11, 46-51; Schieren et al (1996) Nephrol Dial Transplant 11, 38-45). Some of these models are the result of spontaneous mutations, whereas others were engineered through chemical mutagenesis, transgenic technologies, or gene-specific targeting in mouse orthologs of human PKD genes. These murine models share common pathogenic features with human PKD. These include 1) dysregulated epithelial cell proliferation and differentiation; 2) alterations of tubular basement membrane constituents and the associated extracellular matrix; 3) abnormalities of epithelial cell polarity with apical mislocalization of key receptors and enzymes; and 4) abnormalities in transepithelial fluid transport (reviewed Calvet and Grantham (2001) Semin Nephrol 21, 107-123). These parallel observations in murine models and human PKD prompt the hypothesis that mammalian PKD genes may define common molecular pathways that are involved in cytogenesis and PKD progression.

TAZ (transcriptional coactivator with PDZ-binding motif) is a recently described transcriptional coactivator factor with binding sites for 14-3-3 proteins, PDZ proteins and a WW domain (Kanai et al (2000) EMBO J 19, 6778-6791). TAZ is known to bind to 14-3-3, a conserved family of ~30-kDa proteins that bind to a large number of intracellular phosphoproteins involved in signal transduction to regulate differentiation, cell cycle progression, and apoptosis. TAZ has 395 amino acid residues, shares homology with YAP (Yes-associated protein), and contains a single WW domain. It functions as a transcriptional coactivator by binding to the PPXY motif present in targeted transcription factors (Kanai et al, supra). The C terminus of TAZ has the highly conserved PDZ-binding motif that helps localization of TAZ into discrete nuclear foci and is essential for TAZ-stimulated gene transcription. PDZ domains are present in a large number of proteins and proteins with PDZ domains may be membrane associated or in some instances end up in the nucleus. The binding of TAZ to 14-3-3 proteins can inhibit nuclear translocation of TAZ and thus inhibit the transcriptional coactivation function (Kanai et al, supra).

TAZ is a transcriptional coactivator that binds to the osteoblast-specific transcriptional factor Cbfa1 (Cui et al (2003) Mol Cell Biol 23, 1004-1013). TAZ has also been shown to act as a transcriptional coactivator of TTF-1, enhancing its transcriptional activity on the mouse surfactant protein C promoter (Park et al (2004) J Biol Chem 279, 17384-17390).

High-level expression of TAZ mRNA has been detected in the mouse heart, lung, liver, and kidney (Kanai et al, supra). However, the tissue distribution pattern for TAZ mRNA is slightly different in humans, where it was additionally found in the skeletal muscle, spleen, small intestine, and placenta (Kanai et al, supra).

Cui et al, supra, present data on the expression of TAZ protein in osteoblasts lining the developing bone and the presence of TAZ mRNA in 7-day-old mouse calvaria that is enriched in osteoblasts and argue that this demonstrates that TAZ is expressed in differentiating osteoblasts. The authors also argue that, since TAZ mRNA is also found in nonmineralizing tissues such as the heart, lung, liver, and muscle, TAZ may be either functional as a transcriptional coactivator on a more general level or it may be functioning at different capacities in these various tissues.

We have found that inactivation of the TAZ gene leads to a condition resembling human glomerulo-cystic kidney disease (GCKD) and nephronophthisis-medullary cystic kidney disease (NPH-MCKD). $TAZ^{-/-}$ mice have a decreased survival rate and, surprisingly, surviving animals develop kidney cysts at the corticomedullary border, most predominantly in the glomeruli. Thus, TAZ is not required for kidney development per se but plays a critical role in kidney physiology.

NPH-MCKD has been defined as a group of renal cystic diseases based on common features, including clinical symptoms, macroscopic pathology and renal histology (Hildebrandt, F., and Omram, H. (2001). New insights: nephronophthisis-dedullary cystic kidney disease. Pediatr Nephrol 16, 168-176). Characteristic for NPH-MCKD is the development of renal cysts at the corticomedullary border, which is quite distinct from autosomal dominant and recessive polycystic kidney disease (ADPKD, ARPKD), where cysts are distributed uniformly over the entire organ. Although four genes have been linked to NPH (Hildebrandt et al (1997). Nat Genet 17, 149-153; Otto et al (2002). Am J. Hum Genet 71, 1161-1167; Otto et al (2003) Nat Genet 34, 413-420; Olbrich et al (2003) Nat Genet 34, 455-459; Mollet et al (2002) Nat Genet. 32, 300-305), they account for less than 25% of known cases (Dr. F. Hildebrandt, personal communication). GCKD is characterized by cysts derived from glomeruli, a feature sometimes observed in NPH-MCKD.

The involvement of TAZ in PKD had not been contemplated before the present disclosure. Moreover, as mentioned above TAZ has a broad profile of expression and coactivates transcription factors involved in diverse processes. It is surprising, therefore, that TAZ$^{-/-}$ mice exhibit such a specific phenotype.

TAZ$^{-/-}$ mice animals can be used as disease models in which to study PKD progression and to aid in identifying agents which may be useful as a therapeutic entity. In contrast to previously described PKD model animals, some TAZ$^{-/-}$ mice survive to adulthood providing an opportunity to determine the effect of test therapeutic compounds over a greater lifespan; this is an important advantage of the present invention over the prior known models.

A first aspect of the invention provides a non-human animal which has a reduced amount of functional TAZ polypeptide and/or TAZ-like polypeptide, or a reduced amount of nucleic acid encoding said polypeptide.

Non-human animals having a reduced amount of functional TAZ polypeptide and/or TAZ-like polypeptide can be used as disease models in which to study PKD progression and to aid in identifying agents which may be useful as a therapeutic entity.

As mentioned above, PKD is a term for a range of disorders in which renal cysts develop. The non-human animals provided by the first aspect of the invention may be of use as model animals in which to study these disorders. Hence an embodiment of this aspect of the invention is wherein the non-human animal develops PKD. By "PKD" we include, in all aspects of the invention, all disorders that develop kidney cysts, including autosomal dominant polycystic kidney disease, autosomal recessive PKD, GCKD and nephronophthisis including NPH-MCKD. Preferably, in all aspects of the invention, we mean GCKD and NPH-MCKD.

By "reduced amount of functional" we include that, in comparison to a normal animal of the same species or strain, the animal of the first aspect of the invention has a reduced amount of polypeptide and/or less of the polypeptide can function in the way that the same polypeptide operates in the comparative animal, or a reduced amount of nucleic acid encoding TAZ polypeptide and/or TAZ-like polypeptide. For example, the animal of this aspect of the invention may have the same amount of polypeptide per se, but a greater proportion of the polypeptide is in a non-functional state. Methods of determining the amount of functional polypeptide or the amount of nucleic acid are provided below. Preferably, "reduced amount of functional" includes 50%, 25%, 10%, 5%, 1%, 0.1% or 0% of the amount of functional polypeptide or nucleic acid in the normal animal.

The non-human animal of the first aspect of the invention may have a reduced amount of functional TAZ polypeptide and/or TAZ-like polypeptide due to an agent which can modify the said polypeptide(s) function being supplied to the animal, for example a compound which acts to prevent polypeptide function or sub-cellular localisation, or a peptide or antibody which can bind to the polypeptide and prevent function or sub-cellular localisation. The non-human animal of the first aspect of the invention may have a reduced amount of nucleic acid encoding TAZ polypeptide and/or TAZ-like polypeptide due to an agent which can cause or induce degradation of said nucleic acid, for example a ribozyme which can target the nucleic acid, or an antisense molecule which can bind to the nucleic acid. Examples of such agents discussed herein.

Alternatively, the animal may be genetically modified in such a manner as to reduce the amount of functional TAZ polypeptide and/or TAZ-like polypeptide, or the amount of nucleic acid encoding said polypeptide. Preferably, the animal is a genetically modified.

The term "genetically modified" is well known to those skilled in the art. The term includes animals having introduced native or foreign nucleic acid. The animal may have had a modification made to its genome or may have been supplied with a nucleic acid which can act without modifying the genome. We also include animals in which one or more native genes has/have been inactivated, as will be discussed further below.

In brief, the first aspect of the invention includes those non-human animals in which a gene encoding TAZ polypeptide and/or TAZ-like polypeptide has a point mutation causing a frame-shift in the coding region of said genes using, for example, chemical mutagens; deletions and/or insertions of the whole or a part of the coding and controlling regions of said gene using, for example, physical mutagens; "knockouts" in which the gene is deleted using, for example, homologous recombination; replacements in which regions of the gene is replaced with gene sequence encoding a different polypeptide sequence using, for example, homologous recombination; antisense regulation of gene expression.

The non-human animal may have a reduced amount of functional TAZ polypeptide and/or TAZ-like polypeptide or a reduced amount of nucleic acid encoding said polypeptide through out the entire animal. Alternatively, there may be a reduction in said polypeptide function or nucleic acid only in some organs or tissues of the animal, for example, kidney, heart, placenta, lung, calvaria, bone, skin and brain. Preferably, the reduction in amount of functional TAZ polypeptide and/or TAZ-like polypeptide or the reduction in the amount of nucleic acid encoding said polypeptide is localised to the kidney. Methods of locally reducing polypeptide function or reducing nucleic acid amounts are discussed below.

The first aspect of the invention includes non-human primates such as baboons, chimpanzees and gorillas, new and old world monkeys as well as other mammals such as cats, dogs, rodents, pigs or sheep, or other animals such as poultry, for example chickens, fish such as zebrafish, or amphibians such as frogs. A preferred embodiment of this aspect of the invention is wherein the animal is a rodent such as a mouse, rat, hamster, guinea pig or squirrel. Preferably the animal is mouse.

To date human TAZ and mouse TAZ polypeptides have been identified. The polypeptide and polynucleotide sequences of human and mouse TAZ are given in GenBank Accession Numbers NP_056287.1, NM_015472.3 CAC17733 and AJ299430, respectively, and are also provided in FIG. 3. By "TAZ polypeptide" we include the human and mouse TAZ polypeptides as well as further homologues, orthologues or paralogues of TAZ.

The human and mouse TAZ polypeptides have significant degrees of homology to YAP (Yes-associated protein; Kanai et al, supra) polypeptides. To date human, mouse and chicken YAP polypeptides have been identified. The polypeptide and polynucleotide sequences of human, mouse and chicken YAP are given in GenBank Accession Numbers NP_006097, NM_006106, AAH39125, BC039125, NP_990574 and NM_205243, respectively, and are also provided in FIG. 4. By "TAZ-like polypeptide" we include the human, mouse and chicken YAP polypeptides as well as further homologues, orthologues or paralogues of these polypeptides having at least 50% identity to TAZ, preferably at least 60%, at least 70%, at least 80%, at least 90% or at least 95% sequence identity to the polypeptide sequence of TAZ.

Methods by which homologues, orthologues or paralogues of polypeptides can be identified are well known to those skilled in the art: for example, in silico screening or database mining. Preferably, such polypeptides have at least 40% sequence identity, preferably at least 60%, at least 70%, at least 80%, at least 90% or at least 95% sequence identity to the polypeptide sequence of TAZ or TAZ-like polypeptide.

Methods of determining the percent sequence identity between two polypeptides are well known in the art. For example, the percent sequence identity between two polypeptides may be determined using suitable computer programs, for example the GAP program of the University of Wisconsin Genetic Computing Group and it will be appreciated that percent identity is calculated in relation to polypeptides whose sequence has been aligned optimally.

The alignment may alternatively be carried out using the Clustal W program (Thompson et al., (1994) *Nucleic Acids Res* 22, 4673-80). The parameters used may be as follows:

Fast pairwise alignment parameters: K-tuple (word) size; 1, window size; 5, gap penalty; 3, number of top diagonals; 5. Scoring method: x percent.

Multiple alignment parameters: gap open penalty; 10, gap extension penalty; 0.05.

Scoring matrix: BLOSUM.

The term "nucleic acid encoding TAZ or TAZ-like polypeptide" includes both DNA and RNA molecules, including mRNA. By encode we mean that the sequence of bases in the nucleic acid molecule is such that, on transcription and/or translation, it encodes a polypeptide having the sequence of a TAZ or TAZ-like polypeptide. The term also includes single-stranded or double-stranded molecules, or those nucleic acids that are the complement of nucleic acids encoding said polypeptide, as would be appreciated by those skilled in the art. Therefore, we include in this term all nucleic acid molecules that encode a TAZ or TAZ-like polypeptide as defined above, including homologues, orthologues and paralogues as identified from the in silico screening and database mining methods discussed above.

A preferred embodiment of the first aspect of the invention is wherein the non-human animal has a reduced amount of functional native TAZ polypeptide or a reduced amount of nucleic acid encoding said polypeptide. By "native" we mean that TAZ polypeptide or nucleic acid is encoded by a gene native to the animal.

An alternative embodiment of the first aspect of the invention is wherein the non-human animal has a reduced amount of functional native TAZ-like polypeptide, preferably YAP polypeptide, or a reduced amount of nucleic acid encoding said polypeptide. By "native" we mean that YAP polypeptide or nucleic acid is encoded by a gene native to the animal.

A further alternative embodiment of the first aspect of the invention is wherein the non-human animal has a reduced amount of functional native TAZ and a reduced amount of functional native YAP polypeptide or a reduced amount of nucleic acid encoding said polypeptides.

A further alternative embodiment of the first aspect of the invention is wherein the non-human animal has no functional TAZ polypeptide or no nucleic acid encoding said polypeptide.

A second aspect of the invention provides a method for generating a non-human animal which develops PKD comprising reducing the amount of functional TAZ polypeptide and/or TAZ-like polypeptide, or reducing the amount of nucleic acid encoding said polypeptide.

Non-human animals having a reduced amount of functional TAZ polypeptide and/or TAZ-like polypeptide or a nucleic acid encoding said polypeptide, can be used as disease models in which to study PKD progression and to aid in identifying agents which may be useful as a therapeutic entity.

There are a number of different methods that can be employed to generate a non-human animal according to the first aspect of the invention. These will be discussed in turn below. Preferred methods include those in which the gene encoding the said polypeptide is altered or removed so as to produce little or none of said polypeptide. Other methods include inhibiting the transcription of the said gene or preventing any mRNA encoded by said gene from being translated.

"Homologous recombination" is a technique well known to those skilled in the art. Animals in which an endogenous gene has been inactivated by homologous recombination are referred to as "knockout" animals. Knockout animals, preferably non-human mammals, can be prepared as described in U.S. Pat. No. 5,557,032, incorporated herein by reference. Hence this aspect of the invention includes wherein the amount of functional TAZ polypeptide and/or a TAZ-like polypeptide is reduced by mutated one or more gene(s) encoding TAZ and/or TAZ-like polypeptide by homologous recombination. As a result the animal will no longer be able to synthesise TAZ and/or TAZ-like polypeptide, i.e. there will be a reduction in the amount of this polypeptide(s). This can also lead to a reduction in the amount of nucleic acid encoding said polypeptide. An example of the use of this method of the invention is provided in the accompanying examples.

FLP/FRT and CRE/LOX recombination systems can also be used to mutate one or more gene(s) encoding TAZ and/or TAZ-like polypeptide, as would be appreciated by a person skilled in the art.

Homologous recombination can be used to modify specific regions of a gene(s) encoding TAZ and/or TAZ-like polypeptide. For example, an introduced TAZ gene lacking certain protein motifs, for example the WW or PDZ motif, may replace a native gene encoding TAZ. Such a method that would generate a non-human animal that has reduced levels of functional TAZ and/or TAZ-like polypeptide is also included in this aspect of the invention.

Homologous recombination can be used to generate a non-human animal in which the amount of functional TAZ polypeptide and/or TAZ-like polypeptide is reduced only in certain cell types, i.e. tissue- or cell-specific knockout, for example a kidney-specific knockout. This can be achieved by introducing a gene encoding a TAZ polypeptide and/or TAZ-like polypeptide which is only expressed in certain cells or tissues using a cell- or tissue-specific promoter element, for example a promoter element not expressed in the kidney or using CRE/LOX recombination system.

"Insertional mutagenesis" is also a term well known to those skilled in the art. Examples of such mutagenesis include transposon-tagging, homing endonuclease genes (HEGs). In such methods a region of DNA is introduced into a gene such that the controlling or coding region of the gene is disrupted. Practical methods of using insertional mutagenesis in animals are well known to those skilled in the art. Hence a further embodiment of this aspect of the invention is wherein the amount of functional TAZ polypeptide and/or a TAZ-like polypeptide is reduced by mutated one or more gene(s) encoding TAZ and/or TAZ-like polypeptide by insertional mutagenesis. As a result the animal will no longer be able to synthesise TAZ and/or TAZ-like polypeptide, i.e. there will be a reduction in the amount of this polypeptide(s). This can also lead to a reduction in the amount of nucleic acid encoding said polypeptide.

Chemical or physical mutagenesis can also be used in the method of this aspect of the invention. Here, a gene is mutated by exposing the genome to a chemical mutagen, for example ethyl methylsulphate (EMS) or ethyl mitrosourea (ENU), or a physical mutagen, for example X-rays. Such agents act to alter the polynucleotide sequence of a gene or, in the case of some physical mutagens, can rearrange the order of sequences in a gene. Practical methods of using chemical or physical mutagenesis in animals are well known to those skilled in the art. Hence a further embodiment of this aspect of the invention is wherein the amount of functional TAZ polypeptide and/or a TAZ-like polypeptide is reduced by mutated one or more gene(s) encoding TAZ and/or TAZ-like polypeptide by chemical or physical mutagenesis. As a result the animal will no longer be able to synthesise TAZ and/or TAZ-like polypeptide, i.e. there will be a reduction in the amount of this polypeptide(s). This can also lead to a reduction in the amount of nucleic acid encoding said polypeptide.

Homologous recombination, insertional mutagenesis and chemical or physical mutagenesis can be used in the method of the second aspect of the invention to generate a non-human animal which is heterozygous for the target gene, e.g. $TAZ^{+/-}$. Such animals may be of particular use if the method of the second aspect of the invention generates a non-human animal having too severe a phenotype. As set out above, $TAZ^{-/-}$ mice develop PKD and can be used as disease models in which to study PKD progression and to aid in identifying agents which may be useful as a therapeutic entity.

Antisense oligonucleotides are single-stranded nucleic acids, which can specifically bind to a complementary nucleic acid sequence. By binding to the appropriate target sequence, an RNA-RNA, a DNA-DNA, or RNA-DNA duplex is formed. These nucleic acids are often termed "antisense" because they are complementary to the sense or coding strand of the gene. Recently, formation of a triple helix has proven possible where the oligonucleotide is bound to a DNA duplex. It was found that oligonucleotides could recognise sequences in the major groove of the DNA double helix. A triple helix was formed thereby. This suggests that it is possible to synthesise a sequence-specific molecules which specifically bind double-stranded DNA via recognition of major groove hydrogen binding sites.

By binding to the target nucleic acid, the above oligonucleotides can inhibit the function of the target nucleic acid. This could, for example, be a result of blocking the transcription, processing, poly(A)addition, replication, translation, or promoting inhibitory mechanisms of the cells, such as promoting RNA degradations.

Antisense oligonucleotides are prepared in the laboratory and then introduced into cells, for example by microinjection or uptake from the cell culture medium into the cells, or they are expressed in cells after transfection with plasmids or retroviruses or other vectors carrying an antisense gene. Antisense oligonucleotides were first discovered to inhibit viral replication or expression in cell culture for Rous sarcoma virus, vesicular stomatitis virus, herpes simplex virus type 1, simian virus and influenza virus. Since then, inhibition of mRNA translation by antisense oligonucleotides has been studied extensively in cell-free systems including rabbit reticulocyte lysates and wheat germ extracts. Inhibition of viral function by antisense oligonucleotides has been demonstrated in vitro using oligonucleotides which were complementary to the AIDS HIV retrovirus RNA (Goodchild, J. 1988 "Inhibition of Human Immunodeficiency Virus Replication by Antisense Oligodeoxynucleotides", *Proc. Natl. Acad. Sci.* (*USA*) 85(15), 5507-11). The Goodchild study showed that oligonucleotides that were most effective were complementary to the poly(A) signal; also effective were those targeted at the 5N end of the RNA, particularly the cap and 5N untranslated region, next to the primer binding site and at the primer binding site. The cap, 5N untranslated region, and poly(A) signal lie within the sequence repeated at the ends of retrovirus RNA (R region) and the oligonucleotides complementary to these may bind twice to the RNA.

Typically, antisense oligonucleotides are 15 to 35 bases in length. For example, 20-mer oligonucleotides have been shown to inhibit the expression of the epidermal growth factor receptor mRNA (Witters et al, *Breast Cancer Res Treat* 53:41-50 (1999)) and 25-mer oligonucleotides have been shown to decrease the expression of adrenocorticotropic hormone by greater than 90% (Frankel et al, *J Neurosurg* 91:261-7 (1999)). However, it is appreciated that it may be desirable to use oligonucleotides with lengths outside this range, for example 10, 11, 12, 13, or 14 bases, or 36, 37, 38, 39 or 40 bases.

By "antisense" we also include all methods of RNA interference, which are regarded for the purposes of this invention as a type of antisense technology.

Therefore, a further embodiment of this aspect of the invention is wherein the amount of nucleic acid encoding TAZ polypeptide and/or TAZ-like polypeptide is reduced using antisense. As a result the animal will no longer be able to synthesise TAZ and/or TAZ-like polypeptide, i.e. there will be a reduction in the amount of said polypeptide(s). This can also lead to a reduction in the amount of nucleic acid encoding said polypeptide.

Antisense can also be used to generate a non-human animal in which the amount of functional TAZ polypeptide and/or TAZ-like polypeptide is reduced only in certain cell types, i.e. a tissue- or cell-specific knockout, for example a kidney-specific knockout. This can be achieved by preparing the oligonucleotides in the laboratory and then introducing them into specific cells, for example by microinjection or implanting them using liposomes, microcapsules or implantable devices, for example into the kidney. Alternatively, it is possible to generate tissue- or cell-specific knockouts by expressing antisense oligonucleotides in specific cells after transfection with plasmids or retroviruses or other vectors carrying an antisense gene which is only expressed in specific cells or tissues using a cell- or tissue-specific promoter element, for example a kidney cell-specific promoter element, or a regulatable promoter, as would be appreciated by a person skilled in the art.

It will be appreciated that antisense agents also include larger molecules which bind to mRNA or genes encoding TAZ polypeptide and/or TAZ-like polypeptide and substantially prevent expression of said mRNA or genes. Thus, expression of such an antisense molecule which is substantially complementary to nucleic acid encoding TAZ polypeptide and/or TAZ-like polypeptide and is envisaged as part of the invention.

The said larger molecules may be expressed from any suitable genetic construct as is described below and delivered to the patient. Typically, the genetic construct which expresses the antisense molecule comprises at least a portion of the cDNA or gene encoding the TAZ polypeptide and/or TAZ-like polypeptide, operatively linked to a promoter which can express the antisense molecule in the cell.

In a further embodiment of this aspect of the invention is wherein the amount of nucleic acid encoding TAZ polypeptide and/or a TAZ-like polypeptide is reduced by supplying the animal with a ribozyme capable of cleaving RNA or DNA encoding TAZ polypeptide and/or TAZ-like polypeptide. A gene expressing said ribozyme may be administered in substantially the same and using substantially the same vehicles as for antisense molecules.

Ribozymes which may be encoded in the genomes of the viruses or virus-like particles herein disclosed are described in Cech and Herschlag "Site-specific cleavage of single stranded DNA" U.S. Pat. No. 5,180,818; Altman et al "Cleavage of targeted RNA by RNAse P" U.S. Pat. No. 5,168,053; Cantin et al "Ribozyme cleavage of HIV-1 RNA" U.S. Pat. No. 5,149,796; Cech et al "RNA ribozyme restriction endoribonucleases and methods", U.S. Pat. No. 5,116,742; Been et al "RNA ribozyme polymerases, dephosphorylases, restriction endonucleases and methods", U.S. Pat. No. 5,093,246; and Been et al "RNA ribozyme polymerases, dephosphorylases, restriction endoribonucleases and methods; cleaves single-stranded RNA at specific site by transesterification", U.S. Pat. No. 4,987,071, all incorporated herein by reference.

It will be appreciated that it may be desirable that the antisense molecule or ribozyme is expressed from a cell-specific promoter element, or a regulatable promoter.

The genetic constructs of the invention can be prepared using methods well known in the art.

A further method for reducing the amount of functional TAZ polypeptide and/or a TAZ-like polypeptide in a non-human animal is by supplying the animal with one or more agents that act as an antagonist of TAZ and/or a TAZ-like polypeptide.

The term "antagonist" is well known to those skilled in the art. By "antagonist" we include any agent that acts to reduce the level of functional TAZ polypeptide and/or a TAZ-like polypeptide. An example of such an antagonist is an antibody, or antibody fragment, that binds to one of the said polypeptides such that the polypeptide cannot effect its normal function. The antagonist may also alter the sub-cellular localisation of TAZ or TAZ-like polypeptide. In this way, the level of functional polypeptide is reduced. The antagonist may act to affect the function of the WW or PDZ motifs present in TAZ polypeptide and/or a TAZ-like polypeptide thus modifying the polypeptide's capacity to function as a transcriptional coactivator.

The antagonist may be used to generate a tissue- or cell-specific knockout, for example a kidney-specific knockout, of TAZ polypeptide and/or a TAZ-like polypeptide function. For example, where the antagonist is an antibody, or antibody fragment, that binds to one of the said polypeptides such that the polypeptide cannot effect a normal function or alter its sub-cellular localisation, then a gene encoding said antagonist may be regulated using a tissue- or cell-specific promoter, for example a kidney-specific promoter.

Further methods of use in this aspect of the invention include wherein the amount of nucleic acid encoding TAZ polypeptide and/or a TAZ-like polypeptide is reduced by modifying the chromatin structure at or adjacent to gene(s) encoding a TAZ polypeptide and/or a TAZ-like polypeptide. This may be achieved using, for example, targeted DNA methylation. Such methods are known to those skilled in the art.

Further methods of use in this aspect of the invention include wherein the amount of functional TAZ polypeptide and/or a TAZ-like polypeptide is reduced by modifying the function of an upstream regulator of TAZ polypeptide and/or a TAZ-like polypeptide. For example, phosphorylation by Ser/Thr kinase(s) is required for TAZ to interact with 14-3-3 proteins (Kanai et al, supra). Therefore, modifying the function of an endogenous Ser/Thr kinase, preferably a kidney-specific kinase, would lead to a reduction in the amount of functional TAZ polypeptide and/or TAZ-like polypeptide.

Further methods of use in this aspect of the invention include wherein the amount of functional TAZ polypeptide and/or a TAZ-like polypeptide is reduced by supplying the animal with a dominant inactive form of a TAZ and/or a TAZ-like polypeptide. For example a polypeptide may be modified so as to generate a dominant inactive form of a TAZ polypeptide or a TAZ-like polypeptide that can bind to the same binding sites as TAZ or TAZ-like polypeptides but cannot effect the same function as TAZ polypeptide and/or a TAZ-like polypeptide. Alternatively the dominant inactive form may be mislocalised within the cell. Hence overexpression of a dominant inactive form of a TAZ polypeptide and/or a TAZ-like polypeptide in a non-human animal may act to block the function of the native TAZ polypeptide or TAZ-like polypeptide.

A third aspect of the invention provides a method for generating a non-human animal which develops PKD comprising:

i) identifying a polypeptide regulated by TAZ or a TAZ-like polypeptide, or a nucleic acid encoding said polypeptide;

ii) generating a non-human animal which has a reduced amount of the polypeptide and/or nucleic acid identified in step i); and optionally, iii) selecting a non-human animal generated by step ii) which develops PKD.

The first step of the method of the third aspect of the invention identifies a polypeptide regulated by TAZ or a TAZ-like polypeptide, or a nucleic acid encoding said polypeptide.

TAZ and TAZ-like polypeptides can regulate polypeptides in two ways.

Firstly, TAZ and TAZ-like polypeptides can directly act to regulate the function of further polypeptides, for example Cbfa1 and TTF1 as mentioned below. Further examples of polypeptides included with the scope of the term "polypeptide regulated by TAZ or TAZ-like polypeptide" may be found by, for example, a yeast two-hybrid library screen using a TAZ or TAZ-like polypeptide or a fragment or variant thereof, as a bait, as would be appreciated by those skilled in the art.

Secondly, TAZ and TAZ-like polypeptides can indirectly act to regulate the function of further polypeptides. For example, TAZ can interact with TTF1 to regulate the expression of surfactant protein C (Park et al, supra). Further examples of polypeptides included with the scope of the term "polypeptide regulated by TAZ or TAZ-like polypeptide" may be found by, for example, conducting a proteomic or transcriptional microarray analysis of normal tissue and tissue having a reduced amount of functional TAZ or TAZ-like polypeptide, and identifying those polypeptides or transcripts which are present in different amounts, as would be appreciated by those skilled in the art. Methods to identify such polypeptides are provided in example 2.

A transcriptional microarray analysis of normal tissue and tissue having a reduced amount of functional TAZ or TAZ-like polypeptide is presented in example 3. Here it is demonstrated that the expression of several genes (e.g. Rpgrip1, Hif1a, Ctss, Pcm1, Dctn3, Dctn5, Kif5b and Nisch) that encode proteins that either localize to cilia (Rpgrip, Hif1a, Pcm1, Dctn3, Dctn5), or are associated with the structure and/or function of cilia (Pcm1, Ctss, Dctn3, Dctn5) and/or microtubules (Dctn3, Dctn5, Kif5b), are downregulated by greater than two fold in $TAZ^{-/-}$ kidneys. Accordingly, the term "polypeptide regulated by TAZ or TAZ-like polypeptide" includes the polypeptides encoded by Rpgrip1, Hif1a, Ctss, Pcm1, Dctn3, Dctn5, Kif5b and Nisch and further genes shown by example 3 to be differentially expressed in tissue having a reduced amount of functional TAZ or TAZ-like polypeptide.

Furthermore, as discussed in example 3, RT-PCR and real time PCR was used to analyse the expression of the gene product of OFD1 (the gene mutated in oral-facial-digital syndrome). OFD1 mutations are accompanied by glomerular cysts (GCKD) (Ferrante et al (2003). Genomics 81, 560-569; Ferrante et al (2001) Am J Hum Genet 68, 569-576; Romio et al (2003) J Am Soc Nephrol 14, 680-689). OFD1 expression is reduced to ~60% of normal in E 17.5 kidneys of TAZ$^{-/-}$ mice. Accordingly, the term "polypeptide regulated by TAZ or TAZ-like polypeptide" includes the polypeptide encoded by OFD1.

Further methods of identifying polypeptides regulated by TAZ or TAZ-like polypeptide include "pull down" assays in which the TAZ polypeptide is fused to a GST tag; the tagged polypeptide is bound to glutathione beads; the tagged polypeptide is then incubated with a sample of further polypeptides; any polypeptides that interact with TAZ or TAZ-like polypeptide are then isolated from the beads and identified using mass spectrometry. Alternatively, the "pull down" assay can use an antibody to isolate any polypeptides that interact with TAZ or TAZ-like polypeptide by precipitating the TAZ/polypeptide complex.

A further method of identifying polypeptides regulated by TAZ or TAZ-like polypeptide is wherein nucleic acid encoding TAZ is transcribed and translated in the presence of one or more cDNAs that encode further polypeptides. By assaying the amount or function of TAZ it is possible to determine whether the further polypeptide can be considered to interact with TAZ.

The hepatocyte nuclear factor-1beta (HNF-1b) transcription factor gene encodes a polypeptide having a PPXY motif, and so hepatocyte nuclear factor-1beta (HNF-1b) may interact with TAZ. Interestingly, HNF-1b has been linked to PKD (reviewed in Bingham, C. and Hattersaly, A. T. 2004. Nephrol. Dial. Transplant 19:2708). Recently, a transcriptional network in PKD has been revealed by the conditional inactivation of Hnf1, where cyst formation was accompanied by a defect in transcriptional activation of Umod, Pkhd1 and Pkd and polaris (Gresh et al (2004) EMBO J 23, 1657-1668). Therefore the term "polypeptide regulated by TAZ or TAZ-like polypeptide" includes HNF-1b.

As mentioned above, TAZ acts as a coactivator to regulate the function of further polypeptides, for example transcription factors. Hence it is likely that the PKD phenotype of TAZ$^{-/-}$ results from TAZ failing to activate the function of a polypeptide or nucleic acid regulated by TAZ. For example, Kanai et al, supra disclose that TAZ functions as a transcriptional coactivator of Runx transcription factors. The Runx2 gene (also known as Cbfla) is expressed in the kidney and therefore may in part mediate the PKD phenotype of TAZ$^{-/-}$ mice. TAZ also interacts with thyroid transcription factor 1 (TTF1, also called Nkx2.1). Kanai et al, supra speculate that transcription factors having a PPXY motif, for example c-Jun, AP-2, C/EBPα, NF-E2, KROZ-20, KROX-24, Oct-4, MEF2B and the p53 homologue p73. Therefore the term "polypeptide regulated by TAZ or TAZ-like polypeptide" includes those mentioned above.

Preferably, a "polypeptide regulated by TAZ or TAZ-like polypeptide" is Runx2 (Cbf1a) or TTF1 (Nkx2.1).

The second step of the method of the third aspect of the invention generates a non-human animal which has a reduced amount of the polypeptide and/or nucleic acid identified in the first step.

Methods of generating an animal having a reduced amount of a polypeptide, or a nucleic acid encoding said polypeptide, are discussed above in relation to the second aspect of the invention. For example, it is possible to use homologous recombination, insertional mutagenesis or chemical or physical mutagens to disrupt the nucleic acid sequence encoding the polypeptide identified in the first step of this aspect of the invention. Further methods included in this aspect of the invention include antisense, supplying the animal with an antagonist of the identified polypeptide, modifying the chromatin structure at or adjacent to the gene encoding the identified polypeptide, modifying the function of an upstream regulator of the identified polypeptide, or supplying a non-human animal with a dominant inactive form of the identified polypeptide.

A final optional step in the third method of the third aspect of the invention involves selecting a non-human animal generated by step ii) which develops PKD.

PKD is commonly associated with multiple cysts locates in the kidney.

Hence one method of selecting whether a non-human animal generated by step ii) develops PKD is to examine the kidney of a test animal and compare the amount, location or physiology of cysts to a reference animal, i.e. an animal which does not have a reduced amount of the polypeptide and/or nucleic acid identified in step i). PKD progression can also be measured by ultrasound analysis or the use of a blood test that measures creatinine, urea and nitrogen levels, all of which are characteristically high in animals with PKD.

A fourth aspect of the invention provides a non-human animal obtained or obtainable from the method of the third aspect of the invention.

A fifth aspect of the invention provides a method of screening for compounds of use in preventing or treating PKD wherein a non-human animal is administered a test compound and the effect of the test compound on the amount or function of TAZ polypeptide and/or a TAZ-like polypeptide and/or a polypeptide regulated by TAZ or a TAZ-like polypeptide function, or the amount of nucleic acid encoding said polypeptide, is assessed.

An embodiment of the fifth aspect of the invention is wherein the animal is a genetically modified non-human animal according to the first or fourth aspects of the invention.

A sixth aspect of the invention provides a method of screening for compounds of use in preventing or treating PKD wherein a cell having TAZ polypeptide and/or TAZ-like polypeptide and/or polypeptide regulated by TAZ function is treated with a test compound and the effect of the test compound on the amount or function of TAZ polypeptide and/or a TAZ-like polypeptide and/or a polypeptide regulated by TAZ or a TAZ-like polypeptide, or the amount of nucleic acid encoding said polypeptide, is assessed.

The fifth and sixth aspects of the invention relate to screening methods for drugs or lead compounds. This will be further discussed below. The test compounds used in the methods of these aspects of the invention may increase or decrease the amount or function of TAZ polypeptide and/or a TAZ-like polypeptide and/or a polypeptide regulated by TAZ or a TAZ-like polypeptide function, or the amount of nucleic acid encoding said polypeptide. An increase in such functions or levels is generally preferred as such test compounds may be of use for preventing or treating PKD.

However, the methods of the fifth and sixth aspects of the invention also include the purpose of identifying compounds that decrease the amount or function of TAZ polypeptide and/or a TAZ-like polypeptide and/or a polypeptide regulated by TAZ or a TAZ-like polypeptide function, or the amount of nucleic acid encoding said polypeptide. Such compounds may be of use for developing a model animal system having accelerated PKD or a cell-based assay having suppressed functions or levels of TAZ polypeptide and/or a TAZ-like polypeptide and/or a polypeptide regulated by TAZ or a TAZ-like polypeptide; such model animals or cell-based assays can be used to determine whether further test compounds, or other external stimuli, may be of use for preventing or treating PKD.

A seventh aspect of the invention provides a method of identifying a compound of use in preventing or treating PKD comprising:
   i) administering a test compound to a non-human animal;
   ii) assessing the effect of the test compound on the amount or function of TAZ polypeptide and/or a TAZ-like polypeptide and/or a polypeptide regulated by TAZ or a TAZ-like polypeptide, or the amount of a nucleic acid encoding said polypeptide; and,
   iii) selecting any compound that increases the amount or function of TAZ polypeptide and/or a TAZ-like polypeptide and/or a polypeptide regulated by TAZ or a TAZ-like polypeptide, or increases the amount of nucleic acid encoding said polypeptide.

An eighth aspect of the invention provides a method of identifying a compound of use in preventing or treating PKD comprising:
   i) administering a test compound to TAZ polypeptide and/or a TAZ-like polypeptide and/or a polypeptide regulated by TAZ or a TAZ-like polypeptide;
   ii) assessing the effect of the test compound on the function of TAZ polypeptide and/or a TAZ-like polypeptide and/or a polypeptide regulated by TAZ or a TAZ-like polypeptide function; and,
   iii) selecting any compound that increases the function of TAZ polypeptide and/or a TAZ-like polypeptide and/or a polypeptide regulated by TAZ or a TAZ-like polypeptide.

A ninth aspect of the invention provides a method of identifying a compound of use in preventing or treating PKD comprising:
   i) administering a test compound to cell comprising TAZ polypeptide and/or a TAZ-like polypeptide and/or a polypeptide regulated by TAZ or a TAZ-like polypeptide;
   ii) assessing the effect of the test compound on the amount or function of TAZ polypeptide and/or a TAZ-like polypeptide and/or a polypeptide regulated by TAZ or a TAZ-like polypeptide, or the amount of a nucleic acid encoding said polypeptide; and,
   iii) selecting any compound that increases the amount or function of TAZ polypeptide and/or a TAZ-like polypeptide and/or a polypeptide regulated by TAZ or a TAZ-like polypeptide, or the amount of a nucleic acid encoding said polypeptide.

The methods of the fifth, sixth, seventh, eighth and ninth aspects of the invention relate to screening methods for drugs or lead compounds.

The term "polypeptide regulated by TAZ or TAZ-like polypeptide" includes those polypeptide mentioned above in relation to the third aspect of the invention.

As would be understood by the skilled person, in the methods of the fifth, sixth, seventh, eighth and ninth aspects of the invention the terms "TAZ polypeptide", "TAZ-like polypeptide" and "a polypeptide regulated by TAZ or a TAZ-like polypeptide" also includes fragments and variants of these polypeptides.

A "fragment" of the TAZ polypeptide and/or TAZ-like polypeptide and/or polypeptide regulated by TAZ or TAZ-like polypeptide is one which may retain one or more activities of the full length polypeptide. For example, TAZ has a number of different protein motifs, e.g. the WW domain and the PDZ-binding motif. Hence a fragment comprising one or more of such domains isolated from the said polypeptide(s) can also be used in the fifth, sixth, seventh, eighth and ninth aspects of the invention.

A "variation" of the fragment of the polypeptide is one which may usable to prepare antibodies which specifically bind to the protein. Such a variant may be encoded by a gene in which different codons can be substituted which code for the same amino acid(s) as the original codons. Alternatively, the substitute codons may code for a different amino acid that will not affect the function or immunogenicity of the protein or which may improve its function or immunogenicity. For example, site-directed mutagenesis or other techniques can be employed to create single or multiple mutations, such as replacements, insertions, deletions, and transpositions, as described in Botstein and Shortle, "Strategies and Applications of In Vitro Mutagenesis," *Science,* 229: 193-1210 (1985), which is incorporated herein by reference.

It will be appreciated that in the methods fifth, sixth, seventh, eighth and ninth aspects of the invention, which may be drug screening methods, a term well known to those skilled in the art, the compound may be a drug-like compound or lead compound for the development of a drug-like compound.

The term "drug-like compound" is well known to those skilled in the art, and may include the meaning of a compound that has characteristics that may make it suitable for use in medicine, for example as the active ingredient in a medicament. Thus, for example, a drug-like compound may be a molecule that may be synthesised by the techniques of organic chemistry, less preferably by techniques of molecular biology or biochemistry, and is preferably a small molecule, which may be of less than 5000 daltons and which may be water-soluble. A drug-like compound may additionally exhibit features of selective interaction with a particular protein or proteins and be bioavailable and/or able to penetrate target cellular membranes, but it will be appreciated that these features are not essential.

The term "lead compound" is similarly well known to those skilled in the art, and may include the meaning that the compound, whilst not itself suitable for use as a drug (for example because it is only weakly potent against its intended target, non-selective in its action, unstable, poorly soluble, difficult to synthesise or has poor bioavailability) may provide a starting-point for the design of other compounds that may have more desirable characteristics.

The methods of the fifth, sixth, seventh, eighth and ninth aspects of the invention include a step of assessing the effect of a test compound on the amount or function of TAZ polypeptide and/or a TAZ-like polypeptide and/or a polypeptide regulated by TAZ or TAZ-like polypeptide, and the fifth, sixth, seventh and ninth aspects of the invention also include a step of assessing the effect of a test compound on the amount of nucleic acid encoding said polypeptide.

In common with all these methods is the need for a "reference sample", i.e. a sample of protein or nucleic acid taken from an animal or a cell or a test reaction which has not been exposed to the test compound. By comparing the amount or function of TAZ polypeptide and/or a TAZ-like polypeptide and/or a polypeptide regulated by TAZ or TAZ-like polypeptide, or the amount of nucleic acid encoding said polypeptide, in a sample of protein or nucleic acid taken from an animal or a cell or a test reaction which has not been exposed to the test compound, to the amount or function of TAZ polypeptide and/or a TAZ-like polypeptide and/or a polypeptide regulated by TAZ or TAZ-like polypeptide, or the amount of nucleic acid encoding said polypeptide, in a sample of protein or nucleic acid taken from an animal or a cell or a test reaction which has been exposed to the test compound it is possible to determine the effect of the test compound on the amount of function of TAZ polypeptide and/or a TAZ-like polypeptide and/or a polypeptide regulated by TAZ or TAZ-like polypeptide, or the amount of nucleic acid encoding said polypeptide. This will be either an elevation or reduction in the amount or function of the polypeptide or the amount of nucleic acid.

The step of assessing the amount or function of TAZ polypeptide and/or a TAZ-like polypeptide and/or a polypeptide regulated by TAZ or TAZ-like polypeptide, or the amount of nucleic acid encoding said polypeptide, may be performed using a number of different methods.

Firstly, the effect of the test compound in the fifth, sixth, seventh and ninth aspects of the invention can be determined by quantifying the amount of nucleic acid, preferably mRNA, encoding the TAZ polypeptide and/or a TAZ-like polypeptide and/or a polypeptide regulated by TAZ or TAZ-like polypeptide.

Levels of mRNA encoding the TAZ polypeptide and/or a TAZ-like polypeptide and/or a polypeptide regulated by TAZ or TAZ-like polypeptide may be assayed using the RT-PCR method described in Makino et al, Technique 2:295-301 (1990). By this method, the radioactivities of the "amplicons" in the polyacrylamide gel bands are linearly related to the initial concentration of the target mRNA. Briefly, this method involves adding total RNA isolated from a biological sample in a reaction mixture containing a RT primer and appropriate buffer. After incubating for primer annealing, the mixture can be supplemented with a RT buffer, dNTPs, DTT, RNase inhibitor and reverse transcriptase. After incubation to achieve reverse transcription of the RNA, the RT products are then subject to PCR using labeled primers. Alternatively, rather than labeling the primers, a labeled dNTP can be included in the PCR reaction mixture. PCR amplification can be performed in a DNA thermal cycler according to conventional techniques. After a suitable number of rounds to achieve amplification, the PCR reaction mixture is electrophoresed on a polyacrylamide gel. After drying the gel, the radioactivity of the appropriate bands (corresponding to the mRNA encoding the TAZ polypeptide and/or a TAZ-like polypeptide and/or a polypeptide regulated by TAZ or TAZ-like polypeptide) is quantified using an imaging analyzer. RT and PCR reaction ingredients and conditions, reagent and gel concentrations, and labeling methods are well known in the art. Variations on the RT-PCR method will be apparent to the skilled artisan. Any set of oligonucleotide primers which will amplify reverse transcribed target mRNA can be used and can be designed as will be well known to those skilled in the art.

Levels of mRNA encoding the TAZ polypeptide and/or a TAZ-like polypeptide and/or a polypeptide regulated by TAZ or a TAZ-like polypeptide can also be assayed using northern blotting, a method well known to those skilled in the art and described further in Sambrook et al., Molecular Cloning. A laboratory manual. 1989. Cold Spring Harbour publications.

Further methods which may be of use in measuring mRNA levels include in situ hybridisation (In Situ Hybridization Protocols. Methods in Molecular Biology Volume 33. Edited by K H A Choo. 1994, Humana Press Inc (Totowa, N.J., USA) pp 480p and In Situ Hybridization: A Practical Approach. Edited by D G Wilkinson. 1992, Oxford University Press, Oxford, pp 163), in situ amplification, nuclease protection, probe arrays, and amplification based systems.

A further method of assessing the effect of the test compound on TAZ polypeptide and/or a TAZ-like polypeptide and/or a polypeptide regulated by TAZ or a TAZ-like polypeptide in the fifth, sixth, seventh or ninth aspects of the invention is to quantify the amount of said polypeptide.

Assaying the amount of TAZ polypeptide and/or a TAZ-like polypeptide and/or a polypeptide regulated by TAZ or TAZ-like polypeptide in a biological sample can occur using any art-known method. Preferred for assaying TAZ polypeptide and/or a TAZ-like polypeptide and/or a polypeptide regulated by TAZ or TAZ-like polypeptide protein levels in a biological sample are antibody-based techniques. For example, TAZ polypeptide and/or a TAZ-like polypeptide and/or a polypeptide regulated by TAZ or TAZ-like polypeptide protein expression in tissues can be studied with classical immunohistological methods. In these, the specific recognition is provided by the primary antibody (polygonal or monoclonal) but the secondary detection system can utilize fluorescent, enzyme, or other conjugated secondary antibodies. As a result, an immunohistological staining of tissue section for pathological examination is obtained. Tissues can also be extracted, e.g., with urea and neutral detergent, for the liberation of TAZ polypeptide and/or a TAZ-like polypeptide and/or a polypeptide regulated by TAZ or TAZ-like polypeptide protein for Western-blot or dot/slot assay (Jalkanen, M., et al., J. Cell. Biol. 101:976-985 (1985); Jalkanen, M., et al., J. Cell. Biol. 105:3087-3096 (1987)). In this technique, which is based on the use of cationic solid phases, quantitation of TAZ polypeptide and/or a TAZ-like polypeptide and/or a polypeptide regulated by TAZ or TAZ-like polypeptide protein can be accomplished using isolated TAZ polypeptide and/or a TAZ-like polypeptide and/or a polypeptide regulated by TAZ or TAZ-like polypeptide protein as a standard. This technique can also be applied to animal fluids. With these samples, a molar concentration of TAZ polypeptide and/or a TAZ-like polypeptide and/or a polypeptide regulated by TAZ or TAZ-like polypeptide protein will aid to set standard values of TAZ polypeptide and/or a TAZ-like polypeptide and/or a polypeptide regulated by TAZ or TAZ-like polypeptide protein content for different animal fluids, like serum, plasma, urine, spinal fluid, etc. The normal appearance of TAZ polypeptide and/or a TAZ-like polypeptide and/or a polypeptide regulated by TAZ or TAZ-like polypeptide protein amounts can then be set using values from healthy individuals, which can be compared to those obtained from a test subject.

Other antibody-based methods useful for detecting TAZ polypeptide and/or a TAZ-like polypeptide and/or a polypeptide regulated by TAZ or TAZ-like polypeptide protein gene expression include immunoassays, such as the enzyme linked immunosorbent assay (ELISA) and the radioimmunoassay (RIA). For example, a TAZ polypeptide and/or a TAZ-like polypeptide and/or a polypeptide regulated by TAZ or TAZ-like polypeptide protein-specific monoclonal antibody can be used both as an immunoadsorbent and as an enzyme-labeled probe to detect and quantify the TAZ polypeptide and/or a TAZ-like polypeptide and/or a polypeptide regulated by TAZ or TAZ-like polypeptide protein. The amount of TAZ polypeptide and/or a TAZ-like polypeptide and/or a polypeptide regulated by TAZ or TAZ-like polypeptide protein present in the sample can be calculated by reference to the amount present in a standard preparation using a linear regression computer algorithm. Such an ELISA for detecting a tumor antigen is described in Iacobelli et al., Breast Cancer Research and Treatment 11: 19-30 (1988). In another ELISA assay, two distinct specific monoclonal antibodies can be used to detect TAZ polypeptide and/or a TAZ-like polypeptide and/or a polypeptide regulated by TAZ or TAZ-like polypeptide protein in a body fluid. In this assay, one of the antibodies is used as the immunoadsorbent and the other as the enzyme-labeled probe.

In addition to assaying TAZ polypeptide and/or a TAZ-like polypeptide and/or a polypeptide regulated by TAZ or TAZ-like polypeptide protein levels in a biological sample obtained from an animal or a cell, TAZ polypeptide and/or a TAZ-like polypeptide and/or a polypeptide regulated by TAZ or TAZ-like polypeptide protein can also be detected in vivo by imaging. Antibody labels or markers for in vivo imaging of TAZ polypeptide and/or a TAZ-like polypeptide and/or a polypeptide regulated by TAZ or TAZ-like polypeptide protein include those detectable by X-radiography, NMR or ESR. For X-radiography, suitable labels include radioisotopes such as barium or caesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

TAZ polypeptide and/or a TAZ-like polypeptide and/or a polypeptide regulated by TAZ or TAZ-like polypeptide protein-specific antibodies for use in the screening methods of the present invention can be raised against the intact TAZ polypeptide and/or a TAZ-like polypeptide and/or a polypeptide regulated by TAZ protein or TAZ-like polypeptide or an antigenic polypeptide fragment thereof, which may be presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody fragments (such as, for example, Fab and F(ab')2 fragments) which are capable of specifically binding to TAZ polypeptide and/or a TAZ-like polypeptide and/or a polypeptide regulated by TAZ protein. Fab and F(ab')2 fragments lack the Fc fragment of intact antibody, clear more rapidly from the circulation, and may have less non-specific tissue binding of an intact antibody (Wahl et al, J. Nucl. Med. 24:316-325 (1983)). Thus, these fragments are preferred.

A further method of assessing the effect of the test compound in the fifth, sixth, seventh, eighth and ninth aspects of the invention is to assess the effect of the test compound on the function of TAZ polypeptide and/or a TAZ-like polypeptide and/or a polypeptide regulated by TAZ or TAZ-like polypeptide.

As discussed above, TAZ acts as a transcriptional coactivator. Hence determining any change in the capacity of TAZ to act as a transcriptional coactivator can be used to assess the effect of a test compound on TAZ function.

An assay of TAZ function is presented in Kanai et al, supra. Here TAZ is fused to the minimum GAL4 DNA-binding domain and the effect of TAZ-GAL4 DBD on regulating the transcription of a reporter gene containing a GAL4 DNA-binding site is assessed. Such an assay may be of use in the screening methods of the invention. For example, in the sixth aspect of the invention the test compound may be administered to a TAZ polypeptide comprising a GAL4 DBD and the effect of the test compound on the capacity of the TAZ polypeptide to activate reporter gene expression assessed.

A reporter protein may be one whose activity may easily be assayed, for example β-galactosidase, chloramphenicol acetyltransferase or luciferase (see, for example, Tan et al (1996)). In a further example, the reporter gene may be fatal to the cells, or alternatively may allow cells to survive under otherwise fatal conditions. Cell survival can then be measured, for example using calorimetric assays for mitochondrial activity, such as reduction of WST-1 (Boehringer). WST-1 is a formosan dye that undergoes a change in absorbance on receiving electrons via succinate dehydrogenase.

TAZ polypeptide can also interact with further polypeptides to regulate gene expression. For example, in Cui et al supra an assay of TAZ function is disclosed in which TAZ is cotransformed into cells with a reporter gene construct (in this case luciferase) and a polypeptide which TAZ binds to effect transactivation (in this case Cbfa1); the level of reporter gene activity reflects TAZ function. Such an assay may be of use in the screening methods of the invention. For example, in the eighth aspect of the invention the test compound may be administered to a TAZ polypeptide and the effect of the test compound on the capacity of the TAZ polypeptide to activate reporter gene expression through Cbfa1 assessed.

Similar assays of use in the screening methods of the invention are also disclosed in Park et al supra.

TAZ and the TAZ-like polypeptide YAP participate in specific protein-protein interactions (Kanai et al, supra). Therefore, one assay of TAZ and TAZ-like function is to assess the effect of the test compound on the capacity of TAZ and TAZ-like polypeptide to participate in such interactions. Kanai et al, supra present assays in which TAZ and YAP bind to NHERF-2. Zaidi et al (2004) EMBO J 23, 790-799 present data showing that YAP interacts with Runx2. Such assays may be of use in the screening methods of the invention. For example, in the eighth aspect of the invention the test compound may be administered to a TAZ or TAZ-like polypeptide and the effect of the test compound on the capacity of the polypeptides to interact with NHERF-2 assessed. Further possible assays would be apparent to those skilled in the art.

A tenth aspect of the invention provides a method of identifying a compound of use in modulating PKD progression comprising:

i) administering a test compound to a non-human animal which develops PKD according to the first or fourth aspects of the invention;
ii) assessing the effect of the test compound on PKD; and,
iii) selecting any compound that modulates PKD progression in the animal.

The tenth aspect of the invention is also a screening method for drugs or lead compounds.

The methods of the tenth aspect of the invention may include a further step of assessing the effect of the test compound on PKD. Hence there is the need for a "reference sample", i.e. an animal which has not been exposed to the test compound. By comparing PKD in a test animal to an animal exposed to the test compound it may be possible to determine the effect of the test compound on PKD progression.

PKD is commonly associated with multiple cysts locates in the kidney. Hence one method to assess the effect of the test compound on PKD is to examine the kidney of a test animal and compare the amount, location or physiology of cysts to a reference animal. PKD progression can also be measured by ultrasound analysis or the use of a blood test that measures creatinine, urea and nitrogen levels, all of which are characteristically high in PKD patients.

The term "modulates PKD progression" includes increasing or reducing PKD progression. A preferred embodiment of the tenth aspect of the invention is wherein the compound selected in step iii) reduces PKD progression.

However, the tenth aspect of the invention may also be used to identify test compounds that increase PKD progression. Such compounds may be of use for developing a model animal system having accelerated PKD; this can be used to determine whether further test compounds, or other external stimuli, may be of use for preventing or treating PKD.

The screening methods of the invention can be used in "library screening" methods, a term well known to those skilled in the art. Thus, for example, the methods of the invention may be used to detect (and optionally identify) a test compound capable of modifying TAZ, TAZ-like or a polypeptide regulated by TAZ or TAZ-like polypeptide, or PKD progression. Aliquots of a library may be tested for the ability to give the required result.

Compounds that have been identified from the screening methods of the invention as of use in preventing or treating PKD can subsequently be further studied to determine their effect on, for example, the quantity of cysts, or to measure the effect of the identified compounds on creatinine, urea and nitrogen levels, as discussed above.

A further embodiment of the method of the fifth, sixth, seventh, eighth, ninth and tenth aspects of the invention is wherein compound for use in preventing or treating PKD is formulated into a pharmaceutically acceptable composition.

An eleventh aspect of the invention provides a method of making a compound useful in preventing or treating PKD comprising synthesising a compound identified or selected by any one of the method of the fifth, sixth, seventh, eighth, ninth and tenth aspects of the invention.

A twelfth aspect of the invention provides a pharmaceutical composition comprising the method of the fifth, sixth, seventh, eighth, ninth and tenth aspects of the invention and the step of mixing the compound of use in preventing or treating PKD with a pharmaceutically acceptable carrier.

Preferably, the formulation is a unit dosage containing a daily dose or unit, daily sub-dose or an appropriate fraction thereof, of the active ingredient.

The compounds will normally be administered orally or by any parenteral route, in the form of a pharmaceutical formulation comprising the active ingredient, optionally in the form of a non-toxic organic, or inorganic, acid, or base, addition salt, in a pharmaceutically acceptable dosage form.

Depending upon the disorder and patient to be treated, as well as the route of administration, the compositions may be administered at varying doses.

In human therapy, the compounds can be administered alone but will generally be administered in admixture with a suitable pharmaceutical excipient diluent or carrier selected with regard to the intended route of administration and standard pharmaceutical practice.

For example, the compounds can be administered orally, buccally or sublingually in the form of tablets, capsules, ovules, elixirs, solutions or suspensions, which may contain flavouring or colouring agents, for immediate-, delayed- or controlled-release applications. The compounds may also be administered via intracavernosal injection.

The compounds can also be administered parenterally, for example, intravenously, intra-arterially, intraperitoneally, intrathecally, intraventricularly, intrasternally, intracranially, intramuscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

A thirteenth aspect of the invention provides a method for assessing a patient's risk of developing PKD or progression of PKD, comprising the steps of:
  (i) obtaining a sample containing nucleic acid and/or protein from the patient; and,
  (ii) determining the amount and/or function and/or location of TAZ polypeptide and/or TAZ-like polypeptide and/or polypeptide regulated by TAZ or TAZ-like polypeptide, and/or determining the amount of nucleic acid encoding TAZ and/or a TAZ-like polypeptide and/or a polypeptide regulated by TAZ or TAZ-like polypeptide, and/or determining the patient's genotype of TAZ and/or a TAZ-like gene and/or a gene regulated by TAZ or TAZ-like polypeptide.

This method may be useful in the diagnosis of PKD or as a basis of genetic counseling.

Methods of determining the amount and function of TAZ polypeptide and/or TAZ-like polypeptide and/or polypeptide regulated by TAZ or TAZ-like polypeptide are presented above in relation to the screening methods of the invention.

Methods of determining the location of TAZ polypeptide and/or TAZ-like polypeptide and/or polypeptide regulated by TAZ or a TAZ-like polypeptide include in situ immuno-histochemistry analysis using an antibody that recognises said polypeptide, as would be appreciated by a person skilled in the art; or cell fractionation followed by an immunoassay for the presence of TAZ polypeptide and/or TAZ-like polypeptide and/or polypeptide regulated by TAZ or a TAZ-like polypeptide, again as would be appreciated by a person skilled in the art.

Methods of determining the amount of nucleic acid encoding TAZ and/or a TAZ-like gene and/or a gene regulated by TAZ or a TAZ-like polypeptide include northern blotting and RT-PCT as presented above in relation to the screening methods of the invention. Furthermore, it is possible that genomic rearrangements can lead to an increase in the copy number of gene(s) encoding TAZ polypeptide and/or TAZ-like polypeptide and/or polypeptide regulated by TAZ or a TAZ-like polypeptide, i.e. nucleic acids encoding said polypeptide. Methods of determining gene copy number include Southern blotting (essentially as performed as set out in Sambrook et al (1989). Molecular cloning, a laboratory manual, $2^{nd}$ edition, Cold Spring Harbor Press, Cold Spring Harbor, N.Y.) or quantitative PCR.

Methods of determining the patient's genotype of TAZ and/or a TAZ-like gene and/or a gene regulated by TAZ or a TAZ-like polypeptide include determining whether the patient has one or more mutation(s) in the gene, or complete absence of the gene(s) encoding TAZ polypeptide and/or TAZ-like polypeptide and/or polypeptide regulated by TAZ or a TAZ-like polypeptide, leading to reduced or nil expression of the polypeptide(s) or expression of functionally inactive versions of the polypeptide(s). By "gene" we include the coding region and the controlling region, e.g. the promoter, of the gene. Such genetic assay methods include the standard techniques of restriction fragment length polymorphism assays and PCR-based assays.

The assay may involve any suitable method for identifying such polymorphisms, such as: sequencing of the DNA at one or more of the relevant positions; differential hybridisation of an oligonucleotide probe designed to hybridise at the relevant positions of either the wild-type or mutant sequence; denaturing gel electrophoresis following digestion with an appropriate restriction enzyme, preferably following amplification of the relevant DNA regions; S1 nuclease sequence analysis; non-denaturing gel electrophoresis, preferably following amplification of the relevant DNA regions; conventional RFLP (restriction fragment length polymorphism) assays; selective DNA amplification using oligonucleotides which are matched for the wild-type sequence and unmatched for the mutant sequence or vice versa; or the selective introduction of a restriction site using a PCR (or similar) primer matched for the wild-type or mutant genotype, followed by a restriction digest. The assay may be indirect, i.e. capable of detecting a mutation at another position or gene which is known to be linked to one or more of the mutant positions.

The probes and primers may be fragments of DNA isolated from nature or may be synthetic. The methods used to determine genotype(s) are well known to those skilled in the art.

An embodiment of the thirteenth aspect of the invention is wherein if the sample has a reduced amount and/or function and/or an abnormal location of a TAZ polypeptide and/or TAZ-like polypeptide and/or polypeptide regulated by TAZ or a TAZ-like polypeptide, or if the sample has a reduced amount of nucleic acid encoding TAZ polypeptide and/or TAZ-like polypeptide and/or polypeptide regulated by TAZ or a TAZ-like polypeptide, or if the sample has a deleterious mutation in one or more gene(s) encoding TAZ and/or TAZ-like polypeptide and/or polypeptide regulated by TAZ or TAZ-like polypeptide, then the patient is considered to be at risk of developing PKD.

For example, in mice TAZ polypeptide is normally distributed between the cytoplasm and the nucleus, with some peptide being associated at the plasma membrane (Kanai et al, supra). TAZ can also accumulate in punctuate nuclear bodies via its C-terminal PDZ-binding motif. In contrast to TAZ, YAP is mainly distributed diffusely within the cytoplasm with only 10% of assayed cells showing a primarily nuclear staining pattern with no punctuate nuclear staining whatsoever. However, mutated TAZ polypeptides lacking the WW- or PDZ-domains have different distribution patterns. Therefore, assessing TAZ location may provide an assay as to the capacity of TAZ to function correctly in the patient and so provide a measure of the patient's risk of developing PKD.

Suitable samples that may be used in the methods of the thirteenth aspect of the invention include those which contain representative samples of the patient's polypeptide and/or nucleic acid. A preferred embodiment of the thirteenth aspect of the invention is wherein the sample contains cells from the kidney.

A fourteenth aspect of the invention provides a gene therapy vector comprising a polynucleotide which encodes TAZ polypeptide and/or TAZ-like polypeptide and/or polypeptide regulated by TAZ or a TAZ-like polypeptide.

Gene therapy vectors typically allow for the expression of a desired polypeptide(s) in a human cell. The vector may be one which allows for selective expression in the target cell by using promoter sequences which work selectively in the target cell type, for example kidney cell-specific expression.

Gene therapy vectors of the invention may be made by any suitable method. For example, a variety of methods have been developed to operably link DNA to vectors via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase or E. coli DNA polymerase I, enzymes that remove protruding, 3'-single-stranded termini with their 3'-5'-exonucleolytic activities, and fill in recessed 3'-ends with their polymerizing activities.

The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies Inc, New Haven, Conn., USA.

A desirable way to modify the DNA encoding the polypeptide of the invention is to use the polymerase chain reaction as disclosed by Saiki et al (1988) Science 239, 487-491.

In this method the DNA to be enzymatically amplified is flanked by two specific oligonucleotide primers which themselves become incorporated into the amplified DNA. The said specific primers may contain restriction endonuclease recognition sites which can be used for cloning into expression vectors using methods known in the art.

It will be appreciated that the gene expression vector of the invention may readily be made using molecular biological techniques which are well known in the art, such as those described in Sambrook et al (1989). Molecular cloning, a laboratory manual, $2^{nd}$ edition, Cold Spring Harbor Press, Cold Spring Harbor, N.Y.

An embodiment of the fourteenth aspect of the invention is wherein the vector comprises a Moloney Leukaemia Virus (MLV) based retroviral vector or a lentiviral vector or adeno-associated vector (AAV). Such vectors are well known to those skilled in the art and may be constructed using the methods disclosed above in relation to this aspect of the invention.

A fifteenth aspect of the invention provides a pharmaceutical composition comprising a polynucleotide encoding TAZ or a TAZ-like polypeptide or a polypeptide regulated by TAZ or a TAZ-like polypeptide or TAZ or a TAZ-like polypeptide or a polypeptide regulated by TAZ or a TAZ-like polypeptide or a compound identified from the screening methods of the invention or a compound as defined in relation to the eleventh aspect of the invention or a gene therapy vector as defined in the twelfth aspect of the invention and a pharmaceutically acceptable carrier.

A discussion of pharmaceutically acceptable carriers is provided above in relation to the twelfth aspect of the invention.

A sixteenth aspect of the invention provides a polynucleotide encoding TAZ or a TAZ-like polypeptide or a polypeptide regulated by TAZ or a TAZ-like polypeptide or TAZ or a TAZ-like polypeptide or a polypeptide regulated by TAZ or a TAZ-like polypeptide or a compound identified from the screening methods of the invention or a compound as defined in relation to the eleventh aspect of the invention or a pharmaceutical composition as defined in relation to the screening methods of the invention or in the twelfth or fifteenth aspects of the invention or a gene therapy vector as defined in the fourteenth aspect of the invention for use in medicine.

A seventeenth aspect of the invention provides the use of a polynucleotide encoding TAZ or a TAZ-like polypeptide or a polypeptide regulated by TAZ or a TAZ-like polypeptide or TAZ or a TAZ-like polypeptide or a polypeptide regulated by TAZ or a TAZ-like polypeptide or a compound identified from the screening methods of the invention or a compound as defined in relation to the eleventh aspect of the invention or a pharmaceutical composition as defined in relation to the screening methods of the invention or in the twelfth or fifteenth aspects of the invention or a gene therapy vector as defined in the fourteenth aspect of the invention in the manufacture of a medicament for the treatment of a patient with or at risk of developing PKD.

A eighteenth aspect of the invention provides a method of treating a patient with PKD comprising administering to the patient an effective amount of a polynucleotide encoding TAZ or a TAZ-like polypeptide or a polypeptide regulated by TAZ or a TAZ-like polypeptide or TAZ or a TAZ-like polypeptide or a polypeptide regulated by TAZ or a TAZ-like polypeptide or a compound identified from the screening methods of the invention or a compound as defined in relation to the eleventh aspect of the invention or a pharmaceutical composition as defined in relation to the screening methods of the invention or in the twelfth or fifteenth aspects of the invention or a gene therapy vector as defined in the fourteenth aspect of the invention.

Means and methods of introducing a genetic construct into a cell in an animal body are known in the art. For example, the polynucleotide of use in the fifteenth, sixteenth, seventeenth and eighteenth aspects of the invention may be introduced into the target cells by any convenient method, for example methods involving adenoviruses.

Targeted retroviruses are also available for use in the invention; for example, sequences conferring specific binding affinities may be engineered into preexisting viral env genes (see Miller & Vile (1995) *Faseb J* 9, 190-199 for a review of this and other targeted vectors for gene therapy). The tropism of a retroviral vector can be altered by the incorporation of foreign or hybrid envelope proteins (Battini J L, et al *J. Virol.* 66: 1468-1475; 1992). This can be achieved by insertion of monoclonal antibodies to mouse ecotropic retroviral particles. Alternatively, any chemical modification such as lactose binding to virus particles can increase the range possible target cells for transduction or confer a predictably altered recognition specificity. Retrovirus particles displaying non-viral polypeptides may be used for specific target cells through the non-viral moiety.

Other methods involve simple delivery of the genetic construct into the cell for expression therein either for a limited time or, following integration into the genome, for a longer time. An example of the latter approach includes (preferably kidney-cell-targeted) liposomes (Næssander et al (1992) *Cancer Res.* 52, 646-653).

For the preparation of immuno-liposomes MPB-PE (N-[4-(p-maleimidophenyl)butyryl]-phosphatidylethanolamine) is synthesised according to the method of Martin & Papahadjopoulos (1982) *J. Biol. Chem.* 257, 286-288. MPB-PE is incorporated into the liposomal bilayers to allow a covalent coupling of the antibody, or fragment thereof, to the liposomal surface. The liposome is conveniently loaded with DNA or other genetic construct for delivery to the target cells, for example, by forming the said liposomes in a solution of the DNA or other genetic construct, followed by sequential extrusion through polycarbonate membrane filters with 0.6 μm and 0.2 μm pore size under nitrogen pressures up to 0.8 MPa. After extrusion, entrapped DNA construct is separated from free DNA construct by ultracentrifugation at 80 000×g for 45 min. Freshly prepared MPB-PE-liposomes in deoxygenated buffer are mixed with freshly prepared antibody (or fragment thereof) and the coupling reactions are carried out in a nitrogen atmosphere at 4° C. under constant end over end rotation overnight. The immunoliposomes are separated from unconjugated antibodies by ultracentrifugation at 80 000×g for 45 min. Immunoliposomes may be injected intraperitoneally or directly into the target tissue.

Examples of polynucleotides that encode a TAZ polypeptide or a TAZ-like polypeptide are disclosed above in relation to the first aspect of the invention and are presented in FIGS. 3 and 4. Further polynucleotides of use in the fifteenth, sixteenth, seventeenth and eighteenth aspects of the invention may be identified according to methods set out in relation to the first aspect of the invention.

The fifteenth, sixteenth, seventeenth and eighteenth aspects of the invention includes TAZ or a TAZ-like polypeptide or a polypeptide regulated by TAZ or a TAZ-like polypeptide.

Polypeptide may be delivered using an injectable sustained-release drug delivery system. These are designed specifically to reduce the frequency of injections. An example of such a system is Nutropin Depot which encapsulates recombinant human growth hormone (rhGH) in biodegradable microspheres that, once injected, release rhGH slowly over a sustained period.

The polypeptide can be administered by a surgically implanted device that releases the drug directly to the required site. For example, Vitrasert releases ganciclovir directly into the eye to treat CMV retinitis. The direct application of this toxic agent to the site of disease achieves effective therapy without the drug's significant systemic side-effects.

Electroporation therapy (EPT) systems can also be employed for the administration of polypeptide. A device which delivers a pulsed electric field to cells increases the permeability of the cell membranes to the drug, resulting in a significant enhancement of intracellular drug delivery.

Polypeptide can be delivered by electroincorporation (EI). EI occurs when small particles of up to 30 microns in diameter on the surface of the skin experience electrical pulses identical or similar to those used in electroporation. In EI, these particles are driven through the stratum corneum and into deeper layers of the skin. The particles can be loaded or coated with drugs or genes or can simply act as "bullets" that generate pores in the skin through which the drugs can enter.

An alternative method of polypeptide delivery is the ReGel injectable system that is thermo-sensitive. Below body temperature, ReGel is an injectable liquid while at body temperature it immediately forms a gel reservoir that slowly erodes and dissolves into known, safe, biodegradable polymers. The active drug is delivered over time as the biopolymers dissolve.

Polypeptide pharmaceuticals can also be delivered orally. The process employs a natural process for oral uptake of vitamin $B_{12}$ in the body to co-deliver proteins and peptides. By riding the vitamin $B_{12}$ uptake system, the protein or peptide can move through the intestinal wall. Complexes are synthesised between vitamin $B_{12}$ analogues and the drug that retain both significant affinity for intrinsic factor (IF) in the vitamin $B_{12}$ portion of the complex and significant bioactivity of the drug portion of the complex.

Polypeptides can be introduced to cells by "Trojan peptides". These are a class of polypeptides called penetratins which have translocating properties and are capable of carrying hydrophilic compounds across the plasma membrane. This system allows direct targeting of oligopeptides to the cytoplasm and nucleus, and may be non-cell type specific and highly efficient. See Derossi et al (1998), *Trends Cell Biol* 8, 84-87.

Examples of TAZ or a TAZ-like polypeptide are disclosed above in relation to the first aspect of the invention and are presented in FIGS. 3 and 4. Further polypeptides of use in the fifteenth, sixteenth, seventeenth and eighteenth aspects of the invention may be identified according to methods set out in relation to the third aspect of the invention.

A nineteenth aspect of the invention provides the use of an agent which is capable of determining the amount and/or function and/or location of TAZ polypeptide and/or TAZ-like polypeptide and/or polypeptide regulated by TAZ or a TAZ-like polypeptide, and/or determining the amount of nucleic acid encoding TAZ and/or a TAZ-like gene and/or a gene regulated by TAZ or a TAZ-like polypeptide, and/or determining the genotype of TAZ and/or a TAZ-like gene and/or a gene regulated by TAZ or a TAZ-like polypeptide in the manufacture of a reagent for diagnosing PKD.

Agents that can be used in this aspect of the invention to determine the amount and/or function and/or location of TAZ polypeptide and/or TAZ-like polypeptide and/or polypeptide regulated by TAZ or a TAZ-like polypeptide include antibodies or peptide or compounds that can to said polypeptides. Furthermore, as set out above in relation to the screening methods of the invention, agents that may be used to assess the function of TAZ polypeptide and/or TAZ-like polypeptide and/or polypeptide regulated by TAZ or a TAZ-like polypeptide include reporter genes and regulatable by said polypeptides and coactivation partners for said polypeptides.

Agents that can be used in this aspect of the invention to determine the amount of nucleic acid encoding TAZ and/or a TAZ-like gene and/or a gene regulated by TAZ or a TAZ-like polypeptide include primers, oligonucleotides, or other nucleic acid molecules useful in PCR-based methods, northern blotting and in situ hybridisation methods set out above in relation to the screening methods of the invention.

Agents that can be used in this aspect of the invention to determine the genotype of TAZ and/or a TAZ-like gene and/or a gene regulated by TAZ or a TAZ-like polypeptide include primers, oligonucleotides, or other nucleic acid molecules useful in the methods set out above in relation to the thirteenth aspect of the invention.

A twentieth aspect of the invention provides a method of diagnosing PKD comprising the steps of:
(i) obtaining a sample containing nucleic acid and/or protein from a patient; and,
(ii) determining the amount and/or function and/or location of TAZ polypeptide and/or TAZ-like polypeptide and/or polypeptide regulated by TAZ or a TAZ-like polypeptide, and/or determining the amount of nucleic acid encoding TAZ and/or a TAZ-like polypeptide and/or a polypeptide regulated by TAZ or a TAZ-like polypeptide, and/or determining the patient's genotype of TAZ and/or a TAZ-like gene and/or a gene regulated by TAZ or a TAZ-like polypeptide.

Methods and agents that can be used in step (ii) of this aspect of the invention have been discussed above in relation to the nineteenth aspect of the invention.

A twenty-first aspect of the invention provides a method of assessing the status of TAZ polypeptide and/or TAZ-like polypeptide and/or polypeptide regulated by TAZ in a patient comprising the steps of:
(i) obtaining a sample containing nucleic acid and/or protein from a patient; and,
(ii) determining the amount and/or function and/or location of TAZ polypeptide and/or TAZ-like polypeptide and/or polypeptide regulated by TAZ, and/or determining the amount of nucleic acid encoding TAZ and/or a TAZ-like polypeptide and/or a polypeptide regulated by TAZ, and/or determining the patient's genotype of TAZ and/or a TAZ-like gene and/or a gene regulated by TAZ.

Methods and agents that can be used in step (ii) of this aspect of the invention have been discussed above in relation to the seventeenth aspect of the invention.

By "assessing the status" we include determining whether the amount and/or function and/or location of TAZ polypeptide and/or TAZ-like polypeptide and/or polypeptide regulated by TAZ, or the amount of nucleic acid encoding TAZ and/or a TAZ-like polypeptide and/or a polypeptide regulated by TAZ differs in a sample to that of a reference sample from a further patient. Reference samples have been discussed above in relation to the screening methods of the invention. Similarly, we include determining whether the genotype of TAZ and/or a TAZ-like gene and/or a gene regulated by TAZ in the sample is different to the normal sequence of the said genes(s). Using the information gained in step (ii) of this method of the invention, a judgement can be made as to the status of TAZ in the patient; for example, whether the status of the said polypeptide is similar to that which would lead to PKD. Thus, the method may be useful in the diagnosis of PKD or as a basis of genetic counseling.

A twenty-second aspect of the invention provides a kit of parts useful for diagnosing PKD comprising an agent which is capable of use in assessing the amount or function of TAZ polypeptide and/or TAZ-like polypeptide and/or polypeptide regulated by TAZ or a TAZ-like polypeptide, or the amount of nucleic acid encoding said polypeptide, or assessing the genotype of TAZ and/or a TAZ-like gene and/or a gene regulated by TAZ or a TAZ-like polypeptide in a sample.

Agents that may be of use in the twenty-second aspect of the invention have been discussed above in relation to the nineteenth aspect of the invention. For example, agents of use in assessing the amount of nucleic acid encoding TAZ polypeptide and/or TAZ-like polypeptide and/or polypeptide regulated by TAZ include a nucleic acid probe that can be used in northern blotting or an oligonucleotide of use in a RT-PCT reaction; agents of use in assessing the amount of TAZ polypeptide and/or TAZ-like polypeptide and/or polypeptide regulated by TAZ polypeptide include antibodies that can bind to the said polypeptide; agents of use in assessing the function of TAZ polypeptide and/or TAZ-like polypeptide and/or polypeptide regulated by TAZ polypeptide include reporter genes and coactivation partners as discussed above.

A further embodiment of the twenty-second aspect of the invention is a kit of parts further comprising a negative control and/or a positive control.

A further embodiment of the twenty-second aspect of the invention is a kit of parts further comprising means for separating kidney cells from a sample.

The invention will now be described in more detail, for the purposes of illustration only, in the following Examples and Figures.

FIG. 1: Targeting of Taz locus Upper, the genomic fragment of Taz gene containing exon-1 and exon-2. Middle, targeting vector containing homology fragments of Taz locus with inframe insertion of lacZ sequence and loxp flanked neomycin cassette at the exon2 with deletion of 384 bp. A diphtheria toxin-A gene cassette is located out side of the homology fragments. Lower, the targeted Taz locus with disrupted exon2 by inframe lacZ and loxp flanked neomycin cassette insertion. Length of wild type and mutant fragment detected by Southern hybridization with ScaI digestion has been shown. Thick lines represent Taz genomic sequences; thin lines, pBluescript sequences; black boxes, Taz coding exons; black ovals, loxP sequences. gray boxes denoted as lacZ, neo and DT-A indicate lacZ cDNA lacking 3'UTR, neomycin-resistant gene with polyadenylation signal driven by Pgk1 promoter and diphtheria toxin-A fragment gene with MCI promoter, respectively. Primers (p1+p2) are used for the detection of the wild type allele; primers (p3+p4) or (p3+p5) used for the detection of mutant allele in routine genotyping either by conventional or long-range PCR technique. The fragment 'sp' is the probe used for Southern blotting to identify homologous recombination or targeted allele. B, BamHI; P, PstI; S, SmaI; Sa, SalI; Sc, ScaI.

FIG. 2: Gross anatomy and histology of kidney from 6 weeks old TAZ$^{+/1}$ and TAZ$^{-/-}$ litter mates. Note the enlarged anemic kidney for the homozygous animals and the numerous cysts located at the corticomedullary junction.

FIG. 3: Human and mouse TAZ sequences.

(A): Human TAZ polypeptide sequence; GenBank Accession Number NP_056287.1 (Sequence ID No. 1).

(B): Human TAZ polynucleotide sequence; GenBank Accession Number NM_015472.3 (Sequence ID No. 2).

(C): Mouse TAZ polypeptide sequence; GenBank Accession Number CAC17733 (Sequence ID No. 3)

(D): Mouse TAZ polynucleotide sequence; GenBank Accession Number AJ299430 (Sequence ID No. 4)

FIG. 4: Human and mouse YAP sequences.

(A): Human YAP polypeptide sequence; GenBank Accession Number NP_006097 (Sequence ID No. 5).

(B): Human YAP polynucleotide sequence; GenBank Accession Number NM_006106 (Sequence ID No. 6).

(C): Mouse YAP polypeptide sequence; GenBank Accession Number AAH39125 (Sequence ID No. 7).

(D): Mouse YAP polynucleotide sequence; GenBank Accession Number BC039125 (Sequence ID No. 8).

(E) Chicken YAP polypeptide sequence; GenBank Accession Number NP_990574 (Sequence ID No. 9).

(F) Chicken YAP polynucleotide sequence; GenBank Accession Number NM_205243 (Sequence ID No. 10).

Figure 5:
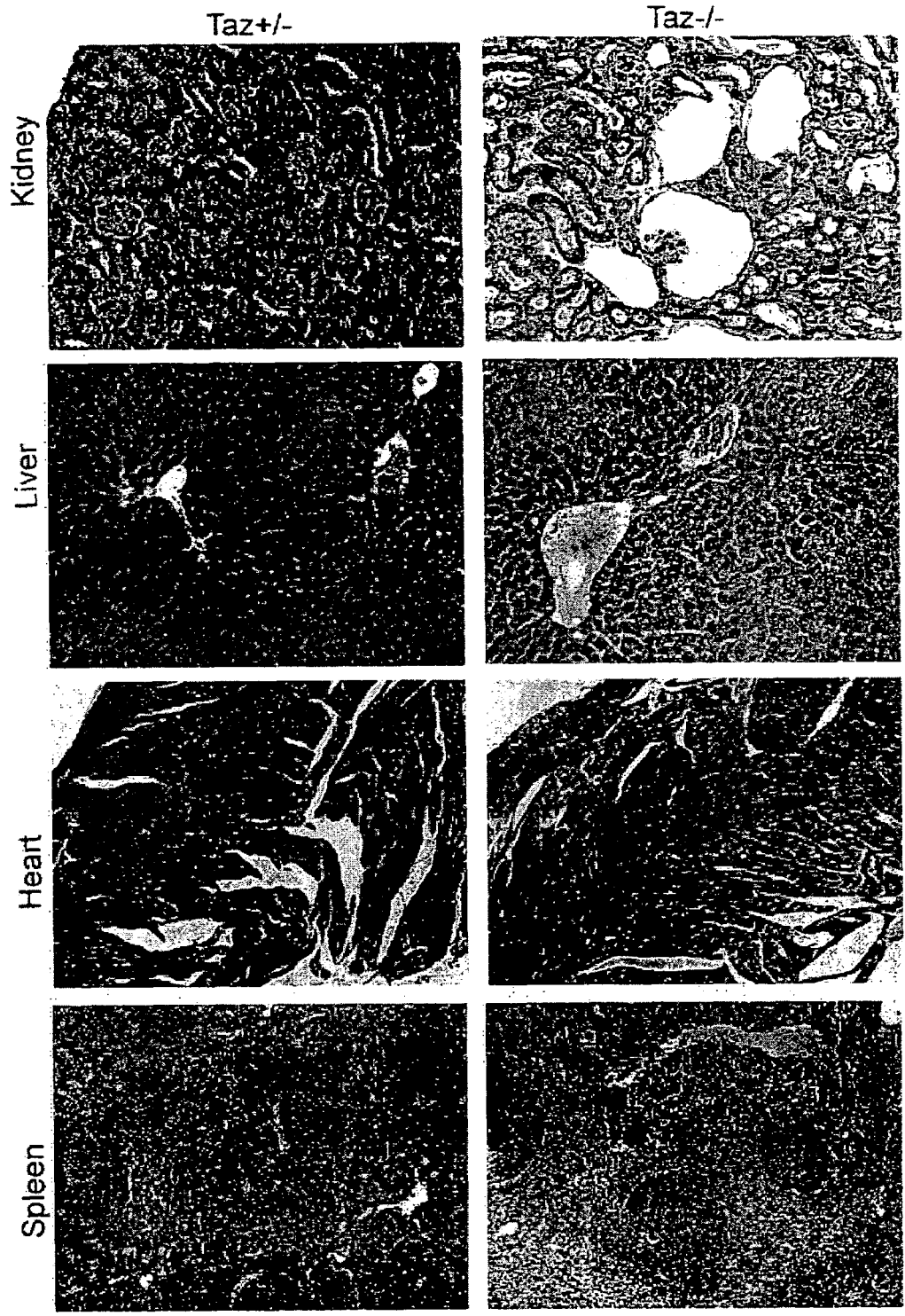

FIG. 5: Histological analysis of organs.

Sections through tissues isolated from TAZ$^{+/-}$ and TAZ$^{-/-}$ mice.

Figure 6:
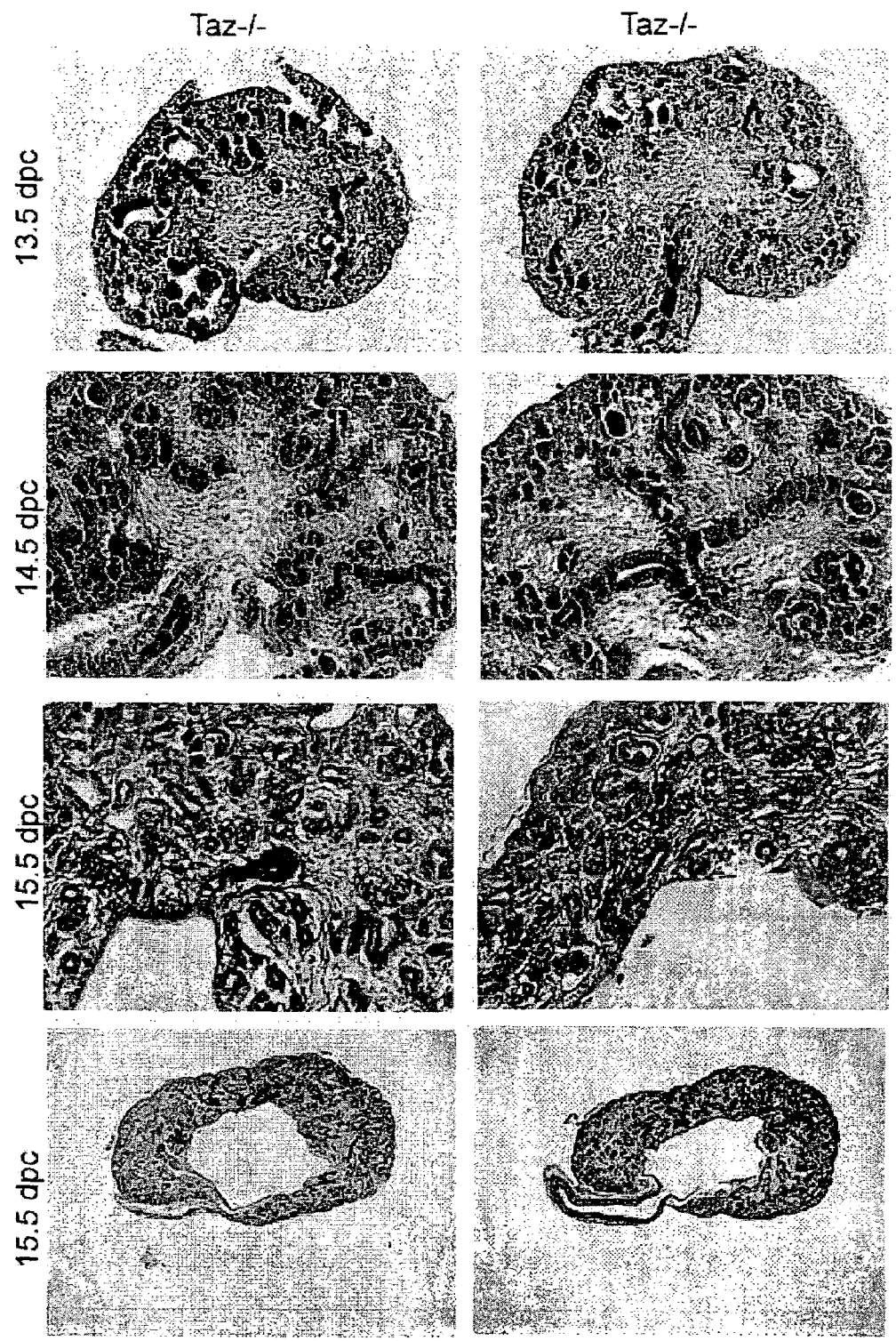

FIG. 6: LacZ expression at embryonic stage

LacZ expression in embryonic tissues of TAZ$^{-/-}$ mice.

Figure 7:
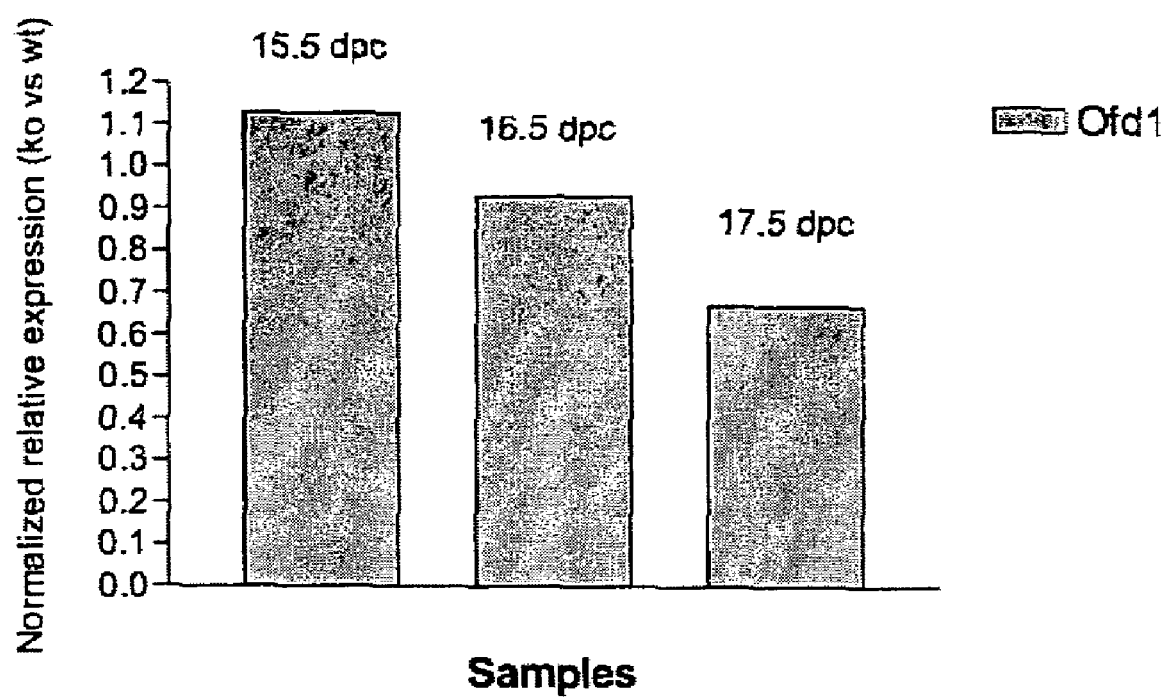

FIG. 7: Down regulation of Ofd1 in the kidney of TAZ knockout mice

Expression of Ofd1 in 15.5 dpc, 16.5 dpc and 17.5 dpc kidney tissues.

EXAMPLE 1

A TAZ$^{-/-}$ Mouse

TAZ (transcriptional co-activator with PDZ-binding motif) is a recently identified transcriptional co-activator with high homology to YAP (yes associated protein) (Kanai et al, supra). TAZ is highly expressed in heart, lung, liver and kidney and functions as a transcriptional coactivator by binding, via its single WW domain, to PPXY motifs present in targeted transcription factors (Kanai et al, supra). Bone-specific transcription factor (Cbfa1/Runx2) (Cui et al, supra) and thyroid transcription factor-1 (TTF-1/Nkx-2.1) (Park et al, supra) are targets of TAZ identified to date. In addition, TAZ can bind 14-3-3 and PDZ-domain proteins, interactions that may determine its subcellular localization (Kanai et al, supra). We inactivated by homolgous recombination the TAZ gene. TAZ$^{-/-}$ mice show a decreased survival rate and surviving animals develop kidney cysts at the corticomedullary border, reminiscent of human nephronophthisis (Riele et al (1992) Proc Natl Acad Sci USA 89, 5128-5132). Thus, TAZ is not required for kidney development per se but plays a critical role in kidney physiology, with mutations in the TAZ gene leading to PKD.

Methods and Results

Generation Taz Knock-Out Mouse

Construction of Taz-lacZ Knock-In Vector:

A 18-20 kb genomic DNA fragment was isolated by screening recombinant mouse DNA library using a non-radioactive PCR technique (Amaravadi and King, 1994). An annotated sequence of the isolated genomic fragment had been downloaded and exon-intron organization and partial restriction map were derived. For the construction, lacZ (3.3 kb) cDNA lacking 3'UTR was ligated inframe to the initiation codon (ATG) at the 2$^{nd}$ exon of Taz locus by recombinant PCR technique, followed loxP flaked neomycin resistant gene with polyadenylation signal driven by the Pgk1 promoter. The lacZ-loxP-neo-loxP was flanked by two homologous fragments of Taz genomic DNA length of 4.2 and 3.1 kb. Finally the construct was cloned in a plasmid containing a diphtheria toxin-A fragment (DT-A) gene driven by MCI promoter for negative selection as described by Yagi et al., (1993). A schematic representation of the TAZ loci and the homologous recombination construct is shown in FIG. 1.

ES Cell Culture and Transfection:

W4 ES cells (Taconic, USA) were cultured according to the standard protocol and electroporated with SalI linearized targeting vectors (Riele et al (1992) Proc Natl Acad Sci USA 89, 5128-5132); then cultured and selected against 200-300 ug of G418. After the positive-negative selection, 120 ES colonies were picked-up and screened by long PCR technique using primers (p3 and p4, generating a 3.8 kb fragment from targeted allele). PCR positive clones were further examined by the southern hybridization for homologous recombination.

Chimera Mice Production and Breeding:

ES cells from targeted clones were injected into blastocyst (3.5 dpc) embryos. One out of 4 clones had colonized the germ line of chimera mice. The chimera was then mated with wild type mice either with 129 or C57BL/6 strain and heterozygous offspring were identified by routine PCR technique using primers (p3 and p5, generating a 700 bp fragment from mutant allele). Heterozygous mice were further mated for the generation of homozygous mutants and were genotyped using primers (p3 and p5) and primers (p1 and p3, generating a 500 bp fragment from wild type allele).

X-Gal Staining of Kidney

The kidney was dissected from 13.5 to 15.5 days post coitum (dpc) and the lacZ staining was performed according to Lobe et al (1999) Dev Biol 208, 281-292. Stained embryos were washed three times with PBS and refixed in 4% paraformaldehyde in PBS. Samples were subsequently dehydrated and embedded in paraplast. Serial sections (4-8 mm) were prepared and counterstained with 1% eosin.

Histological Analysis of Organs

Organs from adult mice were fixed with 10% formalin at room temperature for 18-24 hours. Specimens were subsequently dehydrated and embedded in paraplast. Serial sections (4-8 mm) were prepared and stained with hematoxylin and eosin.

Survivality Analysis:

Heterozygous mice were allowed to mate. The number of newborn was counted and subsequently dead pups were separated and genotyped routinely. However, surviving pups were genotyped at 3-4 weeks by PCR using tail DNA Discussion Transcriptional co-activator with PDZ-binding motif (TAZ) is a recently identified transcriptional co-activator with high homology to Yes associated protein (YAP) (Kanai et al, supra). TAZ is highly expressed in heart, lung, liver and kidney and functions as a transcriptional co-activator by binding, via a single WW domain, to PPXY motifs present in target transcription factors (Kanai et al, supra). To date, bone-specific transcription factor (Cbfa1/Runx2) (Cui et al, supra) and thyroid transcription factor-1 (TTF-1/Nkx-2.1) (Park et al, supra) are the only known targets of TAZ. In addition to its association with transcription factors, TAZ can bind signaling and scaffolding proteins such as 14-3-3 and PDZ-domain proteins, interactions that are thought to regulate the subcellular localization of TAZ (Kanai et al, supra).

We inactivated by homologous recombination the TAZ gene in mice. Although $TAZ^{-/-}$ animals show an increased postnatal mortality, many live for at least 6 months, see Table 1 below:

TABLE 1

| | Survivality of Taz mutants | | | | |
|---|---|---|---|---|---|
| | Number of | Genotyping | | | |
| | offspring | +/+ | +/− | −/− | unknown |
| Live | 92 | 24 | 54 | 14 | 0 |
| Dead | 15 | 2 | 0 | 8 | 5 |
| Total | 107 | 26 | 54 | 22 | 5 |
| (%) | (100) | (24.3) | (50.5) | (20.5) | (4.7) |

Surprisingly, the most striking phenotype of $TAZ^{-/-}$ mice are the slightly enlarged, anemic and cystic kidneys (FIG. 2). Renal cysts are restricted to the corticomedullary interface and absent from other organs, reminiscent of human NPH-MCKD and most often affect glomeruli, reminiscent of GCKD (FIG. 5). Given the autosomal recessive transmission and early onset (Hildebrandt et al supra), and the predominant association of cysts with glomeruli, the phenotype of the $TAZ^{-/-}$ mice most closely relates to NPH and/or GCKD.

The $TAZ^{-/-}$ animals express β-galactosidase under the control of the endogenous TAZ promoter. β-galactosidase staining in $TAZ^{-/-}$ and $TAZ^{+/-}$ mice and immunohistochemistry using TAZ antibodies in $TAZ^{+/-}$ and $TAZ^{+/+}$ animals indicate that TAZ is expressed in the glomeruli and proximal tubules. TAZ expression in the kidney is first detected at embryonic stage 14.5 dpc and the first indications of cyst development are apparent at 16.5 dpc (FIG. 6; $TAZ^{+/-}$ animals give the same staining of β-galactosidase activity as $TAZ^{-/-}$ but weaker. No staining is observed in the $TAZ^{+/+}$ animals control animals).

EXAMPLE 2

Identifying Further Polypeptides Regulated by TAZ

Identification of Up- or Downregulated Genes in $TAZ^{-/-}$ Mice

To identify differentially expressed genes which are up- or down-regulated in TAZ mutant animals, microarrays are probed with RNA from kidneys of $TAZ^{-/-}$ and $TAZ^{+/-}$ littermates. RNA is isolated from whole kidney and medulla, or from individual cells that normally express TAZ.

Since TAZ expression is first detected at 14.5 dpc and indications of cyst development are apparent at 16.5 dpc (see above), analysis is performed with RNA isolated from whole kidney from three stages: 14.5 dpc (first detection of TAZ expression); 15.5 dpc (TAZ expression and no cysts) and 16.5 dpc (cyst development). In addition to kidney, arrays are probed with RNA from liver and pancreas of $TAZ^{-/-}$ and $TAZ^{+/-}$ mice. Since TAZ is highly expressed in liver and pancreas but these organs do not develop cysts in the $TAZ^{-/-}$ animals, comparison of data from kidney with that form liver and pancreas helps to narrow down differentially expressed genes relevant to kidney development and possibly cyst formation.

Since $TAZ^{-/-}$ and $TAZ^{+/-}$ mice express β-galactosidase under the control of the endogenous TAZ promoter (see above), detection of β-galactosidase activity, in conjunction with immunohistochemistry using markers specific for individual cell types, allows the identification of the cell type(s) in which TAZ is normally expressed. Microarray analysis can be performed using RNA probes from matched individual cells isolated by laser dissection microscopy (Hahn et al 2002) Methods Enzymol 356:295-301; Hahn et al (2000) Cell Mol Life Sci 57:96-105).

Comparative analysis of the microarray data sets for organs susceptible or not to cyst formation, for whole kidney, medulla and individual renal cells, and for different developmental stages, provides a detailed gene expression profiling for the critical phase between TAZ expression and cyst formation. In addition, this facilitates the identification of genes linked to cyst development. Genes of interest are identified based on specific criteria (see below) and their differential expression in kidneys of $TAZ^{-/-}$ and $TAZ^{+/-}$ mice confirmed by RT-PCR, in situ hybridization and, if antibodies are available, immunohistochemistry.

Identification of Proteins that Interact with TAZ

Yeast two-hybrid screens preformed using TAZ (both as full length protein or fragments encoding particular domains or domain combinations) as bait identifies interacting proteins encoded by a kidney cDNA library. The interaction between TAZ and identified prey proteins are confirmed both in vitro (pull down experiments using GST-TAZ fusion proteins and in vitro translated prey proteins) and in vivo (co-precipitation and co-localization experiments following co-expression of epitope tagged TAZ and the prey). In addition to Cbfa (Cui et al, supra) and TTF-1 (Park et al, supra), both known to bind TAZ, additional transcription factors, as well as regulatory and structural proteins containing WW binding motifs or PDZ domains are identified. For example, the polypeptide encoded by hepatocyte nuclear factor-1beta (HNF-1b) transcription factor gene has a PPXY motif (and hence may interact with TAZ) could be identified.

Characterization of Selected Differentially Expressed Gene Products and Interacting Proteins Proteins encoded by genes differentially expressed in $TAZ^{-/-}$ versus $TAZ^{+/-}$ mice (see above) or proteins that interact with TAZ (see above) are further characterized to elucidate their function in normal kidney physiology and to determine how they might contribute to cyst formation.

Priority is given to proteins where the orthologue is mutated in patients suffering from NPH-MCKD or GCKD. Linkage analysis in families with NPH-MCKD provides a multitude of positional candidate regions. This may rapidly identify novel human genes involved in NPH-MCKD and/or GCKD.

Since positional candidate regions are only known for a relatively small number of NPH-MCKD and GCKD patients, many differentially expressed genes or genes encoding interacting proteins are associated with such regions. Other criteria, such as a similar temporal and spatial expression in the kidney as TAZ is used to shortlist proteins to be characterized. Since cyst formation may be linked to abnormalities in epithelial cell growth, trans-epithelial transport, cell adhesion or primary cilia function, the focus is on proteins linked to these functions. Novel proteins of unknown function are considered. The details for the cell biological characterization of a selected protein will strongly depend on the function it is putatively associated with. Both in vitro cell culture models and in vivo animals models are used.

For in vitro experiments, use is made of kidney epithelial cell lines and the ability to grow these cells as monolayers (Hunziker et al (1991) Cell 66, 907-920) or organotypic cysts and tubules (Zegers et al (2003) Trend Cell Biol 13, 169-176). Expression of wild-type proteins or proteins in which particular domains have been mutated is studied in these culture systems with respect to subcellular localization and function. Furthermore, RNAi approaches are used to repress the expression of the protein. If antibodies to a particular protein are not available, epitope tagged variants are used.

For in vivo studies, use is made of Zebrafish and mice as model systems. If there is a zebrafish ortholog for the protein of interest, in situ hybridization is used, or if working antibodies are available immunohistochemistry, to determine the temporal and spatial expression pattern in Zebrafish. The use morpholinos to repress expression of a particular gene in Zebrafish will allow to rapidly screen for kidney phenotypes in this animal model. The physiological role of chosen proteins is further defined in knock out mice, focusing on proteins whose gene is mutated in patients with NPH-MCKD and GCKD.

EXAMPLE 3

Microarray and RT-PCR Analysis of Differentially Expressed Genes

Microarray Analysis Using Affymetrix GeneChips:

For microarray analysis each pair of kidney was harvested from the embryo from $Taz^{+/-}$ mating, frozen-down immediately on dry ice and stored them at $-80°$ C. Genotyping was confirmed by PCR using the DNA samples extracted from the tail tissue. Then the 5 pairs of kidneys from same genotype (either $Taz^{+/+}$ or $Taz^{-/-}$) were pooled and kidney powder was prepared on liquid nitrogen by mortar and pastel. Total RNA was extracted from the kidney powder using total RNA isolation kit (Macherey-Nagel) with DNase I treatment. Double-strand cDNA was synthesized from 5 µg of total RNA using a Super Script Choice cDNA synthesis kit (Invitrogen, Carlsbad, Calif.) with an oligo$(dT)_{24}$ primer containing a T7 polymerase promoter site at the 3' end. Biotin-labeled cRNA was synthesized by T7 RNA polymerase using the double-strand cDNA as a template (Bioarray high yield RNA transcript labeling kit; Enzo Diagnostics, Farmingdale, N.Y.) and purified with the use of the RNeasy RNA purification kit (Qiagen, Valencia, Calif.). The biotin-labeled cRNA was fragmented and hybridized to a GeneChip microarray (Affymetrix, Santa Clara, Calif.) for 16 h at 42° C. After hybridization, the arrays were washed and stained with biotinylated antistreptavidin antibody (Vector Laboratories, Burlingame, Calif.) and a phycoerythrin-streptavidin conjugate (Molecular Probes, Eugene, Oreg.) according to the manufacturer's protocol. GeneChip arrays were scanned on an Affimetrix probe array scanner and initial data were analysed using a statistics software MAS-5.0 from Affymetrix. The data generated is presented in Tables 2 to 9.

Results and Discussion

Based mainly on the observation that several genes mutated in PKD code for proteins that can localize to cilia (Pazour et al., 2002; Yoder et al., 2002; Otto et al., 2003; Ward et al., 2003; Watanabe et al., 2003), a link between cyst formation and cilia defects has been proposed (Pazour and Witman, 2003). Primary cilia are related to the flagella of sperm and protozoa but differ from motile cilia in their axonemal structure (9+0 as opposed to 9+2). Axonems are mainly assembled from microtubule subunits, dynein arms, and radial spoke proteins. Ciliogenesis involves the duplication of centrioles, the migration of the centrioles to the apical pole to become basal bodies, the elongation of the microtubule based axoneme, and the formation of accessory structures of the basal body (Hagiwara et al., 2000). The assembly and maintenance of cilia/flagella is thought to involve intraflagellar transport (IFT), a process discovered in the green algae *Chlamydomonas* (Rosenbaum and Witman, 2002). IFT involves the continuous antero- and retrograde movement of IFT particles along the microtubule pairs in the axoneme using kinesin-2 and cytoplasmic dynein microtubule motors, respectively (Orozco et al., 1999; Signor et al., 1999). IFT particles are composed of at least 17 proteins, forming so called A and B complexes that carry components such as microtubule subunits, dynein arms and spoke proteins required for assembly and maintenance of the axoneme and the ciliary/flagellar membrane. Mutations in genes encoding IFT particle proteins block ciliary assembly in *Chlamydomonas, C. elegans, Drosophila* and mouse. In the mouse, a complete null allele of polaris/Tg737, a protein required for IFT B complex formation, blocks assembly of cilia on the embryonic node, resulting in embryonic lethality during mid-gestation (Murcia et al., 2000; Huangfu et al., 2003), whereas a partial loss of function mutation retards cilia formation causing cysts in the kidney, liver and pancreas (Moyer et al., 1994; Pazour et al., 2000). Renal inactivation of the KIF3A gene, which encodes a microtubule motor required for antero-grade IFT, blocks ciliary assembly and leads to cyst formation (Rosenbaum and Witman, 2002; Lin et al., 2003). Lending support for a ciliar model for PKD, the proteins of several genes associated with APKD (PKD1/2), ARPKD (PKHD1) and NPH (NPHP1/2/3/4) have been localized to cilia (Pazour and Witman, 2003). However, in most of these cases cilia were still present during cytogenesis, implicating defects in cilia function (i.e. mechanosensation) rather than cilia loss in these cases of PKD. Indeed, PKD1, a ciliary sensor, is coupled to PKD2, a $Ca^{2+}$ channel, which, in response to ciliar stimuli, mediates cellular $Ca^{2+}$ influx for the regulation of cell proliferation, (Cantiello, 2003; Nauli et al., 2003).

The finding that the expression of several genes (e.g. Rpgrip1, Hif1a, Ctss, Pcm1, Dctn3, Dctn5, Kif5b and Nisch) that encode proteins that either localize to cilia (Rpgrip, Hif1a, Pcm1, Dctn3, Dctn5), or are associated with the structure and/or function of cilia (Pcm1, Ctss, Dctn3, Dctn5) and/or microtubules (Dctn3, Dctn5, Kif5b), were downregulated by greater than two fold in TAZ$^{-/-}$ kidneys supports a requirement for TAZ in assembly, function and/or maintenance of cilia in the kidney. Rpgrip-1 interacts with the retinitis pigmentosa GTPase regulator (Roepman et al., 2000) and localizes to the photoreceptor connecting cilium (Hong et al., 2001), a thin cilia-like bridge linking the cell body and the light-sensing outer segment. Mutations in Rpgrip-1 are linked to Leber congenital amaurosis (Meindl et al., 1996) and while Rpgrip1$^{-/-}$ null mice show photoreceptor defects (Zhao et al., 2003), but a kidney phenotype has not been described. Hif-1, a master regulator of several genes involved in oxygen homeostasis has been detected on the midpiece of the flagellum of spermatozoa (Marti et al., 2002). The function of Hif1 on this location is unknown, but since spermatozoa are transcriptionally inactive, a function as a transcription factor in sperm seems unlikely. Ctss, a lysosomal proteinase, has been implicated in promoting ciliar motility in airway epithelial cells (Chapman et al., 1997). Pcm1 is a component of centriolar satellites that are moved along microtubules toward the centrosomes. Pcm1 is also present in the fibrious granules, suggested to play an important role in centriolar replication during ciliogenesis, and ciliogenesis was induced in mouse nasal respiratory epithelial cells by the accumulation of Pcm1 at the apical pole (Kubo et al., 1999). Dctn3 and Dctn5 are components of the dynactin multisubunit protein complex required for cytoplasmic dynein activity, which is central to IFT (Schroer, 2004). Kif5b is associated with anterograde microtubule based transport in different processes (Hirokawa, 1998) and embryos of Kif5b$^{-/-}$ mice die at 9.5-11.5 dpc (Tanaka et al., 1998). Strong expression of TAZ at 15.5 dpc and downregulation of the above genes in TAZ$^{-/-}$ kidneys between 16.5 and 17.5 dpc is consistent with a role for TAZ in regulating these genes.

RT-PCR Analysis of Gene Expression

In addition to the microarray, we used conventional RT-PCR and real time PCR to look at the expression of the gene product of OFD1 (the gene mutated in oral-facial-digital syndrome. OFD1 mutations are accompanied by glomerular cysts (GCKD) (Ferrante, M. I., Barra, A., Truong, J. P., Banfi, S., Disteche, C. M., and Franco, B. (2003). Characterization of the OFD1/Ofd1 genes on the human and mouse sex chromosomes and exclusion of Ofd1 for the Xp1 mouse mutant. Genomics 81, 560-569; Ferrante, M. I., Giorgio, G., Feather, S. A., Bulfone, A., Wright, V., Ghiani, M., Selicorni, A., Gammaro, L., Scolari, F., Woolf, A. S., Sylvie, O., Bernard, L., Malcolm, S., Winter, R., Ballabio, A., and Franco, B. (2001).

Identification of the gene for oral-facial-digital type I syndrome. Am J Hum Genet 68, 569-576; Romio, L., Wright, V., Price, K., Winyard, P. J., Donnai, D., Porteous, M. E., Franco, B., Giorgio, G., Malcolm, S., Woolf, A. S., and Feather, S. A. (2003). OFD1, the gene mutated in oral-facial-digital syndrome type 1, is expressed in the metanephros and in human embryonic renal mesenchymal cells. J Am Soc Nephrol 14, 680-689). OFD1 expression is reduced to ~60% of normal in E 17.5 kidneys of TAZ$^{-/-}$ mice (FIG. 7). OFD1 mutations are dominant (i.e. inactivation of one copy is sufficient for the phenotype; this could correspond to the ~50% reduction in the TAZ$^{-/-}$ mice).

REFERENCES CITED IN EXAMPLE 3

Cantiello (2003). Trends Mol Med 9, 234-236.
Chapman et al (1997). Annu Rev Physiol 59, 63-88.
Gresh et al (2004). EMBO J 23, 1657-1668.
Hagiwara et al (2000). Med Electron Microsc 33, 109-114.
Hirokawa (1998). Science 279, 519-526.
Hong, et al (2001). J Biol Chem 276, 12091-12099.
Huangfu et al (2003). Nature 426, 83-87.
Kubo et al (1999). J Cell Biol 147, 969-980.
Lin et al (2003). Proc Natl Acad Sci USA 100, 5286-5291.
Marti et al (2002). Mol Endocrinol 16, 234-243.
Meindl et al (1996). Nat Genet 13, 35-42.
Moyer et al (1994). Science 264, 1329-1333.
Murcia et al (2000). Development 127, 2347-2355.
Naul et al (2003). Nat Genet 33, 129-137.
Orozco et al (1999). Nature 398, 674.
Otto et al (2003). Nat Genet 34, 413-420.
Pazour et al (2000). J Cell Biol 151, 709-718.
Pazour et al (2002). Polycystin-2 localizes to kidney cilia and the ciliary level is elevated in orpk mice with polycystic kidney disease. In: Curr Biol.
Pazour and Witman (2003). Curr Opin Cell Biol 15, 105-110.
Roepman et al (2000). Hum Mol Genet 9, 2095-2105.
Rosenbaum and Witman (2002). Nat Rev Mol Cell Biol 3, 813-825.
Schroer, T. A. (2004). Dynactin. Annu Rev Cell Dev Biol 20, 759-779.
Signor et al (1999). J Cell Biol 147, 519-530.
Tanaka et al (1998). Cell 93, 1147-1158.
Ward et al (2003). Hum Mol Genet 12, 2703-2710.
Watanabe et al (2003). Development 130, 1725-1734.
Yoder et al (2002). J Am Soc Nephrol 13, 2508-2516 Zhao et al (2003). Proc Natl Acad Sci USA 100, 3965-3970.

TABLE 2

110 up-regulated genes in 16.5 dpc embryonic kidney of Taz$^{-/-}$ mutant
Represented in mouse expression set 430A (Affymetrix)

| Public ID | Gene Symbol | Gene Title | Fold Change |
| --- | --- | --- | --- |
| BC027354.1 | A930025J12Rik | RIKEN cDNA A930025J12 gene | 17.1 |
| BC019726.1 | Paip1 | polyadenylate binding protein-interacting protein 1 | 17.1 |
| NM_029292.1 | 1700008F21Rik | RIKEN cDNA 1700008F21 gene | 14.9 |
| BC005446.1 | CAP, adenylate cyclase-associated protein 1 | 1417461_at | 9.2 |
| AA198774 | 5430428G01Rik | RIKEN cDNA 5430428G01 gene | 7.0 |
| AW536705 | Supt16h | suppressor of Ty 16 homolog (S. cerevisiae) | 6.5 |
| BC011158.1 | Serpina3m | serine (or cysteine) proteinase inhibitor, clade A, member 3M | 6.1 |
| NM_008440.1 | C630002N23Rik | RIKEN cDNA C630002N23 gene | 6.1 |
| NM_007598.1 | Cap1 | CAP, adenylate cyclase-associated protein 1 (yeast) | 5.7 |
| BM195235 | 2610042L04Rik | RIKEN cDNA 2610042L04 gene | 5.7 |
| BM233251 | uk* | uk | 5.3 |
| AK005276.1 | Trappc4 | trafficking protein particle complex 4 | 5.3 |
| AV172782 | uk | uk | 4.9 |
| BM195235 | 2610042L04Rik | RIKEN cDNA 2610042L04 gene | 4.3 |
| D86040.1 | Kcnj6 | potassium inwardly-rectifying channel, subfamily J, member 6 | 3.7 |
| BC023403.1 | 4632415L05Rik | RIKEN cDNA 4632415L05 gene | 3.2 |
| AW495875 | uk | uk | 3.2 |
| AF332006.1 | Slc25a2 | solute carrier family 25 (mitochondrial carrier, ornithine transporter) member 2 | 3.0 |

TABLE 2-continued 110 up-regulated genes in 16.5 dpc embryonic kidney of Taz$^{-/-}$ mutant
Represented in mouse expression set 430A (Affymetrix)

| Public ID | Gene Symbol | Gene Title | Fold Change |
|---|---|---|---|
| AV271979 | uk | uk | 3.0 |
| AV148191 | Hbb-y | hemoglobin Y, beta-like embryonic chain | 2.8 |
| AV329330 | Mapk11 | mitogen-activated protein kinase 11 | 2.8 |
| AK004734.1 | 1200013B08Rik | RIKEN cDNA 1200013B08 gene | 2.8 |
| NM_008511.1 | Lrmp | lymphoid-restricted membrane protein | 2.6 |
| BC025830.1 | 4732466D17Rik | RIKEN cDNA 4732466D17 gene | 2.6 |
| AV156860 | Hbb-y | hemoglobin Y, beta-like embryonic chain | 2.6 |
| NM_010498.1 | Ids | iduronate 2-sulfatase | 2.5 |
| BC010404.1 | Inhbe | inhibin beta E | 2.5 |
| AV251613 | C80638 | expressed sequence C80638 | 2.5 |
| BB350484 | Slc35c1 | solute carrier family 35, member C1 | 2.5 |
| AF394451.1 | Icoslg | icos ligand | 2.3 |
| AW413620 | MGI: 2180715 | glucocorticoid induced gene 1 | 2.1 |
| BQ032685 | Shoc2 | soc-2 (suppressor of clear) homolog (*C. elegans*) | 2.1 |
| NM_025748.1 | Deadc1 | deaminase domain containing 1 | 2.1 |
| BB757992 | Per3 | period homolog 3 (*Drosophila*) | 2.1 |
| NM_008221.1 | Hbb-y | hemoglobin Y, beta-like embryonic chain | 2.1 |
| NM_007781.1 | Csf2rb2 | colony stimulating factor 2 receptor, beta 2, low-affinity (granulocyte-macrophage) | 2.1 |
| NM_021392.1 | Ap4m1 | adaptor-related protein complex AP-4, mu 1 | 2.0 |
| BF608615 | Ywhaz | tyrosine 3-monooxygenase/tryptophan 5-monooxygenase activation protein, zeta polypeptide | 2.0 |
| BE333485 | Syp1 | synaptophysin-like protein | 2.0 |
| NM_013522.1 | Frg1 | FSHD region gene 1 | 2.0 |
| NM_013834.1 | Sfrp1 | secreted frizzled-related sequence protein 1 | 2.0 |
| NM_134141.1 | Ciapin1 | cytokine induced apoptosis inhibitor 1 | 2.0 |
| BC019393.1 | Car11 | carbonic anhydrase 11 | 2.0 |
| BM249463 | 2510049I19Rik | RIKEN cDNA 2510049I19 gene | 1.9 |
| AV025454 | Rad21 | RAD21 homolog (*S. pombe*) | 1.9 |
| BC012433.1 | Supt16h | suppressor of Ty 16 homolog (*S. cerevisiae*) | 1.9 |
| AK017392.1 | uk | uk | 1.9 |
| BG072739 | Sox11 | SRY-box containing gene 11 | 1.9 |
| AV256780 | uk | uk | 1.9 |
| NM_134141.1 | Ciapin1 | cytokine induced apoptosis inhibitor 1 | 1.9 |
| BC021831.1 | uk | uk | 1.9 |
| BG071068 | LOC433812 | LOC433812 | 1.7 |
| BB538325 | Ccnd1 | cyclin D1 | 1.7 |
| BI147855 | Comt | catechol-O-methyltransferase | 1.7 |
| NM_134052.1 | AL024210 | expressed sequence AL024210 | 1.7 |
| BC012424.1 | Elf5 | E74-like factor 5 | 1.7 |
| NM_026243.1 | 9130411I17Rik | RIKEN cDNA 9130411I17 gene | 1.7 |
| BC005552.1 | Asns | asparagine synthetase | 1.7 |
| BF451808 | Tfpi | tissue factor pathway inhibitor | 1.7 |
| NM_029693.1 | 1700123K08Rik | RIKEN cDNA 1700123K08 gene | 1.7 |
| NM_009264.1 | Sprr1a | small proline-rich protein 1A | 1.7 |
| AF069051.1 | Pttg1 | pituitary tumor-transforming 1 | 1.7 |
| BQ174328 | D6Ertd253e | DNA segment, Chr 6, ERATO Doi 253, expressed | 1.7 |
| AK012014.1 | 2610312E17Rik | 2610312E17 gene | 1.7 |
| BB006121 | MGC65558, 9030221M09Rik | similar to phosphatidylserine decarboxylase, RIKEN cDNA 9030221M09 gene | 1.6 |
| NM_007488.1 | Arnt2 | aryl hydrocarbon receptor nuclear translocator 2 | 1.6 |
| BF160591 | Prkcn | protein kinase C, nu | 1.6 |
| NM_024477.1 | AI428795 | expressed sequence AI428795 | 1.6 |
| BC024663.1 | Glo1 | glyoxalase 1 | 1.6 |
| AV105428 | Pttg1 | pituitary tumor-transforming 1 | 1.6 |
| BB550183 | Dbp | D site albumin promoter binding protein | 1.6 |
| AV209130 | Ppif | peptidylprolyl isomerase F (cyclophilin F) | 1.6 |
| AJ278133.1 | Kdelr2 | KDEL (Lys-Asp-Glu-Leu) endoplasmic reticulum protein retention receptor 2 | 1.6 |
| BC024643.1 | Alb1 | albumin 1 | 1.6 |
| BM207489 | 2610005L07Rik | RIKEN cDNA 2610005L07 gene | 1.6 |
| BB027848 | 4732466D17Rik | RIKEN cDNA 4732466D17 gene | 1.6 |
| NM_011638.1 | Tfrc | transferrin receptor | 1.6 |
| BE824681 | Zik1 | zinc finger protein interacting with K protein 1 | 1.6 |
| M26898.1 | Hba-x | hemoglobin X, alpha-like embryonic chain in Hba complex | 1.6 |
| NM_009325.1 | Tbxa2r | thromboxane A2 receptor | 1.6 |
| NM_133823.1 | Mmaa | methylmalonic aciduria (cobalamin deficiency) type A | 1.6 |
| NM_133721.1 | Itga9 | integrin alpha 9 | 1.6 |
| BC027196.1 | Pdk1 | pyruvate dehydrogenase kinase, isoenzyme 1 | 1.6 |
| AK012633.1 | uk | uk | 1.6 |
| AK002335.1 | Tpmt | thiopurine methyltransferase | 1.6 |
| BB810450 | Tfrc | transferrin receptor | 1.6 |
| AK004519.1 | Sh3bgrl | SH3-binding domain glutamic acid-rich protein like | 1.5 |

TABLE 2-continued

110 up-regulated genes in 16.5 dpc embryonic kidney of Taz$^{-/-}$ mutant
Represented in mouse expression set 430A (Affymetrix)

| Public ID | Gene Symbol | Gene Title | Fold Change |
|---|---|---|---|
| BC025493.1 | uk | uk | 1.5 |
| BC023114.1 | Slc27a4 | solute carrier family 27 (fatty acid transporter), member 4 | 1.5 |
| BB027654 | Cds2 | CDP-diacylglycerol synthase (phosphatidate cytidylyltransferase) 2 | 1.5 |
| AF395811.1 | Ssr1 | signal sequence receptor, alpha | 1.5 |
| BB504983 | MGC65558, 9030221M09Rik | similar to phosphatidylserine decarboxylase, RIKEN cDNA 9030221M09 gene | 1.5 |
| BC027196.1 | Pdk1 | pyruvate dehydrogenase kinase, isoenzyme 1 | 1.5 |
| NM_010441.1 | Hmga2 | high mobility group AT-hook 2 | 1.5 |
| BB253720 | P4ha1 | procollagen-proline, 2-oxoglutarate 4-dioxygenase (proline 4-hydroxylase), alpha 1 polypeptide | 1.5 |
| NM_011959.1 | Orc5l | origin recognition complex, subunit 5-like (*S. cerevisiae*) | 1.5 |
| NM_010905.1 | Nfia | nuclear factor I/A | 1.5 |
| BC002008.1 | Fabp5 | fatty acid binding protein 5, epidermal | 1.5 |
| BG064084 | Armc1 | armadillo repeat containing 1 | 1.5 |
| BM231738 | Hyou1 | hypoxia up-regulated 1 | 1.5 |
| NM_011765.1 | BC018101 | cDNA sequence BC018101 | 1.5 |
| BB761686 | Rock2 | Rho-associated coiled-coil forming kinase 2 | 1.5 |
| AF031467.1 | Bcat2 | branched chain aminotransferase 2, mitochondrial | 1.5 |
| BB477613 | E030034P13Rik | RIKEN cDNA E030034P13 gene | 1.5 |
| BB460904 | uk | uk | 1.5 |
| BB205930 | Nnt | nicotinamide nucleotide transhydrogenase | 1.5 |
| BB114402 | Lztr1 | leucine-zipper-like transcriptional regulator, 1 | 1.5 |
| AV174022 | Mme | Membrane metallo endopeptidase | 1.5 |
| BQ032797 | Mtmr4 | myotubularin related protein 4 | 1.5 |
| BC024663.1 | Glo1 | glyoxalase 1 | 1.5 |

*uk = unknown

TABLE 3

165 down-regulated genes in 16.5 dpc embryonic kidney of Taz$^{-/-}$ mutant
Represented in mouse expression set 430A (Affymetrix)

| Public ID | Gene Symbol | Gene Title | Fold change |
|---|---|---|---|
| BB535786 | Wwtr1 | WW domain containing transcription regulator 1 | −42.2 |
| AW763751 | BC005512 | cDNA sequence BC005512 | −22.6 |
| NM_023879.1 | Rpgrip1 | retinitis pigmentosa GTPase regulator interacting protein 1 | −17.1 |
| NM_007824.1 | Cyp7a1 | cytochrome P450, family 7, subfamily a, polypeptide 1 | −16.0 |
| BC002257.1 | BC005512 | cDNA sequence BC005512 | −13.9 |
| BM119774 | Cyp27b1 | cytochrome P450, family 27, subfamily b, polypeptide 1 | −11.3 |
| NM_009244.1 | uk* | uk | −10.6 |
| NM_026235.1 | 5430431G03Rik | RIKEN cDNA 5430431G03 gene | −9.8 |
| AK010101.1 | uk | uk | −7.5 |
| NM_020002.1 | Rec8L1 | REC8-like 1 (yeast) | −7.0 |
| AK011963.1 | Prdx2 | peroxiredoxin 2 | −5.7 |
| BC012512.1 | Srpr | signal recognition particle receptor ('docking protein') | −4.9 |
| BC004065.1 | uk | uk | −4.9 |
| NM_007618.1 | Serpina6 | serine (or cysteine) proteinase inhibitor, clade A, member 6 | −4.9 |
| NM_009243.1 | Serpina1a | serine (or cysteine) proteinase inhibitor, clade A, member 1a | −4.9 |
| AU046270 | uk | uk | −4.9 |
| BB396668 | Rab6b | RAB6B, member RAS oncogene family | −4.3 |
| AV382118 | Abcb10 | ATP-binding cassette, sub-family B (MDR/TAP), member 10 | −4.3 |
| BC027328.1 | Bst2 | bone marrow stromal cell antigen 2 | −4.0 |
| BB794742 | uk | uk | −3.732131966 |
| BC010754.1 | Klk6 | kallikrein 6 | −3.5 |
| BG297038 | uk | uk | −3.2 |
| BC010754.1 | Klk6 | kallikrein 6 | −3.2 |
| NM_030703.1 | Cpn1 | carboxypeptidase N, polypeptide 1 | −3.2 |
| AB056443.1 | D630002G06C730048C13Rik | hypothetical protein D630002G06, RIKEN cDNA C730048C13 gene | −3.0 |
| BF453369 | Rpl17 | ribosomal protein L17 | −3.0 |
| NM_011196.1 | Ptger3 | prostaglandin E receptor 3 (subtype EP3) | −3.0 |
| NM_009263.1 | Spp1 | secreted phosphoprotein 1 | −3.0 |
| AK012871.1 | 5730557B15Rik | RIKEN cDNA 5730557B15 gene | −3.0 |
| C76734 | Clcnka | chloride channel Ka | −2.8 |
| BB772272 | MGC102419 | similar to mNori-2p | −2.8 |
| BQ175355 | Kl | klotho | −2.8 |
| NM_025711.1 | Aspn | asporin | −2.8 |
| NM_008486.1 | Anpep | alanyl (membrane) aminopeptidase | −2.6 |
| AK004815.1 | Gucy1a3 | guanylate cyclase 1, soluble, alpha 3 | −2.6 |

TABLE 3-continued 165 down-regulated genes in 16.5 dpc embryonic kidney of Taz−/− mutant
Represented in mouse expression set 430A (Affymetrix)

| Public ID | Gene Symbol | Gene Title | Fold change |
|---|---|---|---|
| NM_009789.1 | S100g | S100 calcium binding protein G | −2.6 |
| U38261.1 | Sod3 | superoxide dismutase 3, extracellular | −2.6 |
| AW106920 | Pah | phenylalanine hydroxylase | −2.6 |
| BG862223 | uk | uk | −2.5 |
| AK017272.1 | Lpl | lipoprotein lipase | −2.5 |
| BC004747.1 | uk | uk | −2.3 |
| BB609699 | MGC41689 | hypothetical LOC211623 | −2.3 |
| AW108522 | Gatm | glycine amidinotransferase (L-arginine: glycine amidinotransferase) | −2.3 |
| BF580235 | Ctse | cathepsin E | −2.3 |
| NM_011521.1 | Sdc4 | syndecan 4 | −2.3 |
| X00686.1 | uk | uk | −2.3 |
| BB504826 | Fmod | fibromodulin | −2.1 |
| BE198116 | Ccl27 | chemokine (C—C motif) ligand 27 | −2.1 |
| X00686.1 | uk | uk | −2.1 |
| BG806300 | uk | uk | −2.1 |
| NM_028746.1 | Slc7a13 | solute carrier family 7, (cationic amino acid transporter, y+ system) member 13 | −2.1 |
| NM_023386.1 | uk | uk | −2.1 |
| AK018202.1 | 2310043N10Rik | RIKEN cDNA 2310043N10 gene | −2.143546925 |
| BC024112.1 | Aldob | aldolase 2, B isoform | −2.143546925 |
| NM_023125.1 | Kng1 | kininogen 1 | −2 |
| BB204486 | PhgdhLOC434252 | 3-phosphoglycerate dehydrogenase similar to 3-phosphoglycerate dehydrogenase | −2 |
| BG088656 | Pcm1 | pericentriolar material 1 | −2 |
| NM_023644.1 | Mccc1 | methylcrotonoyl-Coenzyme A carboxylase 1 (alpha) | −2 |
| NM_026320.1 | Gadd45gip1 | growth arrest and DNA-damage-inducible, gamma interacting protein 1 | −2 |
| NM_029562.1 | Cyp2d26 | cytochrome P450, family 2, subfamily d, polypeptide 26 | −2 |
| NM_026515.1 | 2810417H13Rik | RIKEN cDNA 2810417H13 gene | −2 |
| AW124853 | BC030183 | cDNA sequence BC030183 | −2 |
| NM_008161.1 | Gpx3 | glutathione peroxidase 3 | −2 |
| NM_021896.1 | Gucy1a3 | guanylate cyclase 1, soluble, alpha 3 | −2.0 |
| NM_009467.1 | Ugt2b5 | UDP-glucuronosyltransferase 2 family, member 5 | −2.0 |
| BE631223 | Pim1 | Proviral integration site 1 | −2.0 |
| NM_009063.1 | Rgs5 | regulator of G-protein signaling 5 | −2.0 |
| NM_134104.1 | uk | uk | −2.0 |
| BC026584.1 | Adhfe1 | ontaining, 1 | −1.9 |
| AA561726 | PhgdhLOC434252 | 3-phosphoglycerate dehydrogenase similar to 3-phosphoglycerate dehydrogenase | −1.9 |
| NM_019395.1 | Fbp1 | fructose bisphosphatase 1 | −1.9 |
| NM_080435.1 | Adcy4 | adenylate cyclase 4 | −1.9 |
| BB025231 | Nisch | nischarin | −1.9 |
| AF483504.1 | Myef2 | myelin basic protein expression factor 2, repressor | −1.9 |
| AW988981 | 1110008H02Rik | RIKEN cDNA 1110008H02 gene | −1.9 |
| BM899344 | Sycp3 | Synaptonemal complex protein 3 | −1.9 |
| NM_023422.1 | Hist1h2bc | histone 1, H2bc | −1.9 |
| BB025231 | Nisch | nischarin | −1.9 |
| BC022616.1 | 1810045K07Rik | RIKEN cDNA 1810045K07 gene | −1.9 |
| BB251205 | Gpr172b | G protein-coupled receptor 172B | −1.9 |
| X00686.1 | uk | uk | −1.9 |
| NM_010007.1 | Cyp2j5 | cytochrome P450, family 2, subfamily j, polypeptide 5 | −1.9 |
| NM_008911.1 | Ppox | protoporphyrinogen oxidase | −1.9 |
| AY075132.1 | Ifih1 | interferon induced with helicase C domain 1 | −1.9 |
| NM_013550.1 | Hist1h4h, Hist1h4c, Hist1h4i, Hist1h4j, Hist1h4k, Hist1h4m, Hist1h4a, Hist1h4b | histone 1, H4h, histone 1, H4c, histone 1, H4i, histone 1, H4j, histone 1, H4k, histone 1, H4m, histone 1, H4a, histone 1, H4b | −1.7 |
| NM_008597.1 | Mglap | matrix gamma-carboxyglutamate (gla) protein | −1.7 |
| BQ173888 | 6430706D22Rik | RIKEN cDNA 6430706D22 gene | −1.7 |
| NM_010174.1 | Fabp3 | fatty acid binding protein 3, muscle and heart | −1.7 |
| NM_019565.1 | Zfp386 | zinc finger protein 386 (Kruppel-like) | −1.7 |
| BB745805 | BC031140 | cDNA sequence BC031140 | −1.7 |
| NM_008294.1 | Hsd3b4 | hydroxysteroid dehydrogenase-4, delta<5>-3-beta | −1.7 |
| BM248225 | 6430706D22Rik | RIKEN cDNA 6430706D22 gene | −1.7 |
| NM_025956.1 | 1700011H14Rik | RIKEN cDNA 1700011H14 gene | −1.7 |
| BC021458.1 | Sostdc1 | sclerostin domain containing 1 | −1.7 |
| AK013851.1 | 2900097C17Rik | RIKEN cDNA 2900097C17 gene | −1.7 |
| NM_008509.1 | Lpl | lipoprotein lipase | −1.7 |
| NM_031192.1 | Ren1 | renin 1 structural | −1.7 |
| BC016208.1 | Hdac11 | histone deacetylase 11 | −1.7 |
| BB127697 | D630002G06C730048C13Rik | hypothetical protein D630002G06 RIKEN cDNA C730048C13 gene | −1.7 |
| NM_026127.1 | uk | uk | −1.7 |
| NM_133736.1 | uk | uk | −1.7 |
| AF480860.1 | Elovl6 | ELOVL family member 6, elongation of long chain fatty acids (yeast) | −1.7 |

TABLE 3-continued

165 down-regulated genes in 16.5 dpc embryonic kidney of Taz$^{-/-}$ mutant
Represented in mouse expression set 430A (Affymetrix)

| Public ID | Gene Symbol | Gene Title | Fold change |
|---|---|---|---|
| BE686792 | uk | Similar to erythroid differentiation regulator | −1.7 |
| BC013442.1 | uk | uk | −1.6 |
| NM_009196.1 | Slc16a1 | solute carrier family 16 (monocarboxylic acid transporters), member 1 | −1.6 |
| BC008220.1 | Esco1 | establishment of cohesion 1 homolog 1 (*S. cerevisiae*) | −1.6 |
| AK004748.1 | Riok3 | RIO kinase 3 (yeast) | −1.6 |
| AK006478.1 | Dnajb4 | DnaJ (Hsp40) homolog, subfamily B, member 4 | −1.6 |
| NM_021537.1 | Stk25 | serine/threonine kinase 25 (yeast) | −1.6 |
| NM_020010.1 | uk | uk | −1.6 |
| NM_007563.1 | Bpgm | 2,3-bisphosphoglycerate mutase | −1.6 |
| NM_029269.1 | Spp2 | secreted phosphoprotein 2 | −1.6 |
| BE534815 | Gfra1 | glial cell line derived neurotrophic factor family receptor alpha 1 | −1.6 |
| BG070342 | Cpeb4 | cytoplasmic polyadenylation element binding protein 4 | −1.6 |
| BI555209 | Dysf, Fer1l3 | dysferlin, fer-1-like 3, myoferlin (*C. elegans*) | −1.6 |
| BB705380 | Hmgcs1 | 3-hydroxy-3-methylglutaryl-Coenzyme A synthase 1 | −1.6 |
| BF166000 | Hmgb1, 4932431P20Rik, LOC433179 | high mobility group box 1, RIKEN cDNA 4932431P20 gene, similar to Ac2-008 | −1.6 |
| BC013542.1 | MGI: 1914432 | membrane-associated protein 17 | −1.6 |
| NM_026179.1 | Abhd5 | abhydrolase domain containing 5 | −1.6 |
| BB409788 | Chd8 | chromodomain helicase DNA binding protein 8 | −1.6 |
| NM_013750.1 | Phlda3 | pleckstrin homology-like domain, family A, member 3 | −1.6 |
| AK006418.1 | Arl2bp | ADP-ribosylation factor-like 2 binding protein | −1.6 |
| NM_011294.1 | Rpo2tc1 | RNA polymerase II transcriptional coactivator | −1.6 |
| BC006680.1 | Ubc | ubiquitin C | −1.6 |
| NM_007398.1 | Ada | adenosine deaminase | −1.6 |
| AK004165.1 | Rgs5 | regulator of G-protein signaling 5 | −1.6 |
| M25487.1 | Hist1h2bc, Hist1h2be, Hist1h2bl, Hist1h2bm, Hist1h2bp, LOC432734 | histone 1, H2bc, histone 1, H2be, histone 1, H2bl, histone 1, H2bm, histone 1, H2bp, similar to Hist1h2bc protein | −1.5 |
| BQ176661 | Mkrn1 | makorin, ring finger protein, 1 | −1.5 |
| AA798895 | uk | uk | −1.5 |
| NM_011794.1 | Bpnt1 | bisphosphate 3'-nucleotidase 1 | −1.5 |
| U08020.1 | Col1a1 | procollagen, type I, alpha 1 | −1.5 |
| BC010275.1 | Arpc1b | actin related protein 2/3 complex, subunit 1B | −1.5 |
| NM_026423.1 | 2410018C20Rik | RIKEN cDNA 2410018C20 gene | −1.5 |
| BB469763 | uk | uk | −1.5 |
| AF109137.1 | Hdc | histidine decarboxylase | −1.5 |
| NM_009994.1 | Cyp1b1 | cytochrome P450, family 1, subfamily b, polypeptide 1 | −1.5 |
| BC003264.1 | Enpp2 | ectonucleotide pyrophosphatase/phosphodiesterase 2 | −1.5 |
| AV066625 | Lzp-s | P lysozyme structural | −1.5 |
| BB404569 | 2810421I24Rik | RIKEN cDNA 2810421I24 gene | −1.5 |
| NM_011216.1 | Ptpro | protein tyrosine phosphatase, receptor type, O | −1.5 |
| AK011784.1 | Igfbp2 | insulin-like growth factor binding protein 2 | −1.5 |
| AV209892 | Pkig | protein kinase inhibitor, gamma | −1.5 |
| AW553304 | Bach2 | BTB and CNC homology 2 | −1.5 |
| J05186.1 | Cai | calcium binding protein, intestinal | −1.5 |
| BC012637.1 | Aadat | aminoadipate aminotransferase | −1.5 |
| NM_010151.1 | Nr2f1 | nuclear receptor subfamily 2, group F, member 1 | −1.5 |
| NM_007647.1 | Entpd5 | ectonucleoside triphosphate diphosphohydrolase 5 | −1.5 |
| BC026055.1 | Shmt1 | serine hydroxymethyl transferase 1 (soluble) | −1.5 |
| BF140275 | Clta | clathrin, light polypeptide (Lca) | −1.5 |
| BC019882.1 | MGC29978 | -ketoacyl-CoA thiolase B | −1.5 |
| NM_011335.1 | Ccl21b, Ccl21a, Ccl21c | chemokine (C—C motif) ligand 21b (serine), chemokine (C—C motif) ligand 21a (leucine), chemokine (C—C motif) ligand 21c (leucine) | −1.5 |
| BC016255.1 | Pla2g4b | phospholipase A2, group IVB (cytosolic) | −1.5 |
| BB004104 | uk | uk | −1.5 |
| NM_011213.1 | Ptprf | protein tyrosine phosphatase, receptor type, F | −1.5 |
| AK014312.1 | Lum | lumican | −1.5 |
| BC013446.1 | Pthr1 | parathyroid hormone receptor 1 | −1.5 |
| BC020031.1 | S100a16 | S100 calcium binding protein A16 | −1.5 |
| NM_007714.1 | Clk4 | CDC like kinase 4 | −1.5 |
| NM_010125.1 | Elf5 | E74-like factor 5 | −1.5 |
| BF322712 | Bdh | -hydroxybutyrate dehydrogenase (heart, mitochondrial) | −1.5 |
| BF235516 | Ptprf | protein tyrosine phosphatase, receptor type, F | −1.5 |
| AI325305 | Mmp14 | matrix metalloproteinase 14 (membrane-inserted) | −1.5 |
| BC004589.1 | Bpgm | 2,3-bisphosphoglycerate mutase | −1.5 |
| NM_018858.1 | Pbp | phosphatidylethanolamine binding protein | −1.5 |
| AF197159.1 | Cubn | cubilin (intrinsic factor-cobalamin receptor) | −1.5 |

*uk = unknown

TABLE 4

72 up-regulated genes in 16.5 dpc embryonic kidney of Taz−/− mutant
Represented in mouse expression set 430B (Affymetrix)

| Public ID | Gene Symbol | Gene Title | Fold Change |
|---|---|---|---|
| BB381990 | 6230403H02Rik | RIKEN cDNA 6230403H02 gene | 36.8 |
| BB479245 | 9430092A03Rik | RIKEN cDNA 9430092A03 gene | 34.2967508 |
| BM117463 | D430039N05Rik | RIKEN cDNA D430039N05 gene | 19.69831061 |
| BM123923 | uk* | uk | 16.0 |
| BI900756 | C78541 | expressed sequence C78541 | 14.9 |
| AK020714.1 | A230105L22Rik | RIKEN cDNA A230105L22 gene | 14.9 |
| AV253991 | 4933403H06Rik | RIKEN cDNA 4933403H06 gene | 13.9 |
| AV244034 | uk | uk | 13.9 |
| AV331592 | Got2 | glutamate oxaloacetate transaminase 2, mitochondrial | 13.0 |
| AK017737.1 | Leng4 | leukocyte receptor cluster (LRC) member 4 | 11.3 |
| BB127276 | Chd7 | chromodomain helicase DNA binding protein 7 | 11.3 |
| BB553937 | 2500001H09Rik | RIKEN cDNA 2500001H09 gene | 10.6 |
| BB468437 | uk | uk | 10.6 |
| AW494764 | uk | uk | 9.8 |
| BM233846 | uk | uk | 8.6 |
| BB371241 | Pik4cb | phosphatidylinositol 4-kinase, catalytic, beta polypeptide | 8.0 |
| BB437157 | uk | uk | 6.5 |
| AV376713 | 9130214F15Rik | RIKEN cDNA 9130214F15 gene | 6.1 |
| BB667699 | Rcor3 | REST corepressor 3 | 6.1 |
| BB821609 | Drbp1 | developmentally regulated RNA binding protein 1 | 5.7 |
| BB626803 | Fnbp3 | formin binding protein 3 | 4.28709385 |
| AK015014.1 | Wdr20 | WD repeat domain 20 | 4.0 |
| BB075402 | 9330107J05Rik | RIKEN cDNA 9330107J05 gene | 4.0 |
| AV099154 | BC030477 | cDNA sequence BC030477 | 3.7 |
| BM508495 | 6230403H02Rik | RIKEN cDNA 6230403H02 gene | 3.7 |
| AK013061.1 | Cecr2 | cat eye syndrome chromosome region, candidate 2 homolog (human) | 3.7 |
| BF682848 | BC055107 | cDNA sequence BC055107 | 3.7 |
| BB326329 | Nipa1 | non imprinted in Prader-Willi/Angelman syndrome 1 homolog (human) | 3.5 |
| BM248385 | | uk | 3.5 |
| BB424591 | 4930578F03Rik | RIKEN cDNA 4930578F03 gene | 2.8 |
| BI793814 | Ccm1 | cerebral cavernous malformations 1 | 2.8 |
| BB238604 | 5730547N13Rik | RIKEN cDNA 5730547N13 gene | 2.5 |
| BM213590 | uk | uk | 2.5 |
| AV175699 | Spata7 | spermatogenesis associated 7 | 2.5 |
| BB178550 | Nyx | nyctalopin | 2.5 |
| BM243674 | Gm457 | gene model 457, (NCBI) | 2.462288827 |
| BF682848 | BC055107 | cDNA sequence BC055107 | 2.29739671 |
| BE685845 | uk | uk | 2.29739671 |
| AK007233.1 | 5730409G07Rik | RIKEN cDNA 5730409G07 gene | 2.143546925 |
| AK014287.1 | 4930429M06Rik | RIKEN cDNA 4930429M06Rik | 2.143546925 |
| BB703667 | A430031N04 | hypothetical protein A430031N04 | 2.143546925 |
| BB016769 | Atp10d | ATPase, Class V, type 10D | 2.1 |
| AK017384.1 | Kctd6 | potassium channel tetramerisation domain containing 6 | 2.0 |
| AV319507 | Mmrn2 | multimerin 2 | 2.0 |
| BB758432 | Dixdc1 | DIX domain containing 1 | 2.0 |
| BI076810 | uk | uk | 2.0 |
| BB417360 | 5730469D23Rik | RIKEN cDNA 5730469D23 gene | 2.0 |
| BG064541 | uk | uk | 2.0 |
| BB795363 | uk | uk | 2.0 |
| BB212045 | 9230110M18Rik | RIKEN cDNA 9230110M18 gene | 2.0 |
| AI841578 | Ddn | dendrin | 1.9 |
| AV161107 | 6230403H02Rik | RIKEN cDNA 6230403H02 gene | 1.9 |
| BB728354 | Brpf3 | Bromodomain and PHD finger containing, 3 | 1.9 |
| AK002767.1 | 1600029D21Rik | RIKEN cDNA 1600029D21 gene | 1.9 |
| BM200103 | 1600010D10Rik | RIKEN cDNA 1600010D10 gene | 1.9 |
| AV375328 | AI987692 | expressed sequence AI987692 | 1.9 |

*uk = unknown

TABLE 5

51 down-regulated genes in 16.5 dpc embryonic kidney of Taz−/− mutant
Represented in mouse expression set 430B (Affymetrix)

| Public ID | Gene Symbol | Gene Title | Fold Change |
|---|---|---|---|
| BG071399 | uk* | uk | −55.7 |
| BB070264 | Wt1 | RIKEN cDNA D630046I19 gene | −29.9 |
| BG063053 | uk | uk | −19.7 |
| BG073178 | Mid1 | Midline 1 | −18.4 |

TABLE 5-continued

51 down-regulated genes in 16.5 dpc embryonic kidney of Taz$^{-/-}$ mutant
Represented in mouse expression set 430B (Affymetrix)

| Public ID | Gene Symbol | Gene Title | Fold Change |
|---|---|---|---|
| AW493252 | Gm22 | Gene model 22, (NCBI) | −13.0 |
| AK016248.1 | 4930568D16Rik | RIKEN cDNA 4930568D16 gene | −12.1 |
| BB204106 | uk | uk | −8.6 |
| BB128256 | Abca5 | ATP-binding cassette, sub-family A (ABC1), member 5 | −8.0 |
| BB099116 | 1110002E22Rik | RIKEN cDNA 1110002E22 gene | −6.5 |
| BB066105 | uk | uk | −5.7 |
| BG066776 | uk | uk | −5.3 |
| BB022341 | Brd7 | bromodomain containing 7 | −4.9 |
| BI730538 | Dnajc6 | DnaJ (Hsp40) homolog, subfamily C, member 6 | −4.6 |
| BF018182 | C330005L02Rik | RIKEN cDNA C330005L02 gene | −4.3 |
| AI647966 | uk | uk | −4.3 |
| BB656631 | 6230403H02Rik | RIKEN cDNA 1110038H03 gene | −4.0 |
| AV321065 | 1110051B16Rik | RIKEN cDNA 1110051B16 gene | −3.5 |
| AK020406.1 | Gabpb2 | GA repeat binding protein, beta 2 | −3.2 |
| BB051012 | 6720422M22Rik | RIKEN cDNA 6720422M22 gene | −3.2 |
| AK012253.1 | 2700017A04Rik | RIKEN cDNA 2700017A04 gene | −3.0 |
| AI875033 | uk | uk | −3.0 |
| AK019514.1 | 4833413E03Rik | RIKEN cDNA 4833413E03 gene | −2.8 |
| BM939312 | uk | uk | −2.8 |
| AV122561 | 9330177P20Rik | RIKEN cDNA 9330177P20 gene | −2.8 |
| BF662057 | Xrn1 | RIKEN cDNA A130001C09 gene | −2.8 |
| BG072279 | D14Ertd449e | DNA segment, Chr 14, ERATO Doi 449, expressed | −2.8 |
| BG070110 | uk | uk | −2.8 |
| BB036922 | 1500011J06Rik | RIKEN cDNA 1500011J06 gene | −2.6 |
| BB400326 | 4930538D17Rik | RIKEN cDNA 4930538D17 gene | −2.6 |
| BB318702 | A730017C20Rik | RIKEN cDNA A730017C20 gene | −2.6 |
| AI642171 | Pgpep1 | pyroglutamyl-peptidase I | −2.6 |
| AV277495 | D830007B15Rik | RIKEN cDNA D830007B15 gene | −2.5 |
| AV277364 | 4932413O14Rik | RIKEN cDNA 4932413O14 gene | −2.5 |
| X00686.1 | uk | uk | −2.5 |
| BB535044 | AK129018 | cDNA sequence AK129018 | −2.462288827 |
| X00686.1 | uk | uk | −2.5 |
| BB245618 | Tmem25 | transmembrane protein 25 | −2.5 |
| BB699957 | Mtus1 | mitochondrial tumor suppressor 1 | −2.3 |
| BB283960 | uk | uk | −2.3 |
| BM209908 | D14Abb1e | DNA segment, Chr 14, Abbott 1 expressed | −2.1 |
| X00686.1 | uk | uk | −2.1 |
| AA409309 | Efhd2 | EF hand domain containing 2 | −2.0 |
| AV301944 | uk | uk | −2.0 |
| AK009885.1 | Glcci1 | glucocorticoid induced transcript 1 | −2.0 |
| BM118120 | uk | uk | −1.9 |
| AK009502.1 | Tia1 | cytotoxic granule-associated RNA binding protein 1 | −1.9 |
| AI790225 | Nphs2 | nephrosis 2 homolog, podocin (human) | −1.9 |
| BM244064 | Tde1 | tumor differentially expressed 1 | −1.9 |
| AV308092 | Cdgap | Cdc42 GTPase-activating protein | −1.7 |
| BI900109 | BC037095 | cDNA sequence BC037095 | −1.7 |
| AK004327.1 | 1110060I01Rik | RIKEN cDNA 1110060I01 gene | −1.7 |

*uk = unknown

TABLE 6

143 up-regulated genes in 17.5 dpc embryonic kidney of Taz$^{-/-}$ mutant
Represented in mouse expression set 430A (Affymetrix)

| Public ID | Gene symbol | Gene title | Fold change |
|---|---|---|---|
| BB087946 | Rac1 | RAS-related C3 botulinum substrate 1 | 34.3 |
| NM_008846.1 | Pip5k1a | phosphatidylinositol-4-phosphate 5-kinase, type 1 alpha | 18.4 |
| NM_025777.1 | 9030623N16Rik | RIKEN cDNA 9030623N16 gene | 18.4 |
| BC023403.1 | 4632415L05Rik | RIKEN cDNA 4632415L05 gene | 9.2 |
| BC005446.1 | Cap1 | CAP, adenylate cyclase-associated protein 1 (yeast) | 7.5 |
| AV026617 | Fos | FBJ osteosarcoma oncogene | 6.5 |
| AW413620 | Gig1 | glucocorticoid induced gene 1 | 6.5 |
| NM_007598.1 | Cap1 | CAP, adenylate cyclase-associated protein 1 (yeast) | 5.7 |
| AW536705 | Supt16h | suppressor of Ty 16 homolog (S. cerevisiae) | 5.3 |
| AA210261 | Ddx3y | DEAD (Asp-Glu-Ala-Asp) box polypeptide 3, Y-linked | 5.3 |
| AW106963 | Pck1 | phosphoenolpyruvate carboxykinase 1, cytosolic | 4.9 |
| BC027354.1 | A930025J12Rik | RIKEN cDNA A930025J12 gene | 4.6 |
| BM195235 | 2610042L04Rik | RIKEN cDNA 2610042L04 gene | 4.6 |

TABLE 6-continued 143 up-regulated genes in 17.5 dpc embryonic kidney of Taz−/− mutant
Represented in mouse expression set 430A (Affymetrix)

| Public ID | Gene symbol | Gene title | Fold change |
|---|---|---|---|
| NM_133232.1 | Pfkfb3 | 6-phosphofructo-2-kinase/fructose-2,6-biphosphatase 3 | 4.3 |
| NM_012011.1 | uk* | uk | 4.3 |
| BC013493.1 | Slc13a2 | solute carrier family 13 (sodium-dependent dicarboxylate transporter), member 2 | 4.3 |
| BC014724.1 | 1810022C23Rik | RIKEN cDNA 1810022C23 gene | 4.0 |
| BM195235 | 2610042L04Rik | RIKEN cDNA 2610042L04 gene | 4.0 |
| BG072739 | Sox11 | SRY-box containing gene 11 | 3.5 |
| BB667072 | Ddx3y | DEAD (Asp-Glu-Ala-Asp) box polypeptide 3, Y-linked | 3.0 |
| NM_054094.4 | Bucs1 | butyryl Coenzyme A synthetase 1 | 3.0 |
| NM_011171.1 | Procr | protein C receptor, endothelial | 2.8 |
| AW495875 | uk | uk | 2.8 |
| BM233251 | uk | uk | 2.8 |
| NM_010594.1 | Kap | kidney androgen regulated protein | 2.8 |
| AJ007376.1 | Ddx3y | DEAD (Asp-Glu-Ala-Asp) box polypeptide 3, Y-linked | 2.6 |
| BC005679.1 | Sdc4 | syndecan 4 | 2.6 |
| NM_013834.1 | Sfrp1 | secreted frizzled-related sequence protein 1 | 2.5 |
| NM_011726.1 | Xlr3a | X-linked lymphocyte-regulated 3a | 2.5 |
| AF031467.1 | Bcat2 | branched chain aminotransferase 2, mitochondrial | 2.5 |
| NM_013522.1 | Frg1 | FSHD region gene 1 | 2.3 |
| BC018236.1 | Alad | aminolevulinate, delta-, dehydratase | 2.3 |
| NM_053094.1 | Cd163 | CD163 antigen | 2.3 |
| NM_010905.1 | uk | uk | 2.3 |
| NM_024228.1 | 1110015E22Rik | RIKEN cDNA 1110015E22 gene | 2.1 |
| NM_008259.1 | Foxa1 | forkhead box A1 | 2.1 |
| NM_010594.1 | Kap | kidney androgen regulated protein | 2.1 |
| BB497312 | Slc13a3 | solute carrier family 13 (sodium-dependent dicarboxylate transporter), member 3 | 2.1 |
| NM_007962.1 | Eva1 | epithelial V-like antigen 1 | 2.1 |
| BQ032685 | Shoc2 | soc-2 (suppressor of clear) homolog (*C. elegans*) | 2.1 |
| NM_021375.1 | Rhbg | Rhesus blood group-associated B glycoprotein | 2.0 |
| NM_025748.1 | Deadc1 | deaminase domain containing 1 | 2.0 |
| NM_009647.1 | uk | uk | 2.0 |
| BC010747.1 | BC013476 | cDNA sequence BC013476 | 2.0 |
| NM_013822.1 | Jag1 | jagged 1 | 2.0 |
| AF365876.1 | 1110032A04Rik | RIKEN cDNA 1110032A04 gene | 2.0 |
| BB538325 | Ccnd1 | cyclin D1 | 2.0 |
| BC027206.1 | Hnrpl | heterogeneous nuclear ribonucleoprotein L | 2.0 |
| AA880220 | Jag1 | jagged 1 | 2.0 |
| X13721.1 | Hoxb8 | homeo box B8 | 1.9 |
| NM_010176.1 | Fah | fumarylacetoacetate hydrolase | 1.9 |
| AI303435 | Slc1a4 | solute carrier family 1 (glutamate/neutral amino acid transporter), member 4 | 1.9 |
| NM_023478.1 | Upk3a | uroplakin 3A | 1.9 |
| BC023116.1 | Cgref1 | cell growth regulator with EF hand domain 1 | 1.9 |
| BC026439.1 | BC026439 | cDNA sequence BC026439 | 1.9 |
| BM214378 | Cds2 | CDP-diacylglycerol synthase (phosphatidate cytidylyltransferase) 2 | 1.9 |
| BB811478 | Npm3 | nucleoplasmin 3 | 1.9 |
| BC025618.1 | Atp1a1 | ATPase, Na+/K+ transporting, alpha 1 polypeptide | 1.9 |
| NM_024477.1 | AI428795 | expressed sequence AI428795 | 1.9 |
| BM249463 | 2510049I19Rik | RIKEN cDNA 2510049I19 gene | 1.9 |
| AW105774 | Napsa | napsin A aspartic peptidase | 1.9 |
| NM_008812.1 | Padi2 | peptidyl arginine deiminase, type II | 1.9 |
| BC025618.1 | Atp1a1 | ATPase, Na+/K+ transporting, alpha 1 polypeptide | 1.9 |
| NM_008681.1 | Ndrl | N-myc downstream regulated-like | 1.9 |
| NM_008217.2 | Has3 | hyaluronan synthase 3 | 1.9 |
| NM_009264.1 | Sprr1a | small proline-rich protein 1A | 1.9 |
| AA560093 | Ramp2 | receptor (calcitonin) activity modifying protein 2 | 1.7 |
| BC012433.1 | Supt16h | suppressor of Ty 16 homolog (*S. cerevisiae*) | 1.7 |
| BI964347 | Adam12 | a disintegrin and metalloproteinase domain 12 (meltrin alpha) | 1.7 |
| AJ278133.1 | Kdelr2 | KDEL (Lys-Asp-Glu-Leu) endoplasmic reticulum protein retention receptor 2 | 1.7 |
| NM_015736.1 | Galnt3 | UDP-N-acetyl-alpha-D-galactosamine:polypeptide N-acetylgalactosaminyltransferase 3 | 1.7 |
| NM_010022.1 | Dbt | dihydrolipoamide branched chain transacylase E2 | 1.7 |
| X57349.1 | Tfrc | transferrin receptor | 1.7 |
| BC017691.1 | Slc5a8 | solute carrier family 5 (iodide transporter), member 8 | 1.7 |
| NM_008339.1 | Cd79b | CD79B antigen | 1.7 |
| NM_029550.1 | Keg1 | kidney expressed gene 1 | 1.7 |
| NM_009647.1 | uk | uk | 1.7 |
| BC024495.1 | Sfrp1 | secreted frizzled-related sequence protein 1 | 1.7 |
| NM_023649.1 | Ush1c | Usher syndrome 1C homolog (human) | 1.6 |
| NM_134052.1 | AL024210 | expressed sequence AL024210 | 1.6 |
| BM213176 | uk | uk | 1.6 |

TABLE 6-continued 143 up-regulated genes in 17.5 dpc embryonic kidney of Taz$^{-/-}$ mutant
Represented in mouse expression set 430A (Affymetrix)

| Public ID | Gene symbol | Gene title | Fold change |
|---|---|---|---|
| BC011229.1 | Fmo1 | flavin containing monooxygenase 1 | 1.6 |
| NM_019703.1 | Pfkp | phosphofructokinase, platelet | 1.6 |
| BC002008.1 | Fabp5 | fatty acid binding protein 5, epidermal | 1.6 |
| NM_026030.1 | Eif2s2 | eukaryotic translation initiation factor 2, subunit 2 (beta) | 1.6 |
| BI684958 | Epb4.1l1 | erythrocyte protein band 4.1-like 1 | 1.6 |
| AF282864.1 | CRG-L1 | cancer related gene-liver 1 | 1.6 |
| NM_008878.1 | Serpinf2 | serine (or cysteine) proteinase inhibitor, clade F, member 2 | 1.6 |
| M21836.1 | Krt2-8 | keratin complex 2, basic, gene 8 | 1.6 |
| NM_134157.1 | Atp6v1b1 | ATPase, H+ transporting, V1 subunit B, isoform 1 | 1.6 |
| BM208582 | Hiat1 | hippocampus abundant gene transcript 1 | 1.6 |
| AF177211.1 | P2ry14 | purinergic receptor P2Y, G-protein coupled, 14 | 1.6 |
| BC021384.1 | Slc22a19 | solute carrier family 22 (organic anion transporter), member 19 | 1.6 |
| BB114067 | Tagln | transgelin | 1.6 |
| BB540658 | Fstl1 | follistatin-like 1 | 1.6 |
| NM_031170.1 | Krt2-8 | keratin complex 2, basic, gene 8 | 1.6 |
| BM207489 | 2610005L07Rik | RIKEN cDNA 2610005L07 gene | 1.6 |
| BM200153 | D930016D06Rik | RIKEN cDNA D930016D06 gene | 1.6 |
| BC024479.1 | BC024479 | cDNA sequence BC024479 | 1.6 |
| AB029929.1 | Cav1 | caveolin, caveolae protein 1 | 1.6 |
| BG868120 | Src | Rous sarcoma oncogene | 1.6 |
| AF117613.1 | Hebp1 | heme binding protein 1 | 1.6 |
| NM_011638.1 | Tfrc | transferrin receptor | 1.6 |
| NM_019395.1 | Fbp1 | fructose bisphosphatase 1 | 1.6 |
| BC021759.1 | Sp2 | Sp2 transcription factor | 1.6 |
| AK011596.1 | Tfrc | transferrin receptor | 1.6 |
| NM_030714.1 | Dtx3 | deltex 3 homolog (*Drosophila*) | 1.6 |
| AB030038.1 | Acp6 | acid phosphatase 6, lysophosphatidic | 1.6 |
| BI452653 | Zfp106 | zinc finger protein 106 | 1.6 |
| NM_008586.1 | Mep1b | meprin 1 beta | 1.5 |
| AK009249.1 | 2310009E04Rik | RIKEN cDNA 2310009E04 gene | 1.5 |
| NM_026183.1 | 1300013J15Rik | RIKEN cDNA 1300013J15 gene | 1.5 |
| BI150320 | Rnf11 | ring finger protein 11 | 1.5 |
| NM_007494.1 | Ass1 | argininosuccinate synthetase 1 | 1.5 |
| BC022950.1 | 1600029D21Rik | RIKEN cDNA 1600029D21 gene | 1.5 |
| AV297961 | 5730453H04Rik | RIKEN cDNA 5730453H04 gene | 1.5 |
| NM_008182.1 | uk | uk | 1.5 |
| NM_022024.1 | Gmfg | glia maturation factor, gamma | 1.5 |
| BG919998 | Stk39 | serine/threonine kinase 39, STE20/SPS1 homolog (yeast) | 1.5 |
| BC015285.1 | Trub2 | TruB pseudouridine (psi) synthase homolog 2 (*E. coli*) | 1.5 |
| AW047304 | Bckdhb | branched chain ketoacid dehydrogenase E1, beta polypeptide | 1.5 |
| BM209618 | Slc2a1 | solute carrier family 2 (facilitated glucose transporter), member 1 | 1.5 |
| AF085144.1 | Papss2 | 3'-phosphoadenosine 5'-phosphosulfate synthase 2 | 1.5 |
| BC027196.1 | Pdk1 | pyruvate dehydrogenase kinase, isoenzyme 1 | 1.5 |
| AW537061 | Snapc3 | small nuclear RNA activating complex, polypeptide 3 | 1.5 |
| BM207588 | Slc2a1 | solute carrier family 2 (facilitated glucose transporter), member 1 | 1.5 |
| BC023177.1 | Adprhl2 | ADP-ribosylhydrolase like 2 | 1.5 |
| BG070342 | Cpeb4 | cytoplasmic polyadenylation element binding protein 4 | 1.5 |
| BC027371.1 | 5830411E10Rik | RIKEN cDNA 5830411E10 gene | 1.5 |
| BC025145.1 | Ptprd | protein tyrosine phosphatase, receptor type, D | 1.5 |
| AK006269.1 | Pdzk1 | PDZ domain containing 1 | 1.5 |
| AI788952 | Idh1 | isocitrate dehydrogenase 1 (NADP+), soluble | 1.5 |
| BG072171 | Hdc | histidine decarboxylase | 1.5 |
| NM_009760.1 | Bnip3 | BCL2/adenovirus E1B 19 kDa-interacting protein 1, NIP3 | 1.5 |
| BE134496 | Safb2 | scaffold attachment factor B2 | 1.5 |
| NM_010497.1 | Idh1 | isocitrate dehydrogenase 1 (NADP+), soluble | 1.5 |
| BB193413 | Aqp4 | aquaporin 4 | 1.5 |
| BG072100 | Chdh | choline dehydrogenase | 1.5 |
| NM_019701.1 | Clcnkb | chloride channel Kb | 1.5 |
| NM_008182.1 | Gsta2 | glutathione S-transferase, alpha 2 (Yc2) | 1.5 |
| BI690696 | Hmgcs1 | 3-hydroxy-3-methylglutaryl-Coenzyme A synthase 1 | 1.5 |
| AK007630.1 | Cdkn1a | cyclin-dependent kinase inhibitor 1A (P21) | 1.5 |
| NM_013464.1 | uk | uk | 1.5 |

*uk = unknown

TABLE 7

163 down-regulated genes in 17.5 dpc embryonic kidney of Taz$^{-/-}$ mutant
Represented in mouse expression set 430A (Affymetrix)

| Public ID | Gene symbol | Gene title | Fold change |
|---|---|---|---|
| BB535786 | 2310058J06Rik | RIKEN cDNA 2310058J06 gene | −52.0 |
| BC004065.1 | uk* | uk | −45.3 |
| NM_023879.1 | Rpgrip1 | retinitis pigmentosa GTPase regulator interacting protein 1 | −42.2 |
| NM_017391.1 | Slc5a3 | solute carrier family 5 (inositol transporters), member 3 | −22.6 |
| NM_020002.1 | Rec8L1 | REC8-like 1 (yeast) | −17.1 |
| AK010101.1 | Galc | galactosylceramidase | −16 |
| BC006869.1 | uk | RIKEN cDNA 2400006A19 gene | −13.9 |
| BI102160 | uk | cDNA sequence BC005561 | −11.3 |
| BG066193 | 2310058J06Rik | RIKEN cDNA 2310058J06 gene | −10.6 |
| BB334959 | Mic2l1 | MIC2 (monoclonal Imperial Cancer Research Fund 2)-like 1 | −9.8 |
| AU046270 | uk | uk | −7.5 |
| AK004748.1 | Riok3 | RIO kinase 3 (yeast) | −7.0 |
| AK011963.1 | Prdx2 | peroxiredoxin 2 | −5.7 |
| BB193024 | Ifitm6 | interferon induced transmembrane protein 6 | −4.9 |
| BM239446 | Rnpc2 | RNA-binding region (RNP1, RRM) containing 2 | −4.9 |
| NM_133194.1 | Scml2 | sex comb on midleg-like 2 (Drosophila) | −4.9 |
| BC026550.1 | Pkig | protein kinase inhibitor, gamma | −4.9 |
| NM_007618.1 | Serpina6 | serine (or cysteine) proteinase inhibitor, clade A, member 6 | −4.9 |
| AF031814.1 | Nr1i2 | nuclear receptor subfamily 1, group I, member 2 | −4.3 |
| NM_025918.1 | D11Ertd707e | DNA segment, Chr 11, ERATO Doi 707, expressed | −4.3 |
| BB794742 | uk | uk | −4 |
| BC002257.1 | BC005512 | cDNA sequence BC005512 | −3.7 |
| AV370372 | Hif1a | hypoxia inducible factor 1, alpha subunit | −3.5 |
| AK003108.1 | 1010001D01Rik | RIKEN cDNA 1010001D01 gene | −3.2 |
| AV239350 | Cps1 | carbamoyl-phosphate synthetase 1 | −3.2 |
| X00686.1 | uk | uk | −3.2 |
| BF580235 | C920004C08Rik | RIKEN cDNA C920004C08 gene | −3.0 |
| X00686.1 | uk | uk | −3.0 |
| AA522020 | uk | uk | −3.0 |
| U03434.1 | Atp7a | ATPase, Cu++ transporting, alpha polypeptide | −3.0 |
| BC016255.1 | Pla2g4b | phospholipase A2, group IVB (cytosolic) | −3.0 |
| BC024761.1 | A230102I05Rik | RIKEN cDNA A230102I05 gene | −2.8 |
| NM_018766.1 | Ntsr1 | neurotensin receptor 1 | −2.8 |
| BQ177187 | 2310007F12Rik | RIKEN cDNA 2310007F12 gene | −2.8 |
| AA185884 | uk | Adult male aorta and vein cDNA, RIKEN full-length enriched library | −2.8 |
| NM_009243.1 | Serpina1a | serine (or cysteine) proteinase inhibitor, clade A, member 1a | −2.6 |
| BC014727.1 | 2310058J06Rik | RIKEN cDNA 2310058J06 gene | −2.6 |
| AK013851.1 | 2900097C17Rik | RIKEN cDNA 2900097C17 gene | −2.6 |
| BB282083 | D6Ertd349e | DNA segment, Chr 6, ERATO Doi 349, expressed | −2.6 |
| X00686.1 | uk | uk | −2.6 |
| AV302111 | Asb4 | ankyrin repeat and SOCS box-containing protein 4 | −2.5 |
| NM_026320.1 | Gadd45gip1 | growth arrest and DNA-damage-inducible, gamma interacting protein 1 | −2.5 |
| AK004399.1 | Cntn1 | contactin 1 | −2.3 |
| BG076129 | Pcm1 | pericentriolar material 1 | −2.3 |
| NM_026515.1 | 2810417H13Rik | RIKEN cDNA 2810417H13 gene | −2.3 |
| BG297038 | uk | uk | −2.3 |
| BF453369 | Rpl17 | ribosomal protein L17 | −2.3 |
| AA762498 | uk | uk | −2.3 |
| BC017598.1 | Rfx3 | regulatory factor X, 3 (influences HLA class II expression) | −2.1 |
| BC008220.1 | A930014I12Rik | RIKEN cDNA A930014I12 gene | −2.1 |
| AW146041 | Akr1c21 | aldo-keto reductase family 1, member C21 | −2.1 |
| AV156860 | Hbb-y | hemoglobin Y, beta-like embryonic chain | −2.1 |
| NM_010329.1 | Gp38 | glycoprotein 38 | −2.1 |
| NM_021281.1 | Ctss | cathepsin S | −2.1 |
| AF174535.1 | Sqrdl | sulfide quinone reductase-like (yeast) | −2.1 |
| AA103697 | uk | uk | −2.1 |
| AV113827 | Asb4 | ankyrin repeat and SOCS box-containing protein 4 | −2 |
| AA798895 | Ccrn4l | CCR4 carbon catabolite repression 4-like (S. cerevisiae) | −2 |
| BC019757.1 | Hist1h4i | histone 1, H4i | −2 |
| BB609699 | MGC41689 | hypothetical LOC211623 | −2 |
| NM_015796.1 | Fbxo17 | F-box only protein 17 | −2 |
| NM_024191.1 | Arl2bp | ADP-ribosylation factor-like 2 binding protein | −2 |
| AV221988 | Ivd | isovaleryl coenzyme A dehydrogenase | −2 |
| BQ030854 | uk | uk | −2 |
| AW108522 | Gatm | glycine amidinotransferase (L-arginine: glycine amidinotransferase) | −2 |
| NM_016890.1 | Dctn3 | dynactin 3 | −2 |
| BB204486 | Phgdh | 3-phosphoglycerate dehydrogenase | −2 |
| BC027328.1 | Bst2, Brd4 | bone marrow stromal cell antigen 2, bromodomain containing 4 | −2 |
| BE198116 | Ccl27 | chemokine (C-C motif) ligand 27 | −2 |
| BG806300 | Xist | inactive X specific transcripts | −2 |
| NM_134086.1 | Slc38a1 | solute carrier family 38, member 1 | −1.9 |
| NM_009114.1 | S100a9 | S100 calcium binding protein A9 (calgranulin B) | −1.9 |
| AK003232.1 | Cbr3 | carbonyl reductase 3 | −1.9 |

TABLE 7-continued 163 down-regulated genes in 17.5 dpc embryonic kidney of Taz$^{-/-}$ mutant
Represented in mouse expression set 430A (Affymetrix)

| Public ID | Gene symbol | Gene title | Fold change |
|---|---|---|---|
| NM_133358.1 | Zfp617 | zinc finger protein 617 | −1.9 |
| BE686792 | uk | uk | −1.9 |
| AK006418.1 | Arl2bp | ADP-ribosylation factor-like 2 binding protein | −1.9 |
| AK017272.1 | Lpl | lipoprotein lipase | −1.9 |
| NM_021608.1 | Dctn5 | dynactin 5 | −1.9 |
| NM_025617.1 | 2210012G02Rik | RIKEN cDNA 2210012G02 gene | −1.9 |
| NM_011521.1 | Sdc4 | syndecan 4 | −1.9 |
| AV037573 | Nt5c3 | 5'-nucleotidase, cytosolic III | −1.9 |
| BM248225 | 6430706D22Rik | RIKEN cDNA 6430706D22 gene | −1.9 |
| BM248225 | Abi1 | abl-interactor 1 | −1.9 |
| NM_019393.1 | Exosc9 | exosome component 9 | −1.9 |
| BB473571 | Slmap | sarcolemma associated protein | −1.9 |
| BF580235 | uk | uk | −1.9 |
| NM_133703.1 | 2810453I06Rik | RIKEN cDNA 2810453I06 gene | −1.7 |
| NM_010511.1 | Ifngr1 | interferon gamma receptor 1 | −1.7 |
| AW124853 | BC030183 | cDNA sequence BC030183 | −1.7 |
| AK004815.1 | Gucy1a3 | guanylate cyclase 1, soluble, alpha 3 | −1.7 |
| BI658327 | Mcm3 | minichromosome maintenance deficient 3 (*S. cerevisiae*) | −1.7 |
| AV003424 | uk | uk | −1.7 |
| BC004747.1 | Zfp386 | zinc finger protein 386 (Kruppel-like) | −1.7 |
| AJ007909.1 | Erdr1 | erythroid differentiation regulator 1 | −1.7 |
| BI143942 | Sdh1 | sorbitol dehydrogenase 1 | −1.7 |
| BB238462 | D3Bwg0562e | DNA segment, Chr 3, Brigham & Women's Genetics 0562 expressed | −1.7 |
| BM207865 | Snx5 | sorting nexin 5 | −1.7 |
| BM935974 | 5031439A09Rik | RIKEN cDNA 5031439A09 gene | −1.7 |
| NM_023644.1 | Mccc1 | methylcrotonoyl-Coenzyme A carboxylase 1 (alpha) | −1.7 |
| NM_030703.1 | Cpn1 | carboxypeptidase N, polypeptide 1 | −1.7 |
| AW323050 | Prss25 | protease, serine, 25 | −1.7 |
| NM_009010.1 | Rad23a | RAD23a homolog (*S. cerevisiae*) | −1.7 |
| BE534815 | Gfra1 | glial cell line derived neurotrophic factor family receptor alpha 1 | −1.7 |
| NM_028746.1 | Slc7a13 | solute carrier family 7, (cationic amino acid transporter, y+ system) member 13 | −1.7 |
| BQ173888 | 6430706D22Rik | RIKEN cDNA 6430706D22 gene | −1.7 |
| NM_008742.1 | Ntf3 | neurotrophin 3 | −1.6 |
| NM_012000.1 | Cln8 | ceroid-lipofuscinosis, neuronal 8 | −1.6 |
| AK005067.1 | 1500003O03Rik | RIKEN cDNA 1500003O03 gene | −1.6 |
| AF483504.1 | Myef2 | myelin basic protein expression factor 2, repressor | −1.6 |
| BB354528 | uk | uk | −1.6 |
| BF235516 | Ptprf | protein tyrosine phosphatase, receptor type, F | −1.6 |
| AW553304 | uk | uk | −1.6 |
| AW988981 | 1110008H02Rik | RIKEN cDNA 1110008H02 gene | −1.6 |
| BB784099 | Skp2 | S-phase kinase-associated protein 2 (p45) | −1.6 |
| NM_026331.2 | Mscp | mitochondrial solute carrier protein | −1.6 |
| AV127023 | Hmgb1 | high mobility group box 1 | −1.6 |
| AF316872.1 | Pink1 | PTEN induced putative kinase 1 | −1.6 |
| AA561726 | Phgdh | 3-phosphoglycerate dehydrogenase | −1.6 |
| NM_011599.1 | Tle1 | transducin-like enhancer of split 1, homolog of *Drosophila* E(spl) | −1.6 |
| NM_011335.1 | Ccl21b | chemokine (C-C motif) ligand 21b (serine) | −1.6 |
| NM_012012.1 | Exo1 | exonuclease 1 | −1.6 |
| NM_021896.1 | Gucy1a3 | guanylate cyclase 1, soluble, alpha 3 | −1.6 |
| BM240191 | Rock1 | Rho-associated coiled-coil forming kinase 1 | −1.6 |
| BF099632 | Kif5b | kinesin family member 5B | −1.6 |
| L04961.1 | Xist | inactive X specific transcripts | −1.6 |
| BI732921 | LOC380969 | similar to KIAA1602 protein | −1.6 |
| BC002019.1 | Nmi | N-myc (and STAT) interactor | −1.6 |
| AV016515 | Cryab | crystallin, alpha B | −1.6 |
| C76813 | Adam17 | a disintegrin and metalloproteinase domain 17 | −1.5 |
| NM_009964.1 | Cryab | crystallin, alpha B | −1.5 |
| NM_018763.1 | Chst2 | carbohydrate sulfotransferase 2 | −1.5 |
| AK014795.1 | Tbc1d15 | TBC1 domain family, member 15 | −1.5 |
| AV209892 | Pkig | protein kinase inhibitor, gamma | −1.5 |
| NM_025390.1 | Pop4 | processing of precursor 4, ribonuclease P/MRP family, (*S. cerevisiae*) | −1.5 |
| AK017012.1 | Sncaip | synuclein, alpha interacting protein (synphilin) | −1.5 |
| AK002487.1 | D15Ertd785e | DNA segment, Chr 15, ERATO Doi 785, expressed | −1.5 |
| AF169407.1 | Pla2g2d | phospholipase A2, group IID | −1.5 |
| NM_008509.1 | Lpl | lipoprotein lipase | −1.5 |
| NM_133222.1 | Eltd1 | EGF, latrophilin seven transmembrane domain containing 1 | −1.5 |
| NM_018858.1 | Pbp | phosphatidylethanolamine binding protein | −1.5 |
| BC022616.1 | 1810045K07Rik | RIKEN cDNA 1810045K07 gene | −1.5 |
| NM_018757.1 | Nme6 | expressed in non-metastatic cells 6, protein | −1.5 |
| BG067113 | Dpp7 | dipeptidylpeptidase 7 | −1.5 |
| NM_011766.1 | Zfpm2 | zinc finger protein, multitype 2 | −1.5 |
| BC025837.1 | Sbk | SH3-binding kinase | −1.5 |

TABLE 7-continued 163 down-regulated genes in 17.5 dpc embryonic kidney of Taz−/− mutant
Represented in mouse expression set 430A (Affymetrix)

| Public ID | Gene symbol | Gene title | Fold change |
|---|---|---|---|
| AK016825.1 | Rnf41 | ring finger protein 41 | −1.5 |
| NM_025956.1 | 1700011H14Rik | RIKEN cDNA 1700011H14 gene | −1.5 |
| NM_013844.1 | Zfp68 | zinc finger protein 68 | −1.5 |
| BB313689 | Mapk10 | mitogen activated protein kinase 10 | −1.5 |
| BC019747.1 | Ogfrl1 | opioid growth factor receptor-like 1 | −1.5 |
| BC026584.1 | Adhfe1 | alcohol dehydrogenase, iron containing, 1 | −1.5 |
| BB034503 | uk | uk | −1.5 |
| D50527.1 | Ubc | ubiquitin C | −1.5 |
| NM_134104.1 | uk | 16 days neonate thymus cDNA, RIKEN full-length enriched library | −1.5 |
| NM_026086.1 | Hdhd4 | haloacid dehalogenase-like hydrolase domain containing 4 | −1.5 |
| BC001985.1 | Ap4s1 | adaptor-related protein complex AP-4, sigma 1 | −1.5 |
| BG862223 | uk | uk | −1.5 |
| NM_009856.1 | Cd83 | CD83 antigen | −1.5 |
| NM_011368.2 | Shc1 | src homology 2 domain-containing transforming protein C1 | −1.5 |
| AK018331.1 | Stard3nl | STARD3 N-terminal like | −1.5 |
| NM_016773.1 | Nucb2 | nucleobindin 2 | −1.5 |
| BM120022 | Lcmt2 | leucine carboxyl methyltransferase 2 | −1.5 |
| NM_024287.1 | Rab6 | RAB6, member RAS oncogene family | −1.5 |

*uk = unknown

TABLE 8

116 up-regulated genes in 17.5 dpc embryonic kidney of Taz−/− mutant
Represented in mouse expression set 430B (Affymetrix)

| Public ID | Gene Symbol | Gene Title | Fold Change |
|---|---|---|---|
| BI664409 | BC023969 | cDNA sequence BC023969 | 36.8 |
| AI661948 | Stk17b | serine/threonine kinase 17b (apoptosis-inducing) | 34.3 |
| AV103696 | Paqr9 | progestin and adipoQ receptor family member IX | 19.7 |
| BE957271 | uk* | uk | 19.7 |
| BB531021 | Grip1 | Glutamate receptor interacting protein 1 | 16 |
| BB667395 | Dhtkd1 | Dehydrogenase E1 and transketolase domain containing 1 | 14.9 |
| AV002049 | BC016495 | cDNA sequence BC016495 | 14.9 |
| AW491340 | uk | uk | 13.9 |
| AK015641.1 | Crem | cAMP responsive element modulator | 13.9 |
| AI506321 | uk | uk | 13.0 |
| BB199135 | Cdc23 | CDC23 (cell division cycle 23, yeast, homolog) | 13.0 |
| AK014544.1 | Slc6a19 | solute carrier family 6 (neurotransmitter transporter), member 19 | 11.3 |
| AV343573 | Cbln4 | cerebellin 4 precursor protein | 11.3 |
| BB240995 | A630024B12Rik | RIKEN cDNA A630024B12 gene | 11.3 |
| AW123227 | uk | uk | 10.6 |
| BB091346 | uk | uk | 10.6 |
| BB160137 | uk | uk | 9.8 |
| BM115076 | uk | uk | 8.6 |
| BB092748 | C130032J12Rik | RIKEN cDNA C130032J12 gene | 8 |
| BG064390 | Ssh1 | slingshot homolog 1 (Drosophila) | 6.5 |
| BE989344 | D3Ertd330e | DNA segment, Chr 3, ERATO Doi 330, expressed | 6.5 |
| BB546415 | Vezf1 | Vascular endothelial zinc finger 1 | 6.5 |
| BB199855 | Ss18 | synovial sarcoma translocation, Chromosome 18 | 6.5 |
| BB738310 | D330022H12Rik | RIKEN cDNA D330022H12 gene | 6.1 |
| BB024162 | 2610207I05Rik | RIKEN cDNA 2610207I05 gene | 6.1 |
| BB306259 | uk | Adult male corpora quadrigemina cDNA, RIKEN full-length enriched library, clone: B230207H05 product: unknown EST, full insert sequence | 5.7 |
| BB082509 | 9330175H22Rik | RIKEN cDNA 9330175H22 gene | 4.9 |
| AI746579 | uk | uk | 4.3 |
| BB184171 | Mapk8 | mitogen activated protein kinase 8 | 4 |
| BB016769 | Atp10d | ATPase, Class V, type 10D | 4 |
| BB149964 | Dmtf1 | Cyclin D binding myb-like transcription factor 1 | 4 |
| BB037161 | Clasp1 | CLIP associating protein 1 | 3.7 |
| AV252614 | C130071C03Rik | RIKEN cDNA C130071C03 gene | 3.7 |
| BB281781 | A930033H14Rik | RIKEN cDNA A930033H14 gene | 3.7 |
| BB526046 | uk | uk | 3.7 |
| BE685845 | uk | uk | 3.5 |
| AK004078.1 | 1110033O09Rik | RIKEN cDNA 1110033O09 gene | 3.5 |
| BB242458 | uk | uk | 2.8 |
| BB461843 | Kcnq5 | Potassium voltage-gated channel, subfamily Q, member 5 | 2.8 |
| BM238996 | uk | uk | 2.5 |
| BB296225 | 6430510M02Rik | RIKEN cDNA 6430510M02 gene | 2.5 |

TABLE 8-continued 116 up-regulated genes in 17.5 dpc embryonic kidney of Taz−/− mutant
Represented in mouse expression set 430B (Affymetrix)

| Public ID | Gene Symbol | Gene Title | Fold Change |
|---|---|---|---|
| BB074968 | Psip1 | PC4 and SFRS1 interacting protein 1 | 2.5 |
| AW552076 | Pabpc1 | Poly A binding protein, cytoplasmic 1 | 2.5 |
| BI788665 | uk | 0 day neonate eyeball cDNA, RIKEN full-length enriched library, | 2.5 |
| BB402666 | Pank2 | pantothenate kinase 2 (Hallervorden-Spatz syndrome) | 2.5 |
| BM211666 | uk | uk | 2.3 |
| AW121199 | uk | uk | 2.3 |
| BB446560 | A630043P06 | Hypothetical protein A630043P06 | 2.1 |
| AK016639.1 | 4933403L11Rik | RIKEN cDNA 4933403L11 gene | 2.1 |
| BE979150 | 2010204O13Rik | RIKEN cDNA 2010204O13 gene | 2.1 |
| AI265463 | Pck1 | phosphoenolpyruvate carboxykinase 1, cytosolic | 2.1 |
| BB667934 | 9930033H14Rik | RIKEN cDNA 9930033H14 gene | 2.1 |
| AI451461 | Taf2 | TAF2 RNA polymerase II, TATA box binding protein (TBP)-associated factor, 150 kDa | 2.1 |
| AI597033 | 2900011L18Rik | RIKEN cDNA 2900011L18 gene | 2.1 |
| AV274006 | Slc9a2 | solute carrier family 9 (sodium/hydrogen exchanger), member 2 | 2.1 |
| BB731108 | uk | uk | 2 |
| AV020525 | uk | uk | 2 |
| BB248730 | Axot | Axotrophin | 2 |
| BF682848 | BC055107 | cDNA sequence BC055107 | 2 |
| BB534930 | Gns | glucosamine (N-acetyl)-6-sulfatase | 2 |
| BB427041 | Usp31 | Ubiquitin specific protease 31 | 2 |
| AI098139 | uk | uk | 2 |
| AW545979 | Pcm1 | Pericentriolar material 1 | 2 |
| AV319507 | Mmrn2 | multimerin 2 | 2 |
| AK002603.1. | 0610012H03Rik | RIKEN cDNA 0610012H03 gene | 2 |
| BB374879 | 5730601F06Rik | RIKEN cDNA 5730601F06 gene | 2 |
| BQ031782 | U2af1-rs2 | U2 small nuclear ribonucleoprotein auxiliary factor (U2AF) 1, related sequence 2 | 1.9 |
| BB466294 | uk | uk | 1.9 |
| BG066278 | uk | uk | 1.9 |
| BB254594 | A730062M13Rik | RIKEN cDNA A730062M13 gene | 1.9 |
| BE457727 | 5830411E10Rik | RIKEN cDNA 5830411E10 gene | 1.9 |
| AW541326 | A430108E01Rik | RIKEN cDNA A430108E01 gene | 1.9 |
| BM231698 | Ext1 | Exostoses (multiple) 1 | 1.9 |
| BF682848 | BC055107 | cDNA sequence BC055107 | 1.9 |
| AK004912.1 | Dusp23 | Dual specificity phosphatase 23 | 1.9 |
| AK003589.1 | 1110008L16Rik | RIKEN cDNA 1110008L16 gene | 1.9 |
| BB493359 | Add3 | adducin 3 (gamma) | 1.7 |
| BB814564 | Trp53bp2 | transformation related protein 53 binding protein 2 | 1.7 |
| BG069665 | uk | uk | 1.7 |
| BB451601 | uk | uk | 1.7 |
| AV341509 | Rgl1 | Ral guanine nucleotide dissociation stimulator,-like 1 | 1.7 |
| AV373997 | Greb1 | gene regulated by estrogen in breast cancer protein | 1.7 |
| BB207587 | Fuk | fucokinase | 1.7 |
| BM940173 | uk | uk | 1.7 |
| AV228812 | Ches1 | checkpoint supressor 1 | 1.7 |
| BB212045 | 9230110M18Rik | RIKEN cDNA 9230110M18 gene | 1.7 |
| BB420529 | 9930031P18Rik | RIKEN cDNA 9930031P18 gene | 1.7 |
| BB748887 | 9130004J05Rik | RIKEN cDNA 9130004J05 gene | 1.7 |
| BB551256 | 6720456B07Rik | RIKEN cDNA 6720456B07 gene | 1.7 |
| AU040322 | Rai16 | retinoic acid induced 16 | 1.6 |
| BB364291 | uk | 16 days embryo head cDNA, RIKEN full-length enriched library | 1.6 |
| AK013898.1 | 3010024O21Rik | RIKEN cDNA 3010024O21 gene | 1.6 |
| BG071002 | uk | uk | 1.6 |
| X57349.1 | Tfrc | transferrin receptor | 1.6 |
| BB744177 | 0610010I15Rik | RIKEN cDNA 0610010I15 gene | 1.6 |
| BE983473 | Gls | Glutaminase | 1.6 |
| BG069626 | uk | uk | 1.6 |
| AV376055 | Mlr1 | Mblk1-related protein-1 | 1.6 |
| BM220840 | uk | uk | 1.6 |
| BB120894 | 9230108I15Rik | RIKEN cDNA 9230108I15 gene | 1.6 |
| BE225764 | Mfhas1 | malignant fibrous histiocytoma amplified sequence 1 | 1.6 |
| BB244383 | Slc15a2 | Solute carrier family 15 (H+/peptide transporter), member 2 | 1.6 |
| BB148843 | uk | uk | 1.5 |
| AK020483.1 | 9430072K23Rik | RIKEN cDNA 9430072K23 gene | 1.5 |
| BG173293 | uk | uk | 1.5 |
| BB434111 | Itpkb | inositol 1,4,5-trisphosphate 3-kinase B | 1.5 |
| BB314393 | uk | uk | 1.5 |
| BG070809 | 1700027M01Rik | RIKEN cDNA 1700027M01 gene | 1.5 |
| BB041366 | C230085J04Rik | Aldo-keto reductase family 1, member B3 (aldose reductase) | 1.5 |
| BB041868 | A430108E01Rik | RIKEN cDNA A430108E01 gene | 1.5 |
| BM114723 | Pbx1 | Pre B-cell leukemia transcription factor 1 | 1.5 |
| AV257745 | 6330403M23Rik | RIKEN cDNA 6330403M23 gene | 1.5 |

TABLE 8-continued 116 up-regulated genes in 17.5 dpc embryonic kidney of Taz−/− mutant
Represented in mouse expression set 430B (Affymetrix)

| Public ID | Gene Symbol | Gene Title | Fold Change |
|---|---|---|---|
| AV375328 | AI987692 | expressed sequence AI987692 | 1.5 |
| AV368819 | uk | uk | 1.5 |
| AI585679 | 2610005L07Rik | RIKEN cDNA 2610005L07 gene | 1.5 |
| BB794831 | Plcb1 | phospholipase C, beta 1 | 1.5 |

*uk = unknown

TABLE 9

61 down-regulated genes in 17.5 dpc embryonic kidney of Taz−/− mutant
Represented in mouse expression set 430B (Affymetrix)

| Public ID | Gene Symbol | Gene Title | Fold Change |
|---|---|---|---|
| BB477150 | uk* | uk | −55.7 |
| AV157113 | uk | uk | −29.9 |
| BB553906 | Fbxo12 | F-box protein 12 | −19.7 |
| AV210092 | 1700017L05Rik | RIKEN cDNA 1700017L05 gene | −18.4 |
| BB656631 | 6230403H02Rik | RIKEN cDNA 1110038H03 gene | −13.0 |
| AW555202 | uk | uk | −12.1 |
| BE956442 | uk | uk | −8.6 |
| AA409309 | Efhd2 | EF hand domain containing 2 | −8 |
| AW546318 | uk | uk | −6.5 |
| BB075190 | C230095G01Rik | RIKEN cDNA C230095G01 gene | −5.7 |
| BB055717 | uk | uk | −5.3 |
| BM244064 | Tde1 | tumor differentially expressed 1 | −4.9 |
| AV349355 | Sctr | secretin receptor | −4.6 |
| BB794862 | Zfp114 | Zinc finger protein 114 | −4.3 |
| AU067772 | uk | 13 days embryo stomach cDNA, RIKEN full-length enriched library, clone: D530018K18 product: unclassifiable, full insert sequence | −4.3 |
| BB503566 | Slc5a12 | solute carrier family 5 (sodium/glucose cotransporter), member 12 | −4 |
| BG073178 | Mid1 | Midline 1 | −3.5 |
| AV337707 | Ankrd29 | Ankyrin repeat domain 29 | −3.2 |
| BB523104 | uk | uk | −3.2 |
| BG072279 | D14Ertd449e | DNA segment, Chr 14, ERATO Doi 449, expressed | −3.0 |
| BB355329 | uk | uk | −3.0 |
| AV245208 | uk | uk | −2.8 |
| X00686.1 | uk | uk | −2.8 |
| AV214133 | uk | uk | −2.8 |
| X00686.1 | uk | uk | −2.8 |
| BG070110 | uk | uk | −2.8 |
| BQ030936 | uk | uk | −2.8 |
| AK010365.1 | Mcm8 | minichromosome maintenance deficient 8 (*S. cerevisiae*) | −2.6 |
| AK004227.1 | 1110051B16Rik | RIKEN cDNA 1110051B16 gene | −2.6 |
| X00686.1 | uk | uk | −2.6 |
| AK018415.1 | 8430415E05Rik | RIKEN cDNA 8430415E05 gene | −2.6 |
| AI594274 | uk | uk | −2.5 |
| AV321065 | 1110051B16Rik | RIKEN cDNA 1110051B16 gene | −2.5 |
| AV029626 | Cklfsf5 | chemokine-like factor super family 5 | −2.5 |
| BM939312 | uk | uk | −2.5 |
| BB182501 | C630043F03Rik | RIKEN cDNA C630043F03 gene | −2.5 |
| BB151104 | Pla2g4b | Phospholipase A2, group IVB (cytosolic) | −2.5 |
| AV290754 | BC050078 | cDNA sequence BC050078 | −2.3 |
| AV277495 | D830007B15Rik | RIKEN cDNA D830007B15 gene | −2.3 |
| BF662057 | Xrn1 | RIKEN cDNA A130001C09 gene | −2.1 |
| BG070110 | uk | uk | −2.1 |
| AK016096.1 | 4930551O13Rik | RIKEN cDNA 4930551O13 gene | −2 |
| AK004327.1 | 1110060I01Rik | RIKEN cDNA 1110060I01 gene | −2 |
| BG067912 | uk | uk | −2 |
| BB305930 | C030033F14Rik | RIKEN cDNA C030033F14 gene | −1.9 |
| C78178 | Dctn5 | dynactin 5 | −1.9 |
| AI642171 | Pgpep1 | pyroglutamyl-peptidase I | −1.9 |
| BB114398 | uk | uk | −1.9 |
| AV301944 | uk | uk | −1.7 |
| BI082172 | Rnu17d | RNA, U17d small nucleolar | −1.7 |
| BM249614 | Alg8 | asparagine-linked glycosylation 8 homolog (yeast, alpha-1,3-glucosyltransferase) | −1.7 |
| BM219285 | Pigl | Phosphatidylinositol glycan, class L | −1.7 |
| BG092677 | uk | uk | −1.7 |
| AV308092 | Cdgap | Cdc42 GTPase-activating protein | −1.7 |

TABLE 9-continued 61 down-regulated genes in 17.5 dpc embryonic kidney of Taz−/− mutant
Represented in mouse expression set 430B (Affymetrix)

| Public ID | Gene Symbol | Gene Title | Fold Change |
|---|---|---|---|
| BI180630 | 2310005L22Rik | RIKEN cDNA 2310005L22 gene | −1.6 |
| BB125651 | Neto2 | neuropilin (NRP) and tolloid (TLL)-like 2 | −1.6 |
| NM_021608.1 | Dctn5 | dynactin 5 | −1.6 |
| AV308579 | uk | Gene model 96, (NCBI) | −1.5 |
| AK017362.1 | Bcl2l12 | BCL2-like 12 (proline rich) | −1.5 |
| BI256061 | Rad23a | RAD23a homolog (*S. cerevisiae*) | −1.5 |
| AK011474.1 | 2610019P18Rik | RIKEN cDNA 2610019P18 gene | −1.5 |

*uk = unknown

---

The invention claimed is:

1. A mouse whose gene encoding transcriptional coactivator with PDZ-binding motif (TAZ) is inactivated through homologous recombination such that the mouse is TAZ –/– and develops polycystic kidney disease (PKD).

2. The mouse of claim 1, wherein the homologous recombination is localized to the kidney.

3. The mouse of claim 1, wherein the mouse has no functional TAZ polypeptide or no nucleic acid encoding said polypeptide.

* * * * *